US012758506B2

(12) United States Patent
Wong et al.

(10) Patent No.: US 12,758,506 B2

(45) Date of Patent: Oct. 13, 2026

(54) METHODS AND COMPOSITIONS FOR DENDRITIC CELL TARGETING NANO-DELIVERY

(71) Applicant: Rock BioMedical, Inc., Taipei City (TW)

(72) Inventors: Chi-Huey Wong, Rancho Santa Fe, CA (US); Jeng Shin Lee, Lincoln, MA (US); Chen-Yo Fan, Taipei City (TW); Szu-Wen Wang, Taipei City (TW); Chung-Yi Wu, Taipei City (TW)

(73) Assignee: ROCK BIOMEDICAL, INC., Taipei City (TW)

( * ) Notice: Subject to any disclaimer, the term of this patent is extended or adjusted under 35 U.S.C. 154(b) by 0 days.

(21) Appl. No.: 19/295,121

(22) Filed: Aug. 8, 2025

(65) Prior Publication Data

US 2026/0014089 A1 Jan. 15, 2026

Related U.S. Application Data

(60) Continuation of application No. PCT/US2024/023597, filed on Apr. 8, 2024, and a division of application No. 18/629,707, filed on Apr. 8, 2024, now Pat. No. 12,508,235.

(60) Provisional application No. 63/575,093, filed on Apr. 5, 2024, provisional application No. 63/587,231, filed on Oct. 2, 2023, provisional application No. 63/458,102, filed on Apr. 8, 2023.

(51) Int. Cl.
*A61K 9/51* (2006.01)

(52) U.S. Cl.
CPC .................................. *A61K 9/5123* (2013.01)

(58) Field of Classification Search
CPC .................................................. A61K 9/5123
See application file for complete search history.

(56) References Cited

U.S. PATENT DOCUMENTS

| | | | |
|---|---|---|---|
| 5,733,762 | A | 3/1998 | Midoux et al. |
| 7,871,626 | B2 | 1/2011 | Hoffmann et al. |
| 8,187,838 | B2 | 5/2012 | Tsukamoto et al. |
| 10,301,377 | B2 | 5/2019 | Graham et al. |
| 10,906,944 | B2 | 2/2021 | He et al. |
| 10,953,089 | B1 | 3/2021 | Smith et al. |
| 10,954,289 | B1 | 3/2021 | Babb et al. |

(Continued)

FOREIGN PATENT DOCUMENTS

| | | |
|---|---|---|
| CN | 105934441 A | 9/2016 |
| CN | 106800650 A | 6/2017 |

(Continued)

OTHER PUBLICATIONS

U.S. Appl. No. 17/937,744, filed Oct. 3, 2022, Kuo-I Lin.

(Continued)

*Primary Examiner* — Carlos A Azpuru

(74) *Attorney, Agent, or Firm* — Prosyla Group, PC

(57) ABSTRACT

The present disclosure relates to novel compounds, methods, and cell-targeting formulations, e.g., a lipid nanoparticle (LNP) for targeted delivery to a tissue or a cell type. The compound and formulation provided herein are designed to have a targeting moiety configured to provide selective delivery features for the formulation and a lipid tail for being incorporated into the bilayer membrane of the formed lipid nanoparticle.

35 Claims, 10 Drawing Sheets

(56) References Cited

U.S. PATENT DOCUMENTS

| | | | |
|---|---|---|---|
| 11,480,391 B2 | 10/2022 | Wong et al. | |
| 11,866,485 B2 | 1/2024 | Lin et al. | |
| 11,918,641 B2 | 3/2024 | Wong et al. | |
| 11,992,525 B2 | 5/2024 | Wong et al. | |
| 12,085,340 B2 | 9/2024 | Wong et al. | |
| 12,157,763 B2 | 12/2024 | Lin et al. | |
| 12,257,298 B2 | 3/2025 | Ma et al. | |
| 12,318,485 B2 | 6/2025 | Wong et al. | |
| 12,348,811 B2 | 7/2025 | Han et al. | |
| 12,508,235 B2 * | 12/2025 | Wong | A61K 9/5123 |
| 2006/0073542 A1 | 4/2006 | Bayer et al. | |
| 2010/0008954 A1 | 1/2010 | Wong et al. | |
| 2010/0041740 A1 | 2/2010 | Wong et al. | |
| 2010/0247571 A1 | 9/2010 | Wong et al. | |
| 2013/0309176 A1 | 11/2013 | Port et al. | |
| 2014/0107049 A1 | 4/2014 | Bennani et al. | |
| 2015/0132330 A1 | 5/2015 | Garcia-Sastre et al. | |
| 2016/0199481 A1 | 7/2016 | Bloom | |
| 2016/0376321 A1 | 12/2016 | Hotez et al. | |
| 2017/0119687 A1 | 5/2017 | Rotello et al. | |
| 2018/0043007 A1 | 2/2018 | LeFebvre et al. | |
| 2019/0000760 A1 | 1/2019 | Akimoto et al. | |
| 2019/0292130 A1 | 9/2019 | Peer et al. | |
| 2019/0388460 A1 | 12/2019 | Hedrick et al. | |
| 2020/0046826 A1 | 2/2020 | Wong et al. | |
| 2020/0078452 A1 | 3/2020 | Wong et al. | |
| 2020/0079808 A1 | 3/2020 | Pfister et al. | |
| 2020/0231633 A1 | 7/2020 | Berman et al. | |
| 2020/0283743 A1 | 9/2020 | Zhang et al. | |
| 2021/0017563 A1 | 1/2021 | Bhatnagar et al. | |
| 2021/0207106 A1 | 7/2021 | Anthony et al. | |
| 2021/0316002 A1 | 10/2021 | Ellis | |
| 2021/0386852 A1 | 12/2021 | Duprex | |
| 2022/0233713 A1 | 7/2022 | Callan et al. | |
| 2023/0074185 A1 | 3/2023 | Wong et al. | |
| 2023/0105209 A1 | 4/2023 | Lin et al. | |
| 2023/0279080 A1 | 9/2023 | Lin et al. | |
| 2023/0302114 A1 | 9/2023 | Wong | |
| 2024/0016917 A1 | 1/2024 | Ma et al. | |
| 2024/0066113 A1 | 2/2024 | Wong et al. | |
| 2024/0100147 A1 | 3/2024 | Wong et al. | |
| 2024/0228591 A1 | 7/2024 | Lin et al. | |
| 2024/0366516 A1 | 11/2024 | Wong et al. | |
| 2024/0366517 A1 | 11/2024 | Wong et al. | |
| 2024/0384320 A1 | 11/2024 | Wong et al. | |
| 2025/0041222 A1 | 2/2025 | Wong et al. | |
| 2025/0082744 A1 | 3/2025 | Wong et al. | |
| 2025/0114446 A1 | 4/2025 | Wu et al. | |
| 2025/0136668 A1 | 5/2025 | Lin et al. | |
| 2025/0137725 A1 | 5/2025 | Wong et al. | |
| 2025/0332247 A1 | 10/2025 | Ma et al. | |
| 2025/0333690 A1 | 10/2025 | Wong et al. | |

FOREIGN PATENT DOCUMENTS

| | | | |
|---|---|---|---|
| CN | 108653743 A | 10/2018 | |
| CN | 109350598 A | 2/2019 | |
| CN | 111892648 A | 11/2020 | |
| CN | 112626124 A | 4/2021 | |
| CN | 113388011 A | 9/2021 | |
| CN | 114081961 A | 2/2022 | |
| CN | 116478948 A | 7/2023 | |
| EP | 1987068 A1 | 11/2008 | |
| EP | 2949665 A1 | 12/2015 | |
| JP | 2012530499 A | 12/2012 | |
| JP | 2017518989 A | 7/2017 | |
| JP | 2023541094 A | 9/2023 | |
| JP | 2023552265 | 12/2023 | |
| RU | 2720614 C1 | 5/2020 | |
| RU | 2730897 C1 | 8/2020 | |
| WO | 2004099240 A2 | 11/2004 | |
| WO | 2004099240 A3 | 11/2004 | |
| WO | 2007008918 A2 | 1/2007 | |
| WO | 2007095506 A1 | 8/2007 | |
| WO | 2009002516 A1 | 12/2008 | |
| WO | 2009007427 A2 | 1/2009 | |
| WO | 2010022737 A1 | 3/2010 | |
| WO | 2010111687 A2 | 9/2010 | |
| WO | 2010148511 A1 | 12/2010 | |
| WO | 2011112889 A2 | 9/2011 | |
| WO | 2011115862 A1 | 9/2011 | |
| WO | 2012054907 A2 | 4/2012 | |
| WO | 2012088428 A1 | 6/2012 | |
| WO | 2013043729 A1 | 3/2013 | |
| WO | 2013067652 A1 | 5/2013 | |
| WO | 2014115797 A1 | 7/2014 | |
| WO | 2015057942 A1 | 4/2015 | |
| WO | 2015073727 A1 | 5/2015 | |
| WO | 2015176662 A1 | 11/2015 | |
| WO | 2015184004 A1 | 12/2015 | |
| WO | 2017062496 A2 | 4/2017 | |
| WO | 2017081082 A2 | 5/2017 | |
| WO | 2018089407 A1 | 5/2018 | |
| WO | 2019028190 A1 | 2/2019 | |
| WO | 2015028478 A1 | 6/2019 | |
| WO | 2019246363 A1 | 12/2019 | |
| WO | 2020011275 A1 | 1/2020 | |
| WO | 2020058239 A1 | 3/2020 | |
| WO | 2020172072 A1 | 8/2020 | |
| WO | 2020198865 A1 | 10/2020 | |
| WO | 2020205034 A1 | 10/2020 | |
| WO | 2021019102 A2 | 2/2021 | |
| WO | 2021035325 A1 | 3/2021 | |
| WO | 2021045632 A1 | 3/2021 | |
| WO | 2021045836 A1 | 3/2021 | |
| WO | 2021174128 A1 | 9/2021 | |
| WO | 2021180602 A1 | 9/2021 | |
| WO | 2021183195 A1 | 9/2021 | |
| WO | 2021186028 A1 | 9/2021 | |
| WO | 2021214204 A1 | 10/2021 | |
| WO | 2021219897 A1 | 11/2021 | |
| WO | 2021226533 A1 | 11/2021 | |
| WO | 2021233989 A1 | 11/2021 | |
| WO | 2021257586 A1 | 12/2021 | |
| WO | 2022047401 A1 | 3/2022 | |
| WO | 2022221835 A2 | 10/2022 | |
| WO | 2022221837 A2 | 10/2022 | |
| WO | 2022227927 A1 | 11/2022 | |
| WO | 2022229854 A1 | 11/2022 | |
| WO | 2022231980 A1 | 11/2022 | |
| WO | 2023/02111 A1 | 2/2023 | * |
| WO | 2023021111 A1 | 2/2023 | |
| WO | 2023056482 A1 | 4/2023 | |
| WO | 2023069551 A1 | 4/2023 | |
| WO | 2023129928 A2 | 7/2023 | |
| WO | 2024215612 A2 | 10/2024 | |
| WO | 2024215614 A2 | 10/2024 | |
| WO | 2024215616 A2 | 10/2024 | |
| WO | 2024238734 A2 | 11/2024 | |

OTHER PUBLICATIONS

U.S. Appl. No. 17/998,208, filed Nov. 8, 2022, Chi-Huey Wong.

U.S. Appl. No. 18/005,573, filed Jan. 13, 2023, Che Ma.

U.S. Appl. No. 18/029,758, filed Mar. 31, 2023, Chi-Huey Wong.

U.S. Appl. No. 18/146,873, filed Dec. 27, 2022, Kuo-I Lin.

U.S. Appl. No. 63/588,932, filed Oct. 9, 2023, Chi-Huey Wong.

Alam, MM et al., "Glycan-Modified Virus-Like Particles Evoke T Helper Type 1-Like Immune Responses," ACS Nano, vol. 15, No. 1, Jan. 26, 2021, published online Aug. 17, 2020, doi: 10.1021/acsnano.0c03023, pp. 309-321; (p. 19, figure 1b).

Almaraz, Ruben T. et al., "Metabolic Oligosaccharide Engineering: Implications for Selectin-Mediated Adhesion and Leukocyte Extravasation," Ann Biomed Eng., Apr. 2012, vol. 40, Art. 4, pp. 806-815. doi: 10.1007/s10439-011-0450-y.

Avinash, MB et al., "Nanoarchitectonics of biomolecular assemblies for functional applications," Nanoscale, vol. 6, No. 22, Nov. 21, 2014, doi: 10.1039/c4nr04340e, pp. 13348-13369. (p. 18, figure 13c).

Bang, Eun-Kyoung et al., JACS, 2013, vol. 135, pp. 2088-2091. dx.doi.org/10.1021/ja311961k.

(56) References Cited

OTHER PUBLICATIONS

Bej, Raju et al., "Disulfide chemistry in responsive aggregation of amphiphilic systems," Royal Society of Chemistry, 2020, vol. 16, pp. 11-26. DOI: 10.1039/C9SM01960J.

Bellato, Frederica, "Targeting dendritic cells with mannosylated cationic glycopolymers for nucleic acid-mediated cancer immunotherapy," UNITesi, Magazzini Digitali, 2019, 25 pages. (https://tesidottorato.depositolegale.it/handle/20.500.14242/98191).

Bennua-Skalmowski, B. et al., "A Facile Conversion of Primary or Secondary Alcohols with n-Perfluorobutane-sulfonyl Fluoride/1,8-Diazabicyclo[5.4.0]undec-7-ene into their Corresponding Fleorides," Tetrahedron Letters, vol. 36, No. 15, pp. 2611-2614, 1995.

Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.

Bosch, Berend Jan et al., "Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.

Byrne et al., "CRISPR/Cas9 gene editing for the creation of an MGAT1-deficient CHO cell line to control HIV-1 vaccine glycosylation," PLOS Biology, 2018, vol. 16, No. 8: e2005817.

Cao, Yiwei et al., "Dynamic Interactions of Fully Glycosylated SARS-CoV-2 Spike Protein with Various Antibodies," JCTC, Sep. 16, 2021, vol. 17, pp. 6559-6569.

Cao, Yunlong et al., "Omicron escapes the majority of existing SARS-CoV-2 neutralizing antibodies," Nature, Dec. 23, 2021, vol. 602, No. 7898, pp. 657-663. XP037700795, DOI: 10.1038/S41586-021-04385-3.

Casalino, Lorenzo et al., "Beyond Shielding: The ROles of Glycans in the SARS-CoV-2 Spike Protein," ACS Central Science, 2020, vol. 6, No. 10, pp. 1722-1734. http://pubs.acs.org/journal/acscii.

Castrucci, M.R. et al., "Biologic importance of neuramindase stalk length in influenza A virus", Journal of Virology, 1993, vol. 67, No. 2, pp. 759-764.

Cheng, Cheng-Wei et al., "Low-sugar universal mRNA vaccine against coronavirus variants with deletion of glycosites in the S2 or stem of SARS-CoV-2 spike messenger RNA (mRNA)," PNAS, 2023, vol. 120, No. 49, 8 pages. doi: 10.1073/pnas.2314392120.

Chokhawala, H.A. et al., "Enzymatic Synthesis of Fluorinated Mechanistic Proves for Sialidases and Sialyltransferases", J.Am. Chem. Soc., 2007, p. 10630; scheme 1.

Chokhawala, Harshai A. et al., "Enzymatic Synthesis of Fluorinated Mechanistic Probes for Sialidases and Sialytransferases," JACS Communications, 2007, vol. 129, pp. 10630-10631.

Chuard, Nicolas et al., "Cell-penetrating poly(disulfide)s: the dependence of activity, depolymerization kinetics and intracellular localization on their length," Organic & Biomolecular Chemistry, 2015, vol. 13, pp. 64-67.

Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.

Davies, Nicholas G. et al., "Estimated transmissibility and impact of SARS-CoV-2 lineage B. 1.1.7 in England," Science, Apr. 2021, vol. 372, pp. 149 (10 pages).

Definition of hemagglutinin [Influenza A virus (A/chicken/Jembrana/BPPV6/2004(H5N1))]. GenBank: ABE97562.1. https://www.ncbi.nlm.nih.gov/protein/ABE97562.1?report=genbank&log$=prottop&blast_rank=1&RID=CGUK0N57013.

Definition of hemagglutinin [Influenza A virus (A/Singapore/GP4444/2010(H1N1))]. GenBank: AEH59357.1. https://www.ncbi.nlm.nih.gov/protein/AEH59357.1?report=genbank&log$=prottop&blast_rank=1&RID=CGTA0JCD016.

Ding, Li et al., "A *Photobacterium* sp. [alpha]2-6-sialyltransferase (Psp2,6ST) mutant with an increased expression level and improved activities in sialylating Tn antigens," Carbohydrate Research, 2014, vol. 408, 127-133 (7 pages).

Doboszewski, Bogdan et al., "The rapid synthesis of deoxyfluoro sugars using tris(dimethylamino)sulfonium difluorotrimethylsilicate (TASF)1," 1987, Canadian Journal of Chemistry, 65(2): 412-419.

Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.

Du, Dan et al., "The role of glucose transporters in the distribution of p-aminophenyl-[alpha]-D-mannopyranoside modified liposomes within mice brain," Journal of Controlled Released, 2014, vol. 182. pp. 99-110.

Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1):103-18; doi: 10.1016/jmb.2003.09.054. PMID 14596803.

Engdahl, Cecilia et al., "Estrogen induces St6gal1 expression and increases IgG sialylation in mice and patients with rheumatoid arthritis: a potential explanation for the increased risk of rheumatoid arthritis in postmenopausal women," Arthritis Research & Therapy, 2018, vol. 20:84 (11 pages).

Fan, CY et al., "Synthesis of Dendritic Cell-Targeted Polymeric Nanoparticles for Selective Delivery of mRNA Vaccines to Elicit Enhanced Immune Responses," bioRxiv, Epub: Nov. 14, 2023; pp. 1-12; entire document; DOI: 10.1101/2023.11.13.566827.

Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.

Focosi, Daniele, "Neutralising antibody escape of SARS-CoV-2 spike protein: Risk assessment for antibody-based Covid-19 therapeutics and vaccines," Rev. Med Virol., 2021, vol. 31, 21 pages. e2231.

Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.

Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.

Galili, Uri, "COVID-19 variants as moving targets and how to sop them by glycoengineered whole-virus vaccines," Virulence, 12:1, 1717-1720, DOI: 10.1080/21505594.2021.1939924. (https://doi.org/10.1080/21505594.2021.1939924).

Geisler, Christoph et al., "Engineering [beta]1,4-galactosyltransferase I to reduce secretion and enhance N-glycan elongation in insect cells," Journal of Biotechnology, 2015, vol. 193, 52-65 (14 pages).

GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.

GenBank Accession CCH23214, haemagglutinin [Influenza A virus (A/WSN/1933(H1N1))], 2013.

GenBank accession MN908947.3, Mar. 18, 2020, 11 pages. (https://www.ncbi.nlm.nih.gov/nuccore/MN908947).

GenBank Accession NCBI No. QHD43416.1 (surface glycoprotein [Severe acute respiratory syndrome coronavirus 2]; published Mar. 18, 2020.

GenBank Accession No. MW560959.1 dated Mar. 21, 2021. www.ncbi.nlm.nih.gov/nucleotide/MW560959.1 (Year: 2021).

GenBank Accession No. nC_048600.1 (Cricetulus griseus strain 17A/GY chromosome 7, alternate assembly CriGri-PICRH-1.0, whole genome shotgun sequence. Jul. 12, 2020.

GenBank Accession No. UFO69279.1 dated Nov. 30, 2021. https://www.ncbi.nlm.nih.gov/protein/UFO69279.1 (Year: 2021).

GenBank Accession No. YP_009724390.1 dated Jul. 18, 2020. https://www.ncbi.nlm.nih.gov/protein/YP_009724390.1 (Year: 2020).

GenBank Accession, ACF54601, neuraminidase [Influenza A virus (A/WSN/1933(H1N1))], 2008.

(56) References Cited

OTHER PUBLICATIONS

GenBank Accession: QHD43416.1, (Mar. 18, 2020) [Described in the Office Action as Appendix A] (Year: 2020).
GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.
GenBank: QTA38985.1 accessed Mar. 21, 2021. https://www.ncbi.nlm.nih.gov/protein/QTA38985.1?report=genbank&log$=protalign&blast_rank=3&RID=EYKWWEAA016.
Gillian, M. Air, "Influenza neuraminidase", Influenza and Other Respiratory Viruses, 2011.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.
Gong, Yanqiu et al., "The glycosylation in SARS-CoV-2 and its receptor ACE2," Signal Transduction and Targeted Therapy, 2021, vol. 6, 396 (24 pages).
Goswami, Roshan et al., "Conjugation of Mannans to Enhance the Potency of Liposome Nanoparticles for the Delivery of RNA Vaccines," Pharmaceutics, 2021, vol. 13, 240, 13 pages.
Grant, Oliver C. et al., "Analysis of the SARS-CoV-2 spike protein glycan shield reveals implications for immune recognition," Scientific Reports, 2020, vol. 10, 14991. https://doi.org/10.1038/s41598-020-71748-7.
Gutierrez Reyes, Cristian D., et al. "N-Glycome Profile of the Spike Protein S1: Systemic and Comparative Analysis from Eleven Variants of SARS-CoV-2," Biomolecules, 2023, vol. 13, pp. 1421 (17 pages).
Hayashi, T. et al., "Stereospecific α-Sialylation by SIte-Selective Fluorination", Agnew. Chem. Int. Ed., Jan. 25, 2019, vol. 58, pp. 3814-3818. (Whole Document).
He, P. et al., "Advances in aluminum hydroxide-based adjuvant research and its mechanism," Human Vaccine and Immunotherapeutics, 2015, vol. 11, iss. 2, pp. 477-488.
Hombu, Ryoma et al., "Cellular and Molecular Engineering of Glycan Sialylation in Heterologous Systems," Molecules, 2021, vol. 26, 5950 (27 [ages).
Huang et al., "Impact of glycosylation on SARS-CoV-2 infection and broadly protective vaccine design," BioRxiv, May 25, 2021, DOI: https://doi.org/10.1101/2021.05.25.445523, internal pp. 1-48.
Huang et al., "Vaccination with SARS-CoV-2 spike protein lacking glycan shields elicits enhanced protective responses in animal models," Sci Transl Med., Apr. 6, 2022, vol. 14(639):eabm0899.
Huang, Han-Yi et al., "Vaccination with SARS-CoV-2 spike protein lacking glycan shields elicits enhanced protective responses in animal models," Sci. Transl. Med., vol. 14, eabm0899, (2022), 13 pages.
Huang, Yuan et al., "Structural and functional properties of SARS-CoV-2 spike protein: potential antivirus drug development for COVID-19," Acta Pharmacologica Sinica, (2020), 41:1141-1149; https://doi.org/10.1038/s41401-020-0485-4.
Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.
International Search Report and Written Opinion issued on Jun. 22, 2023 in International Patent Application No. PCT/US22/82428.
Janeway Jr., Charles A et al., "Immunobiology: The Immune System in Health and Disease," 3rd edition, Garland Publishing Inc., 1997, pp. 3:1-3:11.
Kanyavuz, Alexia et al., "Breaking the law: unconventional strategies for antibody diversification," Nat Rev Immunol., Jun. 2019, 19(6):355-368. doi: 10.1038/S41577-019-0126-7. PMID: 30718829.
Krammer, Florian et al., "Chimeric Hemagglutinin Influenza Virus Vaccine Constructs Elicit Broadly Protective Stalk-Specific Antibodies," Journal of Virology, Jun. 2013, vol. 87, No. 12, pp. 6542-6550.
Kurzawa, Timon, "1,1,2,2,3,3,4,4,4-Nonafluorobutane-1-sulfonyl fluoride (NfF)," Synlett, 2015, vol. 26, pp. 1422-1423.
Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.
Levit, Mariia et al., "Bio-Inspired Amphiphilic Block-Copolymers Based on Synthetic Glycopolymer and Poly(Amino Acid) as Potential Drug Delivery Systems," Polymers, 2020, vol. 12, pp. 183 (27 pages). doi:10.3390/polym12010183.
Li, et al., Glycosylation of Neuraminidase Determines the Neurovirulence of Influenza A/WVSN/33 Virus, 1993, Journal of Virology, vol. 67, No. 11, pp. 6667-6673.
Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.
Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.
Lo, H.-J. et al., "Synthesis of Sialidase-Resistant Oligosaccharide and Antibody Glycoform Containing α2,6-Linked 3Fax-Neu5Ac", J. Am. Chem. Soc., Apr. 10, 2019, vol. 141, No. 16, pp. 6484-6488. (Whole Document.).
Lostalé-Seijo, Irene and Montenegro, Javier, "Synthetic materials at the forefront of gene delivery," Nature Reviews Chemistry, vol. 2, Sep. 21, 2018, pp. 258-277.
Ma et al., "The Role of Glucose Transporters in the Distribution of p. aminophenyl mannppyranose modified liposomes within mice brains," Journal of Controlled Release, 182, pp. 99-110. (Year: 2014).
Magazine, Nicholas et al., "Mutations and Evolution of the SARS-CoV-2 Spike Protein," Viruses, 2022, vol. 14, 640, 11 pgs.
Medina, Rafael A. et al., "Glycosylations in the globular head of the hemagglutinin protein modulate the virulence and antigenic properties of the H1N1 influenza viruses", Sci Transl Med., May 29, 2013.
Nobusawa et al., "Comparison of Complete Amino Acid Sequences and Receptor-Binding Properties among 13 Serotypes of Hemagglutinins of Influenza A Viruses", Virology, 182, 475-485 (1991).
Non-Final Office Action issued in U.S. Appl. No. 17/937,744 dated Jul. 5, 2023.
Office Action and Search Report issued in Taiwan Patent Application No. 111113933 on Mar. 26, 2024. English translation of search report.
Office Action issued in Taiwan Patent Application No. 111113932 on Oct. 16, 2023.
Office Action issued on Nov. 14, 2022, in Israel Patent Application No. 293502.
Official Action, dated Aug. 31, 2023, received in Russia Patent Application No. 2023100504. English translation provided.
Okamoto, K. et al., "An effective synthesis of α-glycosides of N-acetylneuraminic acid by use of 2β-halo-3β-hydroxy-4,7,8,9-tetra-O-acetyl-N-acetylneuraminic acid methyl ester", Tetrahedron Letters, 1986, vol. 27, No. 43, pp. 5233-5236.
Pappalardo, Juan Sebastian et al., "Characterization of a Nanovaccine Platform Based on an [alpha]1,2-Mannobiose Derivative Shows Species-non-specific Targeting to Human, Bovine, Mouse, and Teleost Fish Dendritic Cells," Molecular Pharmaceutics, 2021, vol. 18, 2540-2555.
Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.
Rees-Spear, Chloe et al., "The effect of spike mutations on SARS-CoV-2 neutralization," Cell Rep., Mar. 2023, 34 (12): 108890. Published online Mar. 6, 2021. doi: 10.1016/j.celrep.2021.108890: 10.1016/j.celrep.2021.108890 PMCID: PMC7936541 PMID: 33713594.
Roberts, Paul C. et al., "Role of Conserved Glycosylation Sites in Maturation and Transport of Influenza A Virus Hemagglutinin", Journal of Virology, Jun. 1993, p. 3048-3060.

(56) References Cited

OTHER PUBLICATIONS

Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.
Sanda, Miloslav et al., "N- and O-Glycosylation of the SARS-CoV-2 Spike Protein," Anal. Chem., vol. 93, No. 4, Jan. 7, 2021, pp. 2003-2009.
Search Report, dated Aug. 31, 2023, received in Russia Patent Application No. 2023100504.
Shin et al., "CRISPR/Cas9 targeting events cause complex deletions and insertions at 17 sites in the mouse genome," Nature Communications, 2017, vol. 8, Art. 15464.
Shivatare, Vidya et al., "Study on antibody Pc-glycosylation for optimal effector functions," Chem Commun (Camb), 2024, vol. 59, iss. 37, pp. 5555-5558. doi:10.1039/d3cc00672g.
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Sun, Da and Lu, Zheng-Rong, "Structure and Function of Cationic and lonizable Lipids for Nucleic Acid Delivery," Pharmaceutical Research, (2023), 40:27-46. https://doi.org/10.1007/s11095-022-03460-2.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020;17(6):613-620 https://pubmed.ncbi.nlm.nih.gov/32203189/.
Tian, Jing-Hui et al., "SARS-CoV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.
UniProt, ID: B4GT-1_HUMAN, P15291, available Oct. 17, 2006 (Year: 2006).
Vogel, Annette B. et al. "BNT162b vaccines protect rhesus macaques from SARS-CoV-2," Nature, vol. 592, Feb. 1, 2021, pp. 283-289.
Wang, Ce et al., "Lymphatic-targeted cationic liposomes: A robust vaccine adjuvant for promoting long-term immunological memory," Vaccine, 2014, vol. 32, 5475-5483.
Wang, Ce et al., Supplementary Data, 2014, Vaccine, 32, 5475-5483.
Wang, Mingqun et al., "Engineering a bacterial sialyltransferase for di-sialylation of a therapeutic antibody," Organic & Biomolecular Chemistry, 2020, vol. 18, 2886, 7 pages. DOI: 10.1039/d0ob00276c.
Wang, Qiong et al., "Antibody glycoengineering strategies in mammalian cells," Biotechnology and Bioengineering, 2018, vol. 115:1378-1393.
Wang, Shih-Chi et al., "Development of a universal influenza vaccine using hemagglutinin stem protein produced from Pichia pastoris," Virology, 2019, vol. 526, pp. 125-137.
Watanabe, Yasunori et al., "Exploitation of glycosylation in enveloped virus pathobiology," BBA—General Subjects 1863, 2019), pp. 1480-1497.
Watanabe, Yasunori et al., "Site-specific glycan analysis of the SARS-CoV-2 spike," Science, Jul. 2020, vol. 369, pp. 330-333.
Weissman, Drew et al., "D614G Spike Mutation Increases Sars CoV-2 Susceptibility to Neutralization," Cell Host & Microbe, Jan. 13, 2021, vol. 29, pp. 23-31 (e1-e4).
Wu, Chung-Yi et al., "Glycosite-deleted mRNA of SARS-CoV-2 spike protein as a broad-spectrum vaccine," PNAS, 2022, vol. 119, No. 9. https://doi.irg/10.1073/pnas.2119995119.
Wu, Chung-Yi et al., "Influenza A surface glycosylation and vaccine design", PNAS, Jan. 2017, (Epub Dec. 27, 2016), vol. 114, No. 2, pp. 280-285.
Yang et al., "Glucoproteomic Characterization of FUT8 Knock-Out Cells Reveals Roles of FUT8 in the Glycosylation," Frontiers in Chemistry, Oct. 28, 2021, vol. 9, No. 755238, pp. 1-9, entire document.
Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
Zhang, Penghui et al., "Engineering the Surface of Smart Nanocarriers Using a pH-/Thermal-/GSH-Responsive Polymer Zipper for Precise Tumor Targeting Therapy in Vivo," Advanced Materials, 2017, vol. 29, 1702311 (10 pages).
Zhang, Ruhe et al., "Poly(disulfide)s: From Synthesis to Drug Delivery," Bio Macromolecules, 2022, vol. 23, pp. 1-19.
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", Plos One, vol. 8, Issue 4, Apr. 2013.
Zhang, Yong et al., "Site-specific N-glycosylation Characterization of Recombinant SARS-CoV-2 Spike Proteins," Mol Cell Proteomics, 2021, vol. 20, 100058. https://doi.org/10.1074/mcp.RA120.002295.
Zhao, "Glycans of SARS-CoV-2 Spike Protein in Virus Infection and Antibody Production", Frontiers in Molecular Biosciences, Apr. 13, 2021; Entire Document; DOI: 10.3389/fmolb.2021.629873.
Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, column 5th paragraph; p. 68, first column, first, third paragraphs; Table 3; figure 5; http://dx.doi.org/10.1016/j.virol.2017.10.003.
Zhou, Daming et al., "Structural basis for the neutralization of SARS-CoV-2 by antibody from convalescent patient," Nature Structural & Molecular Biology, Oct. 2020, vol. 27, pp. 950 (25 pages).
Chen, Zigui et al., "Genomic and evolutionary comparison between SARS-CoV-2 and other human coronaviruses," J of Virol. Methods, (2021), vol. 289, 114032, 11 pages.
Huang, Han-Wen et al., "Cell-based production of Fc-GlcNAc and Fc-alpha-2,6 sialyl glycan enriched antibody with improved effector functions through glycosylation pathway engineering," bioRxiv, (Dec. 19, 2023), 11 pages. doi: https://doi:org/10.1101/2023.12.18.572280.
Mills, Brittney J et al., "Effect of Linker-Drug Properties and Conjugation Site on the Physical Stability of ADCs," J of Pharm Sci, (2020), vol. 109:1662-1672.
Miyazaki, Takuya et al., "Guanidine-phosphate interactions stabilize polyion complex micelles based on flexible catiomers to improve mRNA delivery," European Polymer Journal, (2020), vol. 140, 110028.
Pearson, Darren and LIS, Hengguang, " Conjugates toward medicines," J. Pharmacol Med Chem, (2017), vol. 1, No. 1, pp. 32-33.
Rossiyskye Nanotekhnologii, "Nanoformulations of Drugs Based on Biodegradable Lactide Copolymers with Various Molecular Structures and Architectures," 2021, v. 16, N. 4, pp. 462-481.
Wu, T.N. et al., Avidity of CD1d-ligand-receptor ternary complex contributes to T-helper 1 (Th1) polarization and anticancer efficacy. Proceedings of the National Academy of Sciences, Oct. 10, 2011, vol. 108, No. 42, pp. 17275-17280. Fig. 1, Compound C34.
Harijan, Manjeet and Singh, Meenakshi, "Zwitterionic polymers in drug delivery: A review," J of Mol. Recog., Nov. 4, 2021; https://doi.org/10.1002/jmr.2944. Abstract.
Javid-Naderi, Mohammad Javad et al., "Nanocarriers for Diagnosis and Treatment of Oncology," Apr. 17, 2026. doi: https://doi.org/10.1002/9781394384891.ch1. Abstract.

(56) References Cited

OTHER PUBLICATIONS

Kondratieva T.S et al. Drug form technology: Manual in 2 volumes. vol. 1.—Moscow: Meditsina, 1991—496 p. (pp. 36 and 44) (Still awaiting document from Russian patent agent, will provide upon receipt).
Marrache, Sean et al., “Nanocarriers for Tracking and Treating Diseases,” Curr Med Chem., 2013; vol. 20 (28):3500-3514. doi: 10.2174/0929867311320280007.
Morachis, Jose M et al., “Physical and Chemical Strategies for Therapeutic Delivery by Using Polymeric Nanoparticles,” Pharmrev Fast Forward, Apr. 27, 2012, vol. 64, No. 3, doi: 10.1124/pr.111.005363.
Saraswathi, Tenpattinam Shanmugam et al., “Recent advances in potential drug nanocarrier for CNS disorders: a review,” Biomed Eng Online, Nov. 21, 2025; vol. 24:137. doi: 10.1186/s12938-025-01474-6.
Sutyagin V.M., Bondaletova L.I. Chemistry and Physics of Polymers: Manual.—Tomsk: TPU Publishing House, 2003.—208 p., (p. 142).
Zhang, Yuebao et al., “Lipids and lipid derivatives for RNA delivery,” Chemical Reviews, (Jul. 19, 2021), vol. 121, Issue 20, pp. 12181-12277.

* cited by examiner

Exact Mass: 1357.7197

METHODS AND COMPOSITIONS FOR DENDRITIC CELL TARGETING NANO-DELIVERY

CROSS-REFERENCE TO RELATED APPLICATIONS

This application is a divisional of U.S. patent application Ser. No. 18/629,707, filed Apr. 8, 2024, which claims the priority of U.S. Provisional Patent Applications No. 63/458,102, filed on Apr. 8, 2023, U.S. Provisional Patent Applications No. 63/587,231, filed on Oct. 2, 2023, U.S. Provisional Patent Applications No. 63/575,093, filed on Apr. 5, 2024, and PCT patent application no. PCT/US24/23597, filed on Apr. 8, 2024, titled "METHODS AND COMPOSITIONS FOR DENDRITIC CELL TARGETING VACCINES." The entireties of the aforementioned applications are incorporated herein by reference.

FIELD

The instant disclosure relates to novel formulations for targeted nano-delivery. Specifically, the disclosure relates to compositions and methods directed to novel bi-functional nanoparticle formulations capable of selectively delivering a payload to a desired region in a tissue or a specific cell type, including dendritic cells.

BACKGROUND OF THE INVENTION

Localized delivery via nanotechnology has been widely used in scientific, industrial, and clinical applications. It has increasingly become a promising way for drug delivery, providing advantages including improving solubility and penetration of drug molecules. In recent examples of the mRNA vaccines developed against COVID-19 viruses, in view of mRNA molecules' instability and need for low-temperature storage (e.g., −70° C.), lipid nanoparticles (LNP) were developed to encapsulate and stabilize mRNA molecules both in transit and once injected into the human body. The lipid nanoparticles are usually composed of several types of lipids. The ratio of those lipids requires fine-tuning, and the manufacturing of the lipid nanoparticles can be costly, and most importantly, the lipid nanoparticles generally cannot deliver the mRNA molecules with much localized selectivity. Therefore, there is an unmet need for novel nanoparticle formulations with selective delivery functionality.

BRIEF SUMMARY OF THE INVENTION

One aspect of the present disclosure is directed to a bi-functional compound for forming a lipid nanoparticle suitable for pharmaceutical formulation. The component comprises the formula:

Formula 1

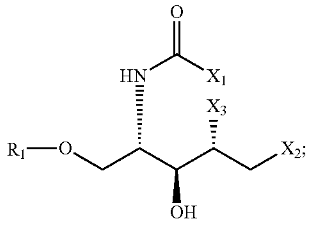

or

-continued

Formula 2

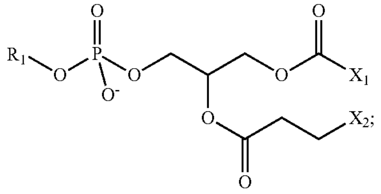

wherein $R_1$ comprises a substituted or non-substituted glycosyl group;

wherein $X_1$ and $x_2$ are each independently hydrogen, $C_{1-30}$ alkyl, $C_{1-30}$ alkenyl, $C_{1-30}$ alkynyl, aryl, aryloxy, or a substituted version thereof, or —$(CH_2)nX_4$, n is 0 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof, and wherein $X_3$ is hydrogen, $C_{1-6}$ alkyl, or hydroxyl.

One aspect of the present disclosure is directed to a formulation for forming a lipid nanoparticle, comprising the compound of the present disclosure, wherein the compound comprises 1 to 10 mol % of the composition.

One aspect of the present disclosure is directed to a lipid nanoparticle and/or a lipid nanoparticle formulation. The lipid nanoparticle and/or a lipid nanoparticle formulation comprises a membrane defining an inner space, wherein the membrane is formed with a plurality of lipid components comprising the compound of the present disclosure.

One aspect of the present disclosure is directed to a bi-functional targeting nanocarrier composition/formulation, which comprises the lipid nanoparticle of the present disclosure.

One aspect of the present disclosure is directed to a kit and/or a reagent mixture for preparing a lipid nanoparticle, comprising a first reagent, comprising the compound of the present disclosure; and a second reagent, comprising an ionizable lipid, a helper lipid, or a mixture thereof.

One aspect of the present disclosure is directed to a method of targeted payload delivery in a subject in need thereof, comprising administering to the subject an effective amount of the targeting lipid nanoparticle of the present disclosure in a pharmaceutically acceptable formulation, wherein the payload is a nucleic acid, a compound, a polypeptide, a protein, a glycan, or a combination thereof, and the payload is encapsulated by the lipid nanoparticle.

One aspect of the present disclosure is directed to a method of preventing or treating a disease in a subject in need thereof, comprising administering to the subject an effective amount of the targeting lipid nanoparticle of the present disclosure in a pharmaceutically acceptable formulation, wherein the payload is a nucleic acid, a compound, a polypeptide, a protein, a glycan, or a combination thereof, and the payload is encapsulated within the lipid nanoparticle; and wherein the payload is a therapeutic agent or derives a therapeutic agent.

One aspect of the present disclosure is directed to a method of boosting an adaptive immune response, comprising administering to the subject an effective amount of the targeting lipid nanoparticle of the present disclosure in a pharmaceutically acceptable formulation, wherein the payload is a nucleic acid, a compound, a polypeptide, a protein, a glycan, or a combination thereof, and the payload is encapsulated within the lipid nanoparticle; and wherein the payload is immunogenic or derives an immunogenic biomolecule.

In certain embodiments of the bi-functional molecule and formulations thereof, Formula 1 can be structural and/or functional analogs/mimetics with cell-targeting functionalities, and Formula 2 can be structural/functional analogs/mimetics with lipid membrane insertion/anchoring functionalities.

DETAILED DESCRIPTION OF THE INVENTION

Figure 1:
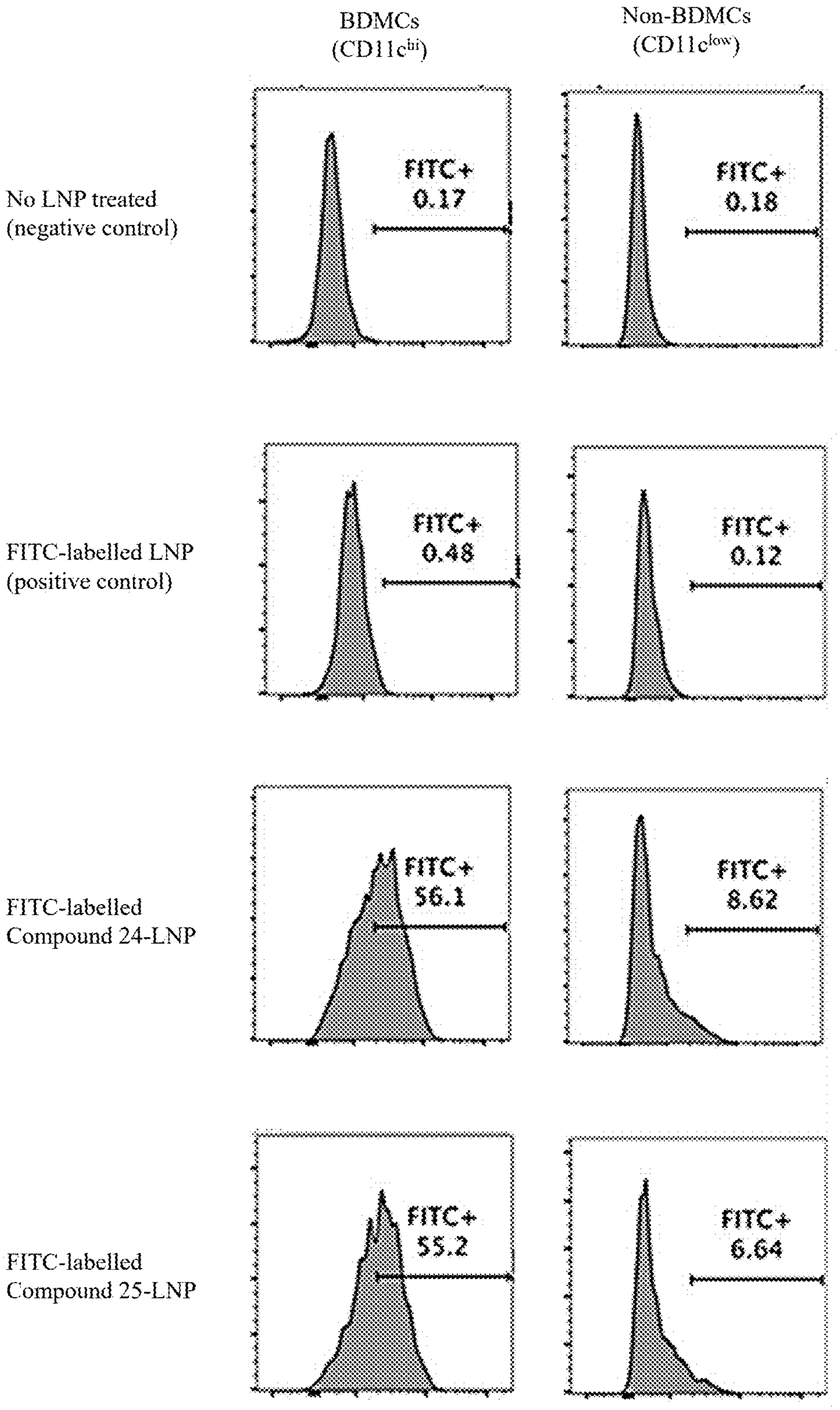
FIG. 1 provides a graphic representation of the FACS analysis results demonstrating the efficacy of the exemplary inventive embodiments. The experiments demonstrated the uptake of the novel nano-delivery formulations targeting BDMCs, according to embodiments of the present disclosure, compared to traditional LNPs. The FITC+ values shown in the figures are fluorescent intensities in arbitrary units (A.U.).

Nanoparticles have been widely used in various applications. Among them, lipid nanoparticles (e.g., liposomes) are the most well-established delivery systems for medicines due to their biocompatibility and biodegradability. A typical liposome has a bilayer structure formed by phospholipids due to their amphipathic properties. The bilayer structure (i.e., a bilayer membrane) encloses an inner space, which can encapsulate hydrophilic molecules, while the bilayer structure itself can carry hydrophobic molecules. Lipid nanoparticles (LNP) are also the most studied vehicles for delivering nucleic acids, such as RNA. By encapsulation, LNPs protect nucleic acids from extracellular nucleases, thus allowing for safe delivery to cells.

LNPs commonly have four kinds of lipid components in desired ratios: (i) helper lipid to encapsulate cargo, (ii) ionizable lipid to enhance endosomal escape and delivery, (iii) cholesterol to promote stability, and (iv) lipid-anchored polyethylene glycol (PEG-lipid) to reduce immune system recognition and improve biodistribution. Cholesterol and PEG-lipid can also be categorized as helper lipids. The properties of a liposome can be adjusted by selecting desired lipid components or ratios thereof. Without wishing to be bound by theories, targeting moieties can also be conjugated with the lipid components to provide selective delivery.

Targeting Lipid Compound

One aspect of the present disclosure provides a compound for forming a lipid nanoparticle (LNP) formulation suitable for specific cell targeting. In certain embodiments, the compound is a bi-functional compound containing a glycan-based cell-targeting moiety and a lipid moiety, which can be incorporated into a lipid bi-layer such as an LNP. In some embodiments, the bi-functional compound is designed to have a targeting moiety configured to provide selective delivery functionalities as part of the bi-functional molecule and to have an exemplary lipid tail moiety capable of being incorporated into the lipid bilayer membrane of an exemplary formulation, including a lipid nanoparticle. The compound of the present disclosure can have a dual-tail structure, which comprises two extended structures (e.g., $X_1$ and $X_2$ group below). At least one of the two extended structures is configured to be incorporated into a bilayer membrane of the formed lipid nanoparticle. The term "incorporated into a bilayer" herein describes that at least a portion of the extended structure is incorporated into the bilayer. In some embodiments, the entire extended structure is incorporated into the bilayer, but the term is not limited to the scenario.

In one exemplary aspect, the compound of the present disclosure comprises:

Formula 1

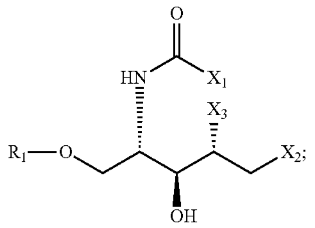

or

Formula 2

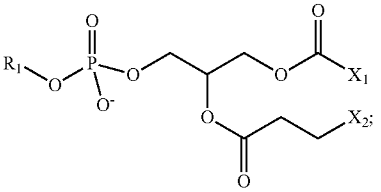

wherein $R_1$ comprises a substituted or non-substituted glycosyl group; wherein $X_1$ and $X_2$ are each independently hydrogen, alkyl, alkenyl, alkynyl, aryloxy, or a substituted version thereof, or —$(CH_2)nX_4$, n is 0 to 50, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N; and wherein $X_3$ is hydrogen, $C_{1-6}$ alkyl, or hydroxyl.

$R_1$ Group

Targeting Functionality. In certain embodiments, the $R_1$ group is configured to provide selective delivery or targeted delivery functionality for the exemplary LNP formulation formed by the component of the present disclosure. In some embodiments, the $R_1$ group is configured to target an antigen-presenting cell (e.g., a dendritic cell). In some embodiments, the target cell can be other types of immune cells. In yet some other embodiments, the target can be any biological cells where the payload is designed. In certain embodiments, the $R_1$ group is designed to have a targeting moiety, which can be a ligand of a receipt on a target cell. For example, the $R_1$ group might be configured to target the DC-SIGN of a dendritic cell.

Without wishing to be bound by theory, it is believed that mannoside and fucoside can bind a dendritic cell (e.g., via binding to DC-SIGN) with specificity. Therefore, in some embodiments, the $R_1$ group comprises a mannoside, fucoside, or both as the targeting moiety. The mannoside and/or the fucoside can be a terminal mannose or a terminal fucoside of the $R_1$ group, which might provide better chances to interact with a dendritic cell.

In some other embodiments, the $R_1$ group is configured to target Siglec-1, so the glycosyl group can comprise 9-N-(4H-thieno[3,2-c]chromene-2-carbamoyl)-Neu5Ac-α2,3-Gal-GlcNAc. In some embodiments, the $R_1$ group is configured to target Siglec-2, and the glycosyl group can comprise 9-Biphenyl Neu5Ac-α2,6-Gal-GlcNAc. In some embodiments, the $R_1$ group is configured to target Siglec-5/E, and the glycosyl group can comprise Neu5Ac-α2,3-Gal-GlcNAc.

In some embodiments, the $R_1$ group comprises a formula of $R_2$-$R_A$—, wherein $R_2$ is the substituted or non-substituted glycosyl group, and $R_A$ is an attachment group, and wherein the attachment group is an aryl, an alkyl, an amide, an alkyl amide, a combination thereof, or a covalent bond. In some embodiments, the aryl comprises 0 to 3 substituents (e.g., 1 to 3 substituents), wherein the substituent of the aryl is $C_{1-6}$ alkyl, halide, or $C_{1-6}$ alkyl halide. In some embodiments, the attachment group is configured to provide structural flexibilities and/or facilitate the binding between the targeting moiety and the target. In certain embodiments, $R_2$ is conjugated covalently to $R_A$ at a carbon of the glycosyl group, resulting in an O-glycosylation.

Binding in acidic conditions. In some embodiments, the binding between the glycosyl group of $R_1$ and a target is $Ca^{2+}$-correlated, and the calcium coordination might decrease at a low pH environment, resulting in lower binding affinity. Therefore, to provide a better binding affinity under acidic conditions, the attachment group can comprise an aryl group. Without wishing to be bound by any theories, the aryl group may engage in the CH-71 and hydrophobic interactions that enhance the binding under acidic conditions. The aryl group can be an unsubstituted benzene or a benzene substituted with a halide or an alkyl halide (e.g., a $CF_3$). In some embodiments, the aryl group is coupled with the targeting moiety. For example, the $R_1$ group can comprise an O-aryl mannoside.

Spacer. In some embodiments, the attachment group of $R_1$ comprises a spacer. The spacer is configured to provide structural flexibility to $R_1$. Without wishing to be bound by theories, the flexibility allows the glycosyl group of $R_1$ to move during the interaction between the targeting moiety and the target, thereby facilitating the binding between them.

In certain embodiments, a preferred spacer is biocompatible. In some embodiments, the initiator spacer comprises a saturated carbon moiety, a polyethylene glycol (PEG) moiety, or a combination thereof. For example, the spacer can be a polyethylene glycol (PEG) moiety, formed by 1, 2, 3, 4, 5, 6, 7, 8, 9, 10, 12, 15, 18, 20, 24, 30, 36, 40, 48, 50, 55, 60, 65, or 72 $(OCH_2CH_2)$ subunits, or any ranges defined by the foregoing endpoints, such as 2 to 72, 2 to 60, 2 to 48, 2 to 36, 2 to 24, 2 to 18, 2 to 15, 2 to 10, 4 to 72, 4 to 60, 4 to 48, 4 to 36, 4 to 24, 4 to 18, 4 to 15, 4 to 10, 8 to 72, 8 to 60, 8 to 48, 8 to 36, 8 to 24, 8 to 18, 8 to 15, or 8 to 10 $(OCH_2CH_2)$ subunits. In some embodiments, the PEG moiety can be a linear, branched, or star structure.

Structural configuration. In certain embodiments, the glycosyl group can be a linear structure or a branched structure. In some embodiments, the glycosyl group might have a plurality of targeting moieties, for example, 2, 3, 4, 5, 6, 7, 8, 9, or 10 targeting moieties. The plurality of targeting moieties can be arranged in a linear, branched, or star configuration. For example, the glycosyl group might comprise a mono-mannoside, a di-mannoside, or a tri-mannoside, and when the glycosyl group comprises a tri-mannoside, the tri-mannoside can be a linear form or a branched structure, such as a α-1,3-α-1,6-trimannoside. In certain embodiments, it is noticed that a branched configuration (e.g., a tri-mannoside glycan head) shows superior binding affinity to its target receptor.

In some embodiments, the $R_1$ group is a substituted glycosyl group. The glycosyl group might comprise 1 to 6 substituents, and each substituent can be $C_{1-6}$alkyl, $C_{1-6}$alkenyl, halogen, $C_{1-6}$ alkyl halide, $C_{1-6}$ alkoxy, amine, nitro, $C_{1-6}$ alkyl amine, amide, azido, aryl, cycloalkyl, heterocycloalkyl, sulfite, or a substituted version thereof, or a combination thereof. In certain embodiments, the substituent is conjugated to a carbon of the glycosyl group directly or is conjugated to the carbon via an O-yl conjugation (e.g., by replacing the hydrogen of the hydroxyl group on the carbon).

In certain embodiments, the substituent of the glycosyl group is selected from the group consisting of aryl, 5-membered cycloalkyl, 6-membered cycloalkyl, 5-membered heterocycloalkyl, and 6-membered heterocycloalkyl, and a substituted version thereof, which comprises 1 to 6 substituents selected from the group consisting of $C_{1-6}$ alkyl, halogen, $C_{1-6}$ alkyl halide, $C_{1-6}$ alkoxy, amine, nitro, $C_{1-6}$ alkyl amine, azido, amide, carboxyl, hydroxyl, aryl, cycloalkyl, heterocycloalkyl, or a substituted version thereof, or a combination thereof. In some embodiments, the heterocycloalkyl comprises 1 to 3 heteroatoms, selected from the group consisting of O, S, and N.

In some embodiments, the substituent of the glycosyl group is a substituted or non-substituted aryl, for example, a substituted or non-substituted phenyl group. In certain embodiments, the aryl is substituted with 1 to 6 substituents, each is independently selected from the group consisting of $C_1$. 6 alkyl, halogen, $C_{1-6}$ alkyl halide, $C_{1-6}$ alkoxy, amine, nitro, $C_{1-6}$ alkyl amine, azido, amide, carboxyl, hydroxyl, aryl, cycloalkyl, heterocycloalkyl, or a substituted version thereof, or a combination thereof. In certain embodiments, the substituent of the glycosyl group is a phenyl (benzene ring) substituted with OH, $CH_3$, $NH_2$, $CF_3$, $OCH_3$, F, Br, Cl, $NO_2$, $N_3$, or a combination thereof. For example, the substituted benzene ring can be a phenol group.

In some embodiments, the $R_1$ group is a mono-mannoside substituted with 1 to 6 substituents, and each substituent can be $C_{1-6}$ alkyl, $C_{1-6}$ alkenyl, halogen, $C_{1-6}$ alkyl halide, amine, $C_{1-6}$ alkyl amine, amide, aryl, cycloalkyl, heterocycloalkyl, sulfite, or a substituted version thereof, or a combination thereof. In certain embodiments, the $R_1$ group is a mono-mannoside substituted with a first substitute and a second substitute; each of the first substitute and the second substitute is independently selected from a group consisting of $C_{1-6}$alkyl, $C_{1-6}$ alkenyl, halogen, $C_{1-6}$alkyl halide, amine, $C_{1-6}$ alkyl amine, amide, aryl, cycloalkyl, heterocycloalkyl, and sulfite.

In some embodiments, the $R_1$ group comprises a first mannoside and a second mannoside. Each of the first mannoside and the second mannoside is independently substituted with 1 to 6 substituents, and each substituent can be $C_{1-6}$ alkyl, $C_{1-6}$ alkenyl, halogen, $C_{1-6}$ alkyl halide, amine, $C_{1-6}$ alkyl amine, amide, aryl, cycloalkyl, heterocycloalkyl, sulfite, or a substituted version thereof, or a combination thereof.

Binding affinity. In some embodiments, the binding affinity between the glycosyl group of $R_1$ and a target can be defined by a dissociation constant ($K_D$). In some embodiments, the $K_D$ at pH 7.4 can be 5, 10, 15, 20, 30, 40, 50, 75, 100, 125, 150, 200, 250, 300, 350, 400, 450, 500, 600, 700, 800, 900, 1000, 1250, 1500, 1750, 2000, 2250, 2500, 3000, 3250, 3500, 3750, 4000, 4250, 4500, 4750, 5000, 5250, 5500, 5750, 6000, 6250, 6500, 6750, 7000, 7250, 7500, 7750, or 8000 nM, or any range defined by the foregoing endpoints, such as, 5 to 8000, 5 to 7000, 5 to 6000, 5 to 5000, 5 to 4000, 5 to 3000, 5 to 2500, 5 to 2000, 5 to 1500, 5 to 1250, 5 to 1000, 5 to 900, 5 to 800, 5 to 700, 5 to 600, 5 to 500, 5 to 400, 5 to 300, 5 to 200, 5 to 150, 5 to 100, 5 to 75, 5 to 50, 5 to 30, 5 to 20, 10 to 8000, 10 to 7000, 10 to 6000, 10 to 5000, 10 to 4000, 10 to 3000, 10 to 2500, 10 to 2000, 10 to 1500, 10 to 1250, 10 to 1000, 10 to 900, 10 to 800, 10 to 700, 10 to 600, 10 to 500, 10 to 400, 10 to 300, 10 to 200, 10 to 150, 10 to 100, 10 to 75, 10 to 50, 10 to 30, or 10 to 20 nM.

In some other embodiments, the $K_D$ at pH 5 can be 1, 2, 3, 4, 5, 10, 15, 20, 30, 40, 50, 75, 100, 125, 150, 200, 250, 300, 350, 400, 450, 500, 550, 600, 650, 700, 750, 800, 850, 900, 1000, 1250, 1500, 1750, or 2000 nM, or any range defined by the foregoing endpoints, such as, 1 to 2000, 1 to 1500, 1 to 1000, 1 to 900, 1 to 800, 1 to 750, 1 to 700, 1 to 650, 1 to 600, 1 to 550, 1 to 500, 1 to 450, 1 to 400, 1 to 350, 1 to 300, 1 to 250, 1 to 200, 1 to 150, 1 to 100, 1 to 75, 1 to 50, 1 to 40, 1 to 30, 1 to 20, 1 to 10, or to 5, 5 to 2000, 5 to 1500, 5 to 1000, 5 to 900, 5 to 800, 5 to 750, 5 to 700, 5 to 650, 5 to 600, 5 to 550, 5 to 500, 5 to 450, 5 to 400, 5 to 350, 5 to 300, 5 to 250, 5 to 200, 5 to 150, 5 to 100, 5 to 75, 5 to 50, 5 to 40, 5 to 30, 5 to 20, 5 to 10 nM.

Examples. In some embodiments, the $R_1$ group is selected from the group consisting of (each structure shown below is independent from one another despite whether it is separated using a semicolon with an adjacent structure):

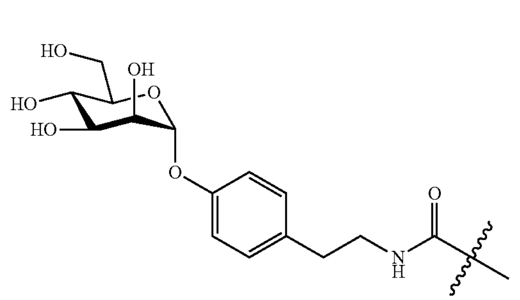

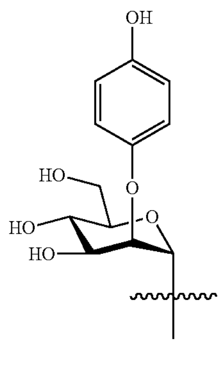

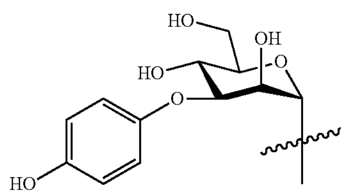

-continued
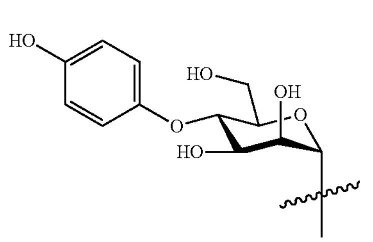
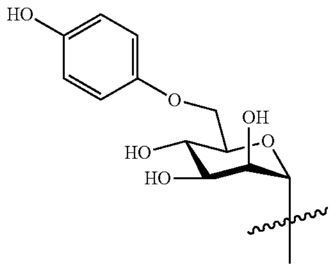
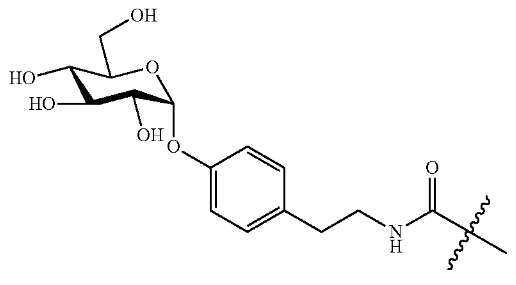
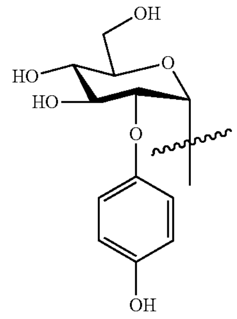
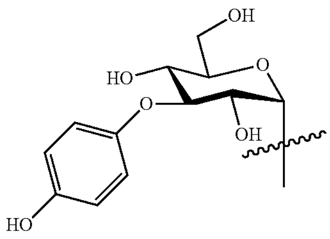
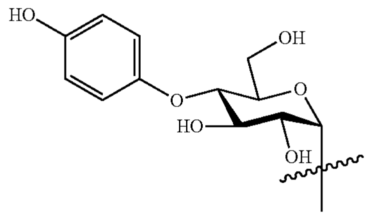
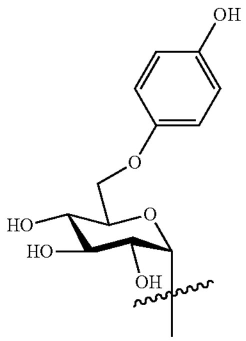
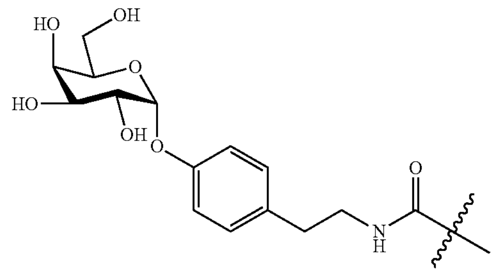
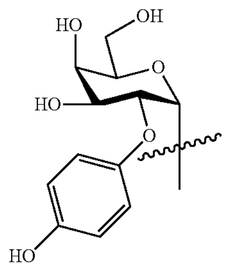
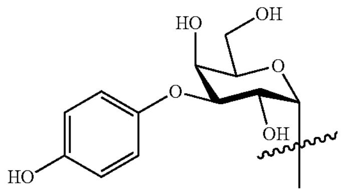
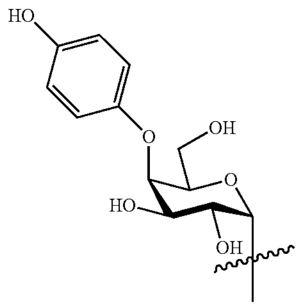
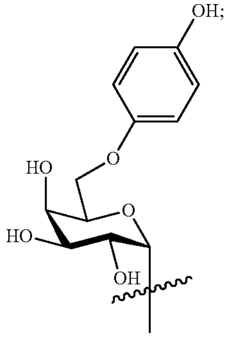
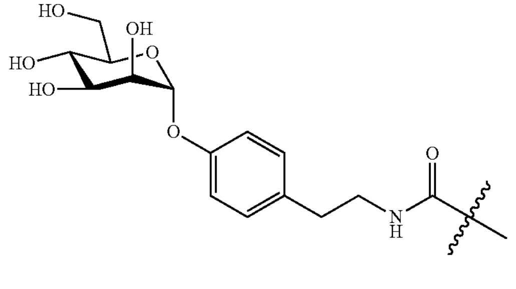
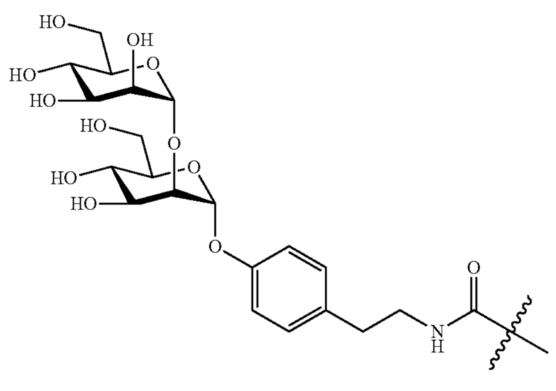

-continued
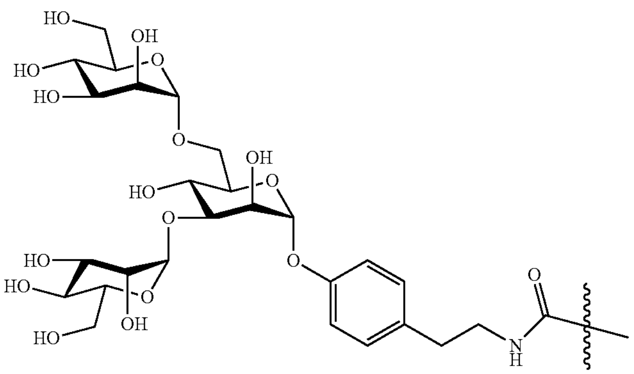
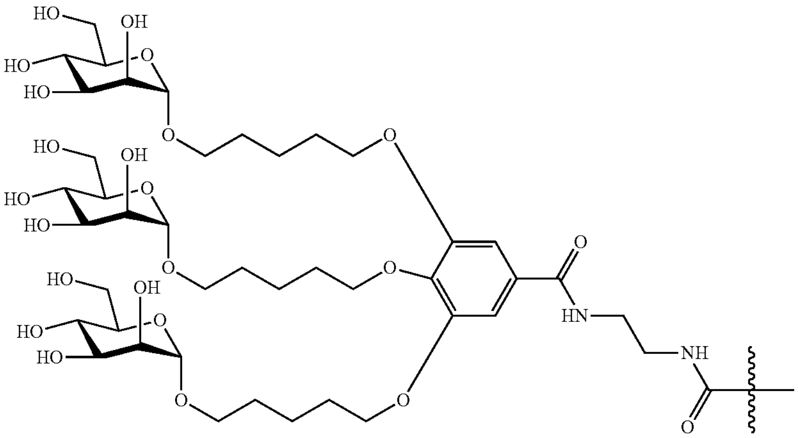
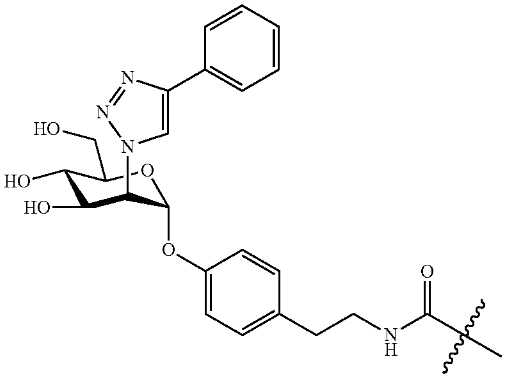
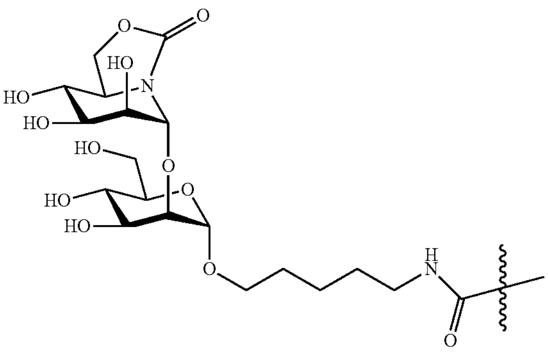

-continued
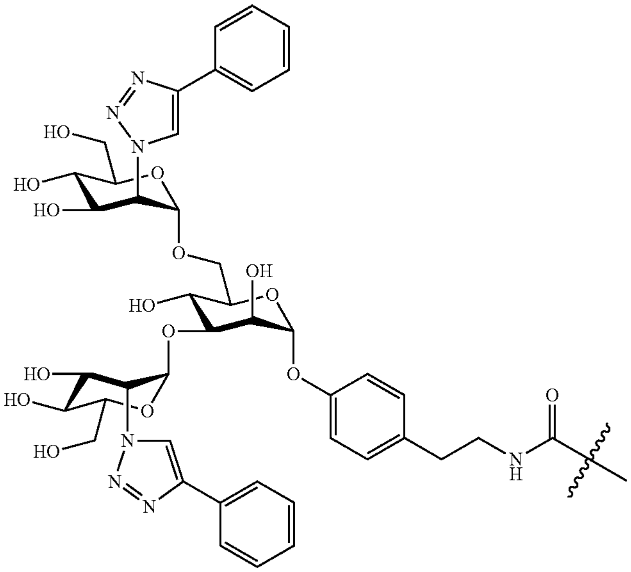
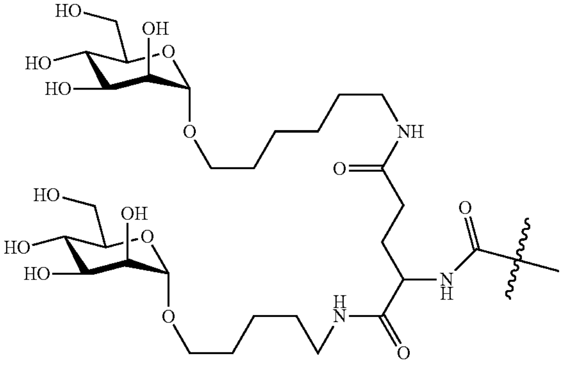
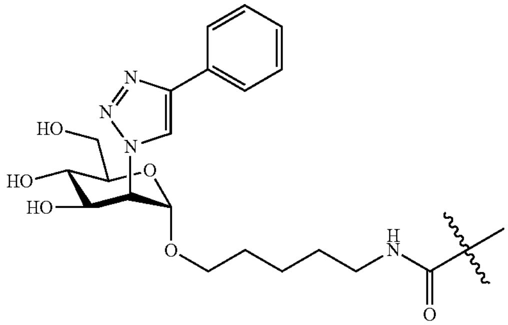
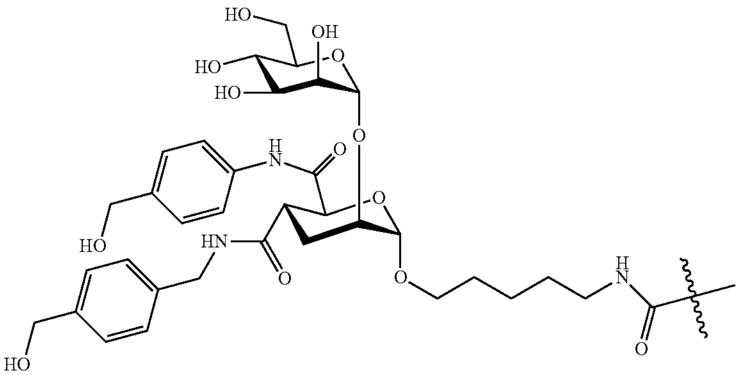

-continued
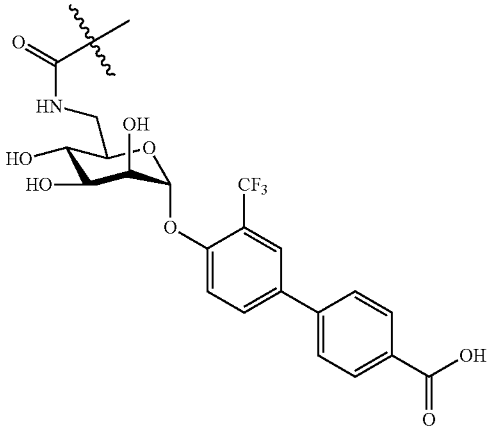
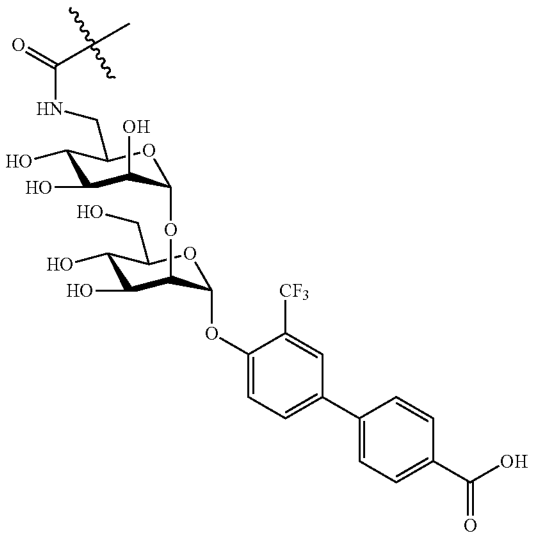
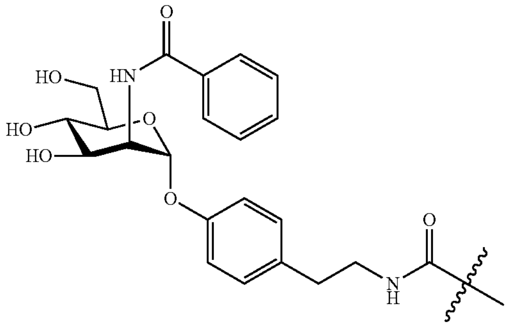
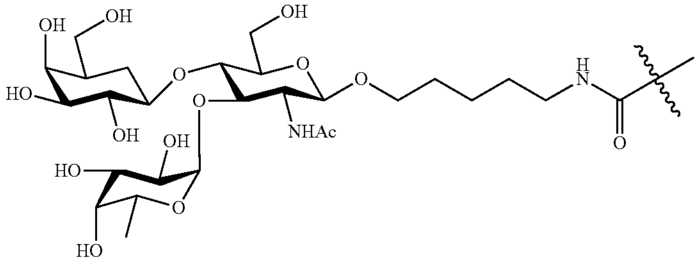
Lewis X
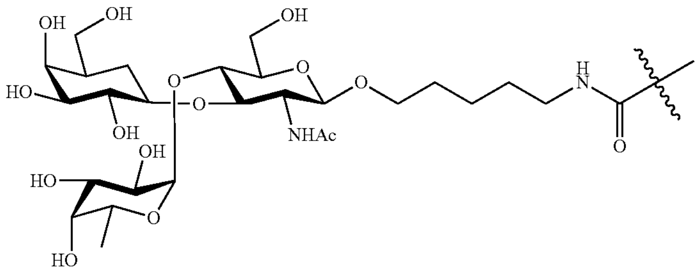
Lewis A -continued
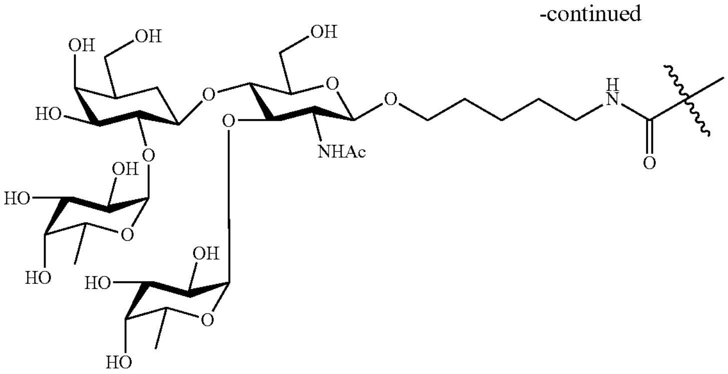
Lewis Y
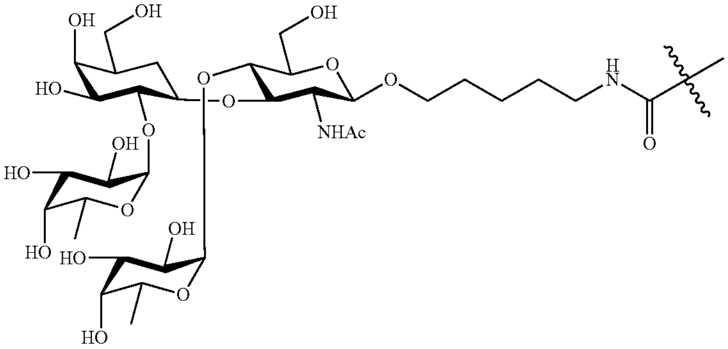
Lewis B
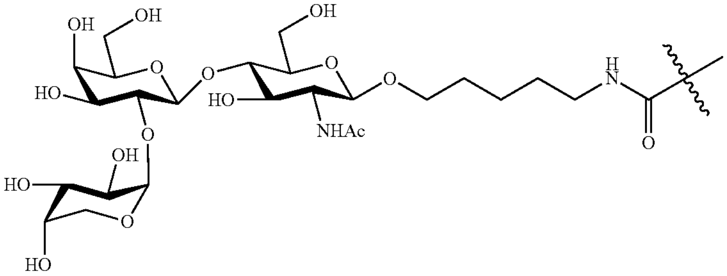
H type 2
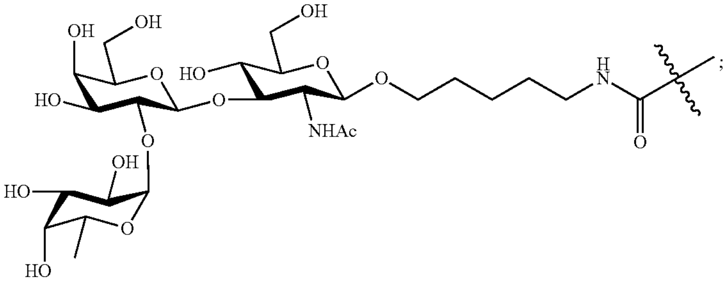
; and
H type 1
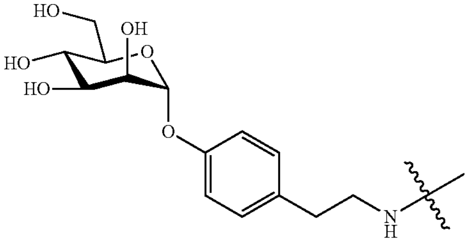
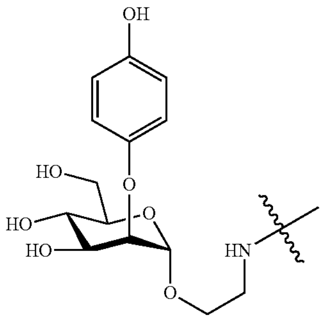

-continued
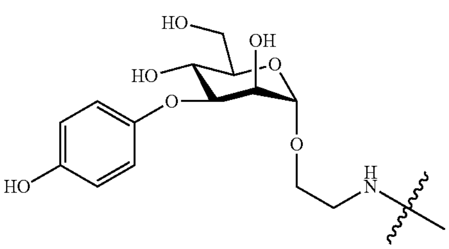
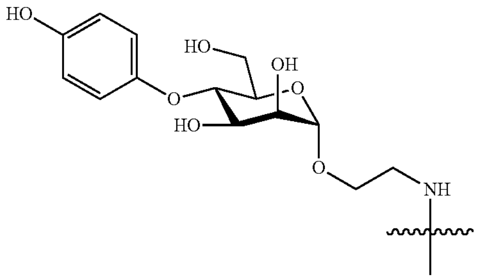
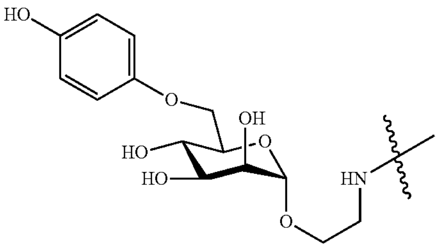
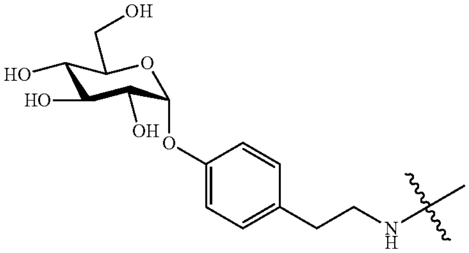
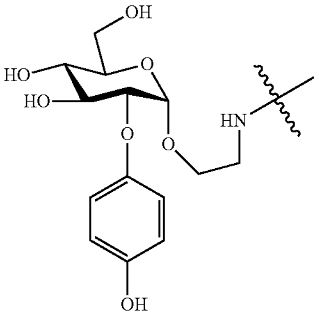
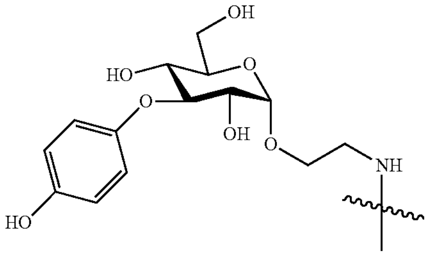
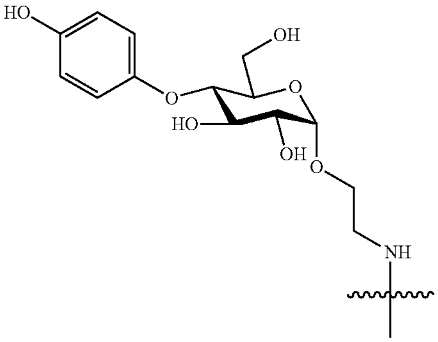
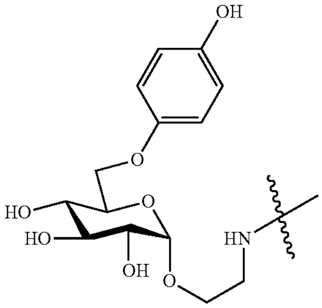
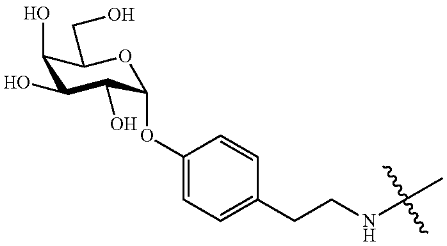
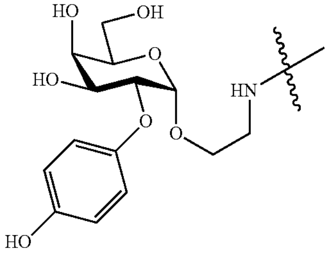

-continued
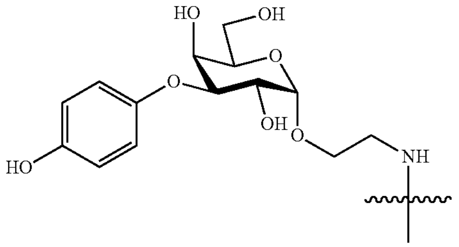
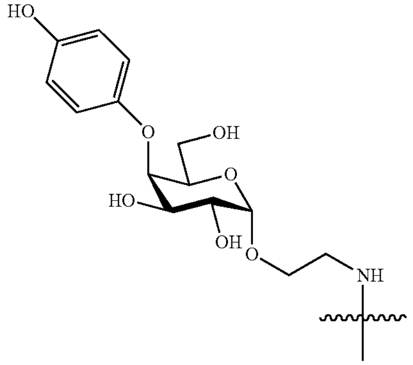
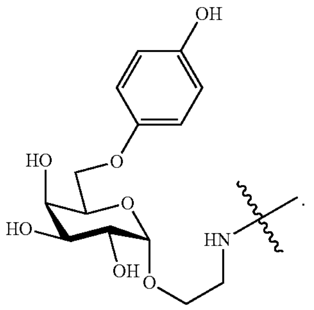
In some embodiments, the compound of the present disclosure has the structure shown in Formula 3:
Formula 3
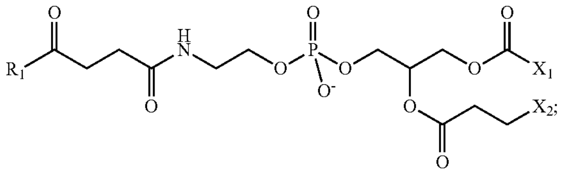
and
wherein the $R_1$ group is selected from the group consisting of (each structure shown below is independent from one another despite whether it is separated using a semicolon with an adjacent structure):
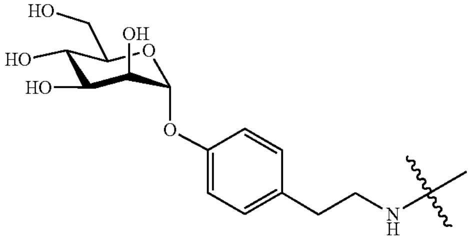
-continued
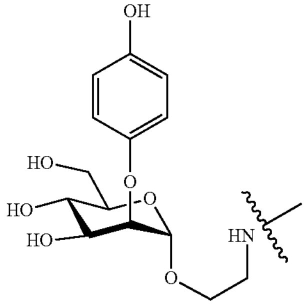
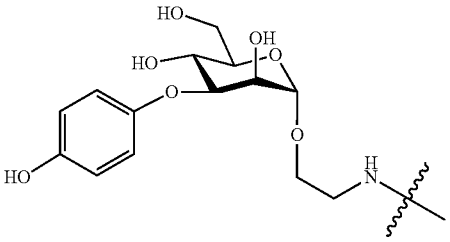
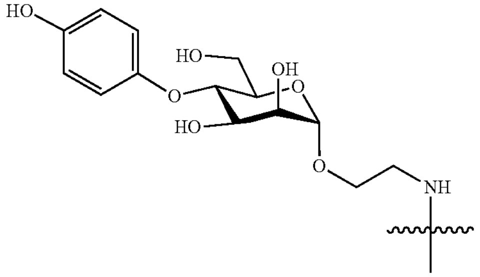

-continued

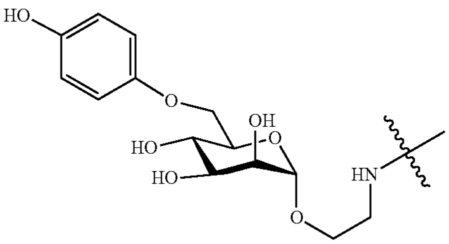

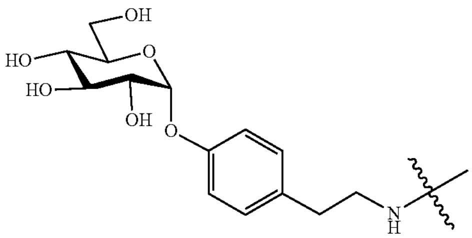

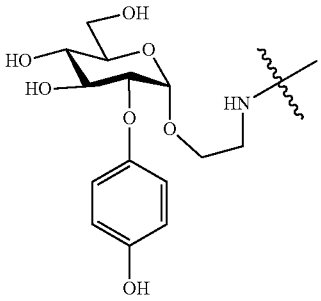

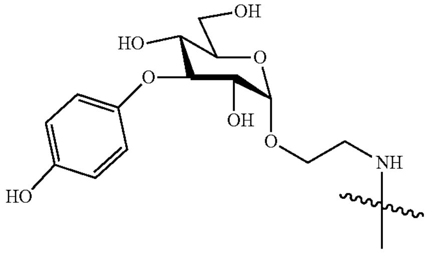

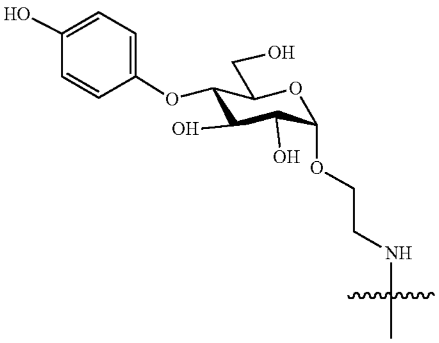

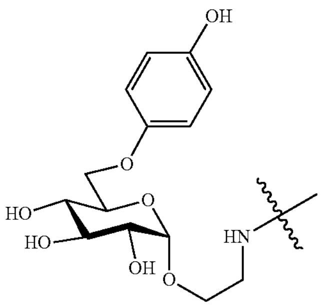

-continued

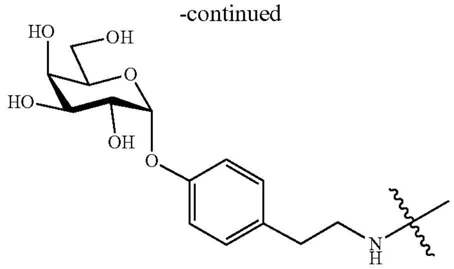

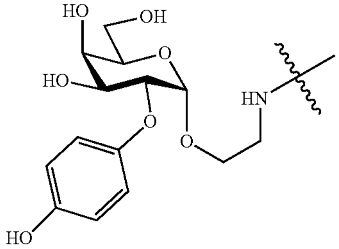

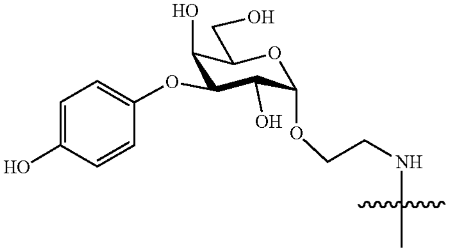

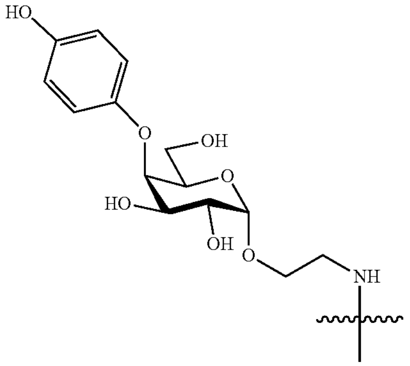

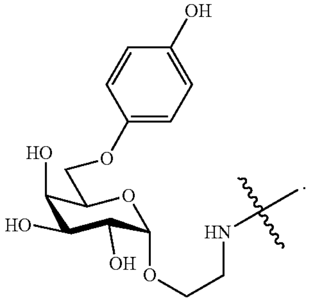

$X_1$ and $X_2$

The $X_1$ and $X_2$ are each independently hydrogen, $C_{1-30}$ alkyl, $C_{1-30}$ alkenyl, $C_{1-30}$ alkynyl, aryl, aryloxy, or a substituted version thereof, or —$(CH_2)nX_4$, n is 0 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof. Without wishing to be bound by theories, at least one of the $X_1$ and $X_2$ groups is designed to provide the compound of the present disclosure with desired hydrophobicity.

In some embodiments, at least one of the $X_1$ and $X_2$ comprises a saturated hydrocarbon chain, which comprises at least 2, 3, 4, 5, 6, 7, 8, 9, 10, 11, 12, 13, 14, 15, 16, 17, 18, 19, 20, 22, 24, 26, 28, or 30 carbons, or any range of carbons defined by the foregoing endpoints, such as 2 to 30, 2 to 28, 2 to 26, 2 to 24, 2 to 20, 2 to 18, 2 to 15, 2 to 12, 2 to 10, 2 to 8, 2 to 6, 2 to 4, 3 to 30, 3 to 28, 3 to 26, 3 to 24, 3 to 20, 3 to 18, 3 to 15, 3 to 14, 3 to 13, 3 to 12, 3 to 11, 3 to 10, 3 to 9, 3 to 8, 3 to 7, 3 to 6, 3 to 5, 4 to 30, 4 to 28, 4 to 26, 4 to 24, 4 to 20, 4 to 18, 4 to 15, 4 to 14, 4 to 13, 4 to 12, 4 to 11, 4 to 10, 4 to 9, 4 to 8, 4 to 7, 4 to 6, 6 to 15, 6 to 14, 6 to 13, 6 to 12, 6 to 11, 6 to 10, 6 to 9, 6 to 8, 10 to 30, 10 to 20, 15 to 30, 15 to 28, 15 to 26, or 15 to 20 carbons.

In some embodiments, $X_1$ and $X_2$ are each independently hydrogen, $C_{4-30}$ alkyl, $C_{4-30}$ alkenyl, $C_{4-30}$ alkynyl, aryl, aryloxy, or a substituted version thereof, or —$(CH_2)nX_4$, n is 4 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof.

In some embodiments, $X_1$ and $X_2$ are each independently hydrogen, $C_{8-30}$ alkyl, $C_{8-30}$ alkenyl, $C_{8-30}$ alkynyl, aryl, aryloxy, or a substituted version thereof, or —$(CH_2)nX_4$, n is 8 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof.

In some embodiments, when one of $X_1$ and $X_2$ is hydrogen, the other one is not hydrogen. In some embodiments, when one of $X_1$ and $X_2$ is hydrogen, the other one comprises a saturated hydrocarbon chain, comprising at least 2, 3, 4, 5, 6, 7, 8, 9, 10, 11, 12, 13, 14, 15, 16, 17, 18, 19, 20, 22, 24, 26, 28, or 30 carbons, or any range of carbons defined by the foregoing endpoints, such as 2 to 30, 2 to 28, 2 to 26, 2 to 24, 2 to 20, 2 to 18, 2 to 15, 2 to 12, 2 to 10, 2 to 8, 2 to 6, 2 to 4, 3 to 30, 3 to 28, 3 to 26, 3 to 24, 3 to 20, 3 to 18, 3 to 15, 3 to 14, 3 to 13, 3 to 12, 3 to 11, 3 to 10, 3 to 9, 3 to 8, 3 to 7, 3 to 6, 3 to 5, 4 to 30, 4 to 28, 4 to 26, 4 to 24, 4 to 20, 4 to 18, 4 to 15, 4 to 14, 4 to 13, 4 to 12, 4 to 11, 4 to 10, 4 to 9, 4 to 8, 4 to 7, 4 to 6, 6 to 15, 6 to 14, 6 to 13, 6 to 12, 6 to 11, 6 to 10, 6 to 9, 6 to 8, 10 to 30, 10 to 20, 15 to 30, 15 to 28, 15 to 26, or 15 to 20 carbons. In some embodiments, one of $X_1$ and $X_2$ is $C_{15-30}$ alkyl, and the other is —$(CH_2)nX_4$, as defined above.

In some embodiments, $X_4$ is an aryl, aryloxy, heterocyclic group, cycloalkyl, heterocycloalkyl, or a combination thereof, and wherein $X_4$ comprises 0 to 6 substituents, selected from the group consisting of $C_{1-6}$ alkyl, halogen, $C_{1-6}$ alkyl halogen, and $C_{1-6}$ alkoxy. In certain embodiments, $X_4$ comprises 1 to 3 substituents. The substituent can be, but is not limited to, $CH_3$, $CF_3$, F, or $OCH_3$.

In some embodiments, $X_4$ is —$R_3$—O—$R_4$, wherein $R_3$ and $R_4$ are each independently aryl, heterocyclic group, cycloalkyl, heterocycloalkyl, each comprising 0 to 6 substituents selected from the group consisting of $C_{1-6}$ alkyl, halogen, $C_{1-6}$ alkyl halogen, and $C_{1-6}$ alkoxy.

In certain embodiments, $X_4$ is selected from the group consisting of:

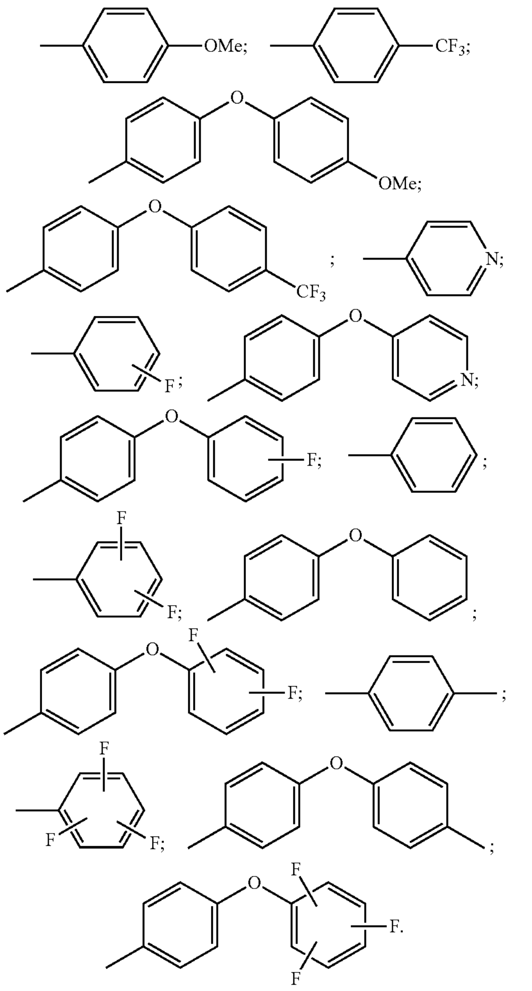

Exemplary Compound of the Present Disclosure

This section lists some exemplary structures of the compound of the present disclosure. However, the present disclosure is not limited to the exemplary structures listed below or in the specification. In some embodiments, the compound of the present disclosure does not comprise glycolipid C34 or α-galactosylceramide (α-GalCer).

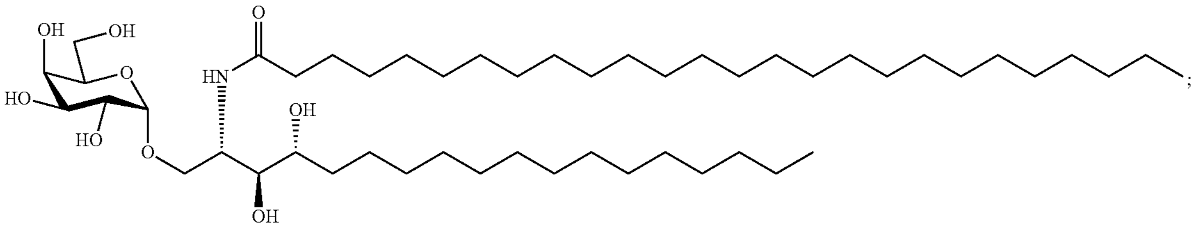
;

-continued
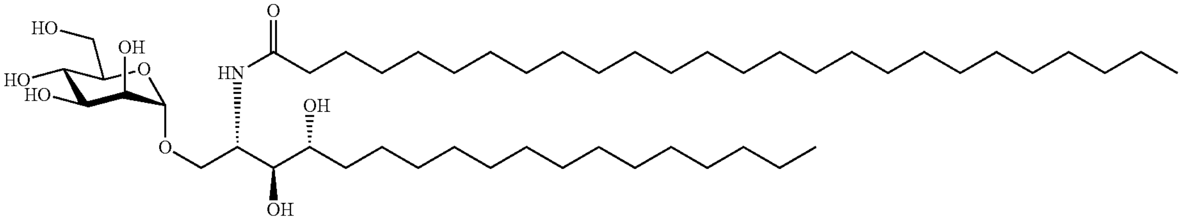
;
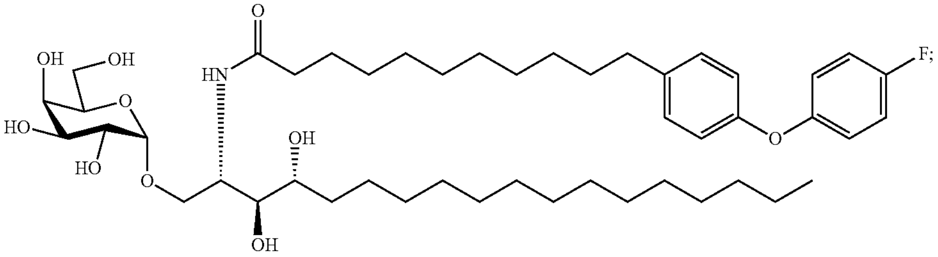
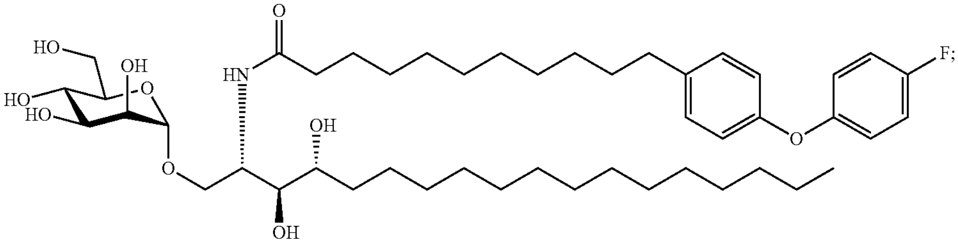
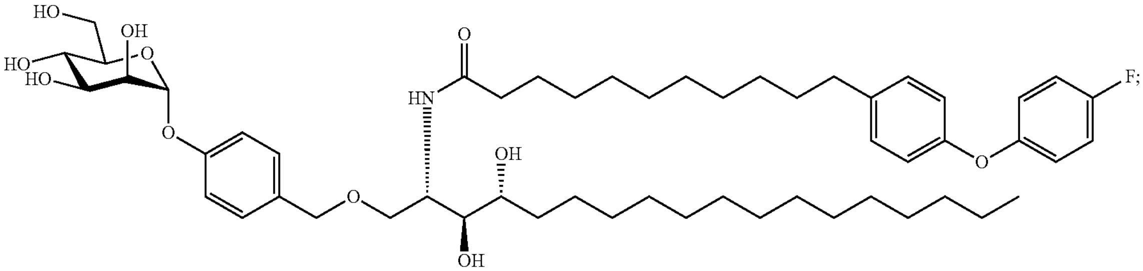
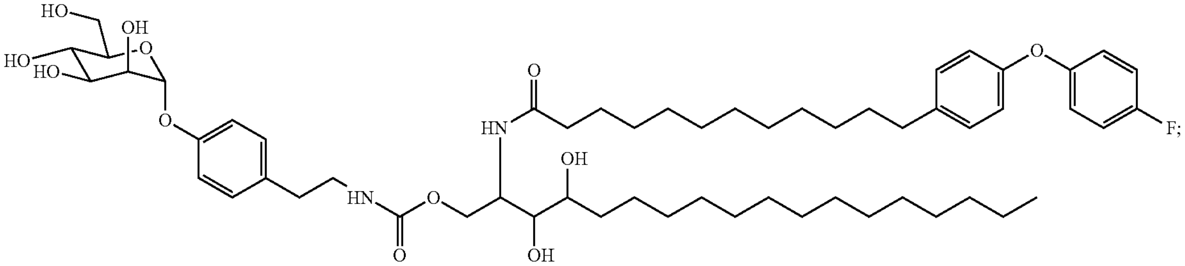
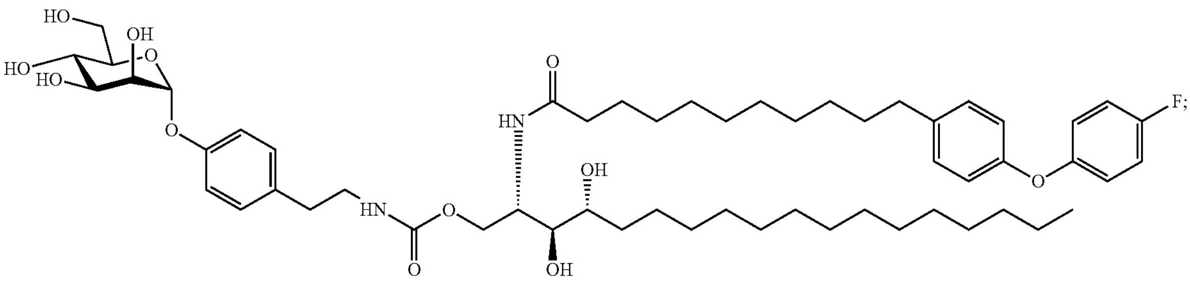

-continued
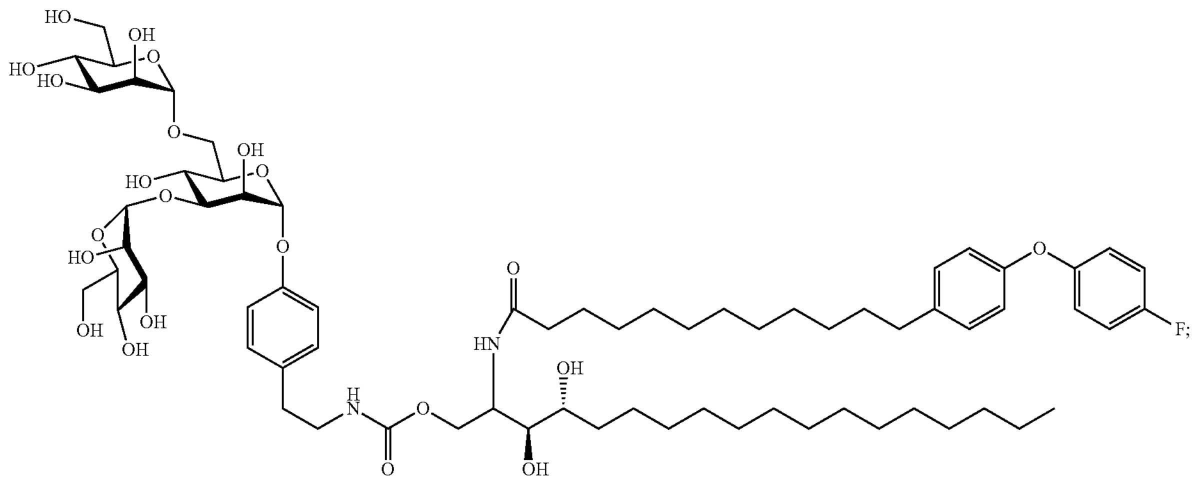
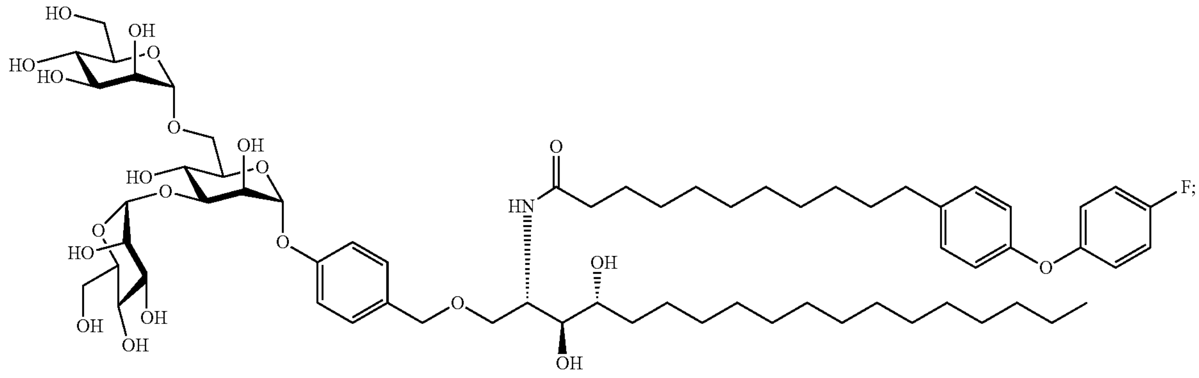
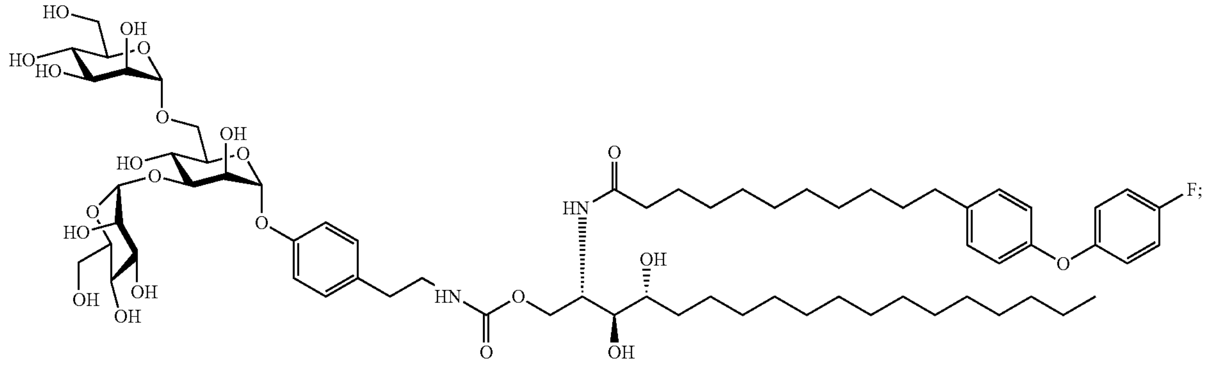
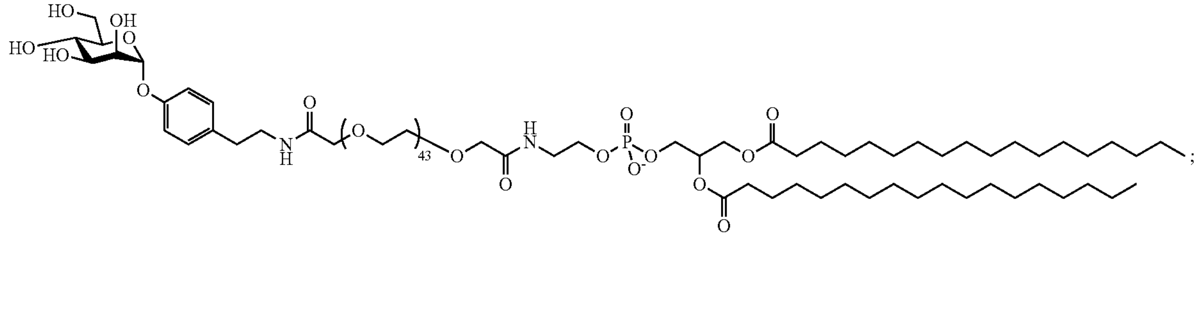

-continued

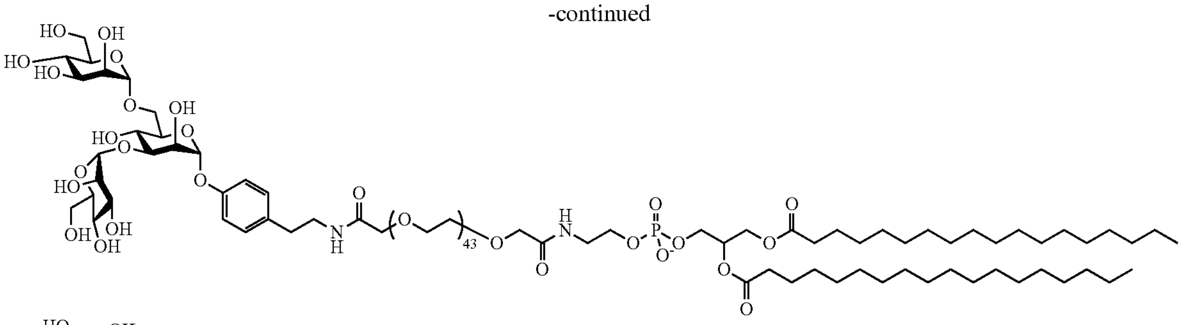

;

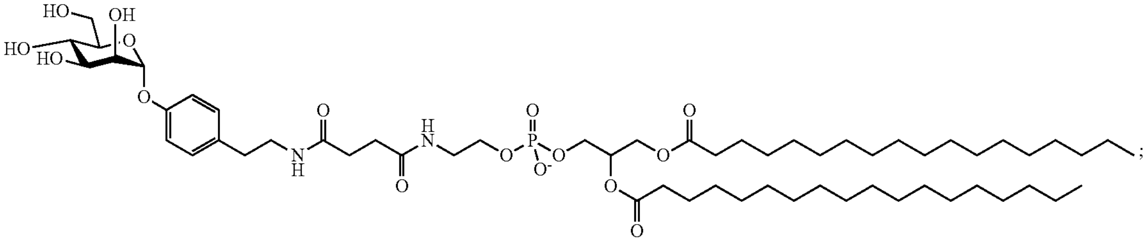

; and

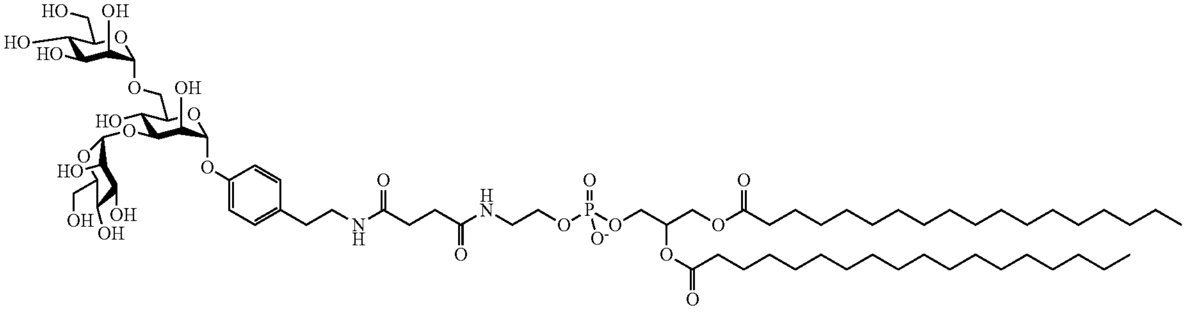

.

Composition for Forming a Lipid Nanoparticle

Another aspect of the present disclosure is directed to a composition, which comprises the compound of the present disclosure. In some embodiments, the compound comprises 1 to 10 mol % of the composition. In certain embodiments, the compound comprises about 1, 2, 3, 4, 5, 6, 7, 8, 9, or 10 mol % of the composition, or any range of carbons defined by the foregoing endpoints, such as 1 to 10 mol %, 1 to 9 mol %, 1 to 8 mol %, 1 to 7 mol %, 1 to 6 mol %, 1 to 5 mol %, 1 to 4 mol %, 1 to 3 mol %, 1 to 2 mol %, 2 to 10 mol %, 2 to 9 mol %, 2 to 8 mol %, 2 to 7 mol %, 2 to 6 mol %, 2 to 5 mol %, 2 to 4 mol %, 2 to 3 mol %, 3 to 10 mol %, 3 to 9 mol %, 3 to 8 mol %, 3 to 7 mol %, 3 to 6 mol %, 3 to 5 mol %, 3 to 4 mol %, 4 to 10 mol %, 4 to 9 mol %, 4 to 8 mol %, 4 to 7 mol %, 4 to 6 mol %, 4 to 5 mol %, 5 to 10 mol %, 5 to 9 mol %, 5 to 8 mol %, 5 to 7 mol %, or 5 to 6 mol % of the composition.

In some embodiments, the composition might comprise a first compound of the present disclosure and a second compound of the present disclosure. In some embodiments, the composition might comprise more than one, two, or three compounds, each is independently according to the compound of the present disclosure. The first compound, the second compound, or anyone, or any two of the more than one, two, or three compounds can be designed to have the same targeting moiety of the $R_1$ group, different targeting moiety of the $R_1$ group targeting the same target, or different targeting moiety of the $R_1$ group targeting different targets.

In some embodiments, the composition is configured to form a lipid nanoparticle. The lipid nanoparticle formed is, in some embodiments, expected to perform targeting delivery contributed by the compound of the present disclosure. In some embodiments, the composition configured to form a lipid nanoparticle might further comprise an ionizable lipid, a helper lipid, or a mixture thereof. In some embodiments, the ionizable lipid comprises 30 to 60 mol % of the composition, the helper lipid comprises 5 to 60 mol % of the composition, and the rest percent is a carrier or a solvent.

In some embodiments, the composition further comprises a payload (i.e., a cargo), which is further discussed below. In certain embodiments, the payload is a first payload, and the composition further encapsulates a second payload. The first payload and the second payload can be the same or different.

Ionizable Lipid.

In some embodiments, the ionizable lipid would be positively charged at a low pH environment. This feature facilitates the encapsulation of charged molecules, such as nucleic acid (e.g., RNA molecules), and endosomal escape, which allows the release of the cargo/payload into the cytoplasm efficiently. In some embodiments, the ionizable lipid would be neutral at a physiological pH environment, thereby reducing potential toxic effects for a living organism. In some embodiments, the ionizable lipid comprises 30 to 60 mol % of the composition. In certain embodiments, the ionizable lipid comprises about 30, 35, 40, 45, 50, 55, or 60 mol % of the composition, or any range of carbons defined by the foregoing endpoints, such as 30 to 60 mol %, 30 to 55 mol %, 30 to 50 mol %, 30 to 45 mol %, 30 to 40 mol %, 30 to 35 mol %, 35 to 60 mol %, 35 to 55 mol %, 35 to 50 mol %, 35 to 45 mol %, 35 to 40 mol %, 40 to 60 mol %, 40 to 55 mol %, 40 to 50 mol %, 40 to 45 mol %, 45 to 60 mol %, 45 to 55 mol %, 45 to 50 mol %, or 50 to 60 mol % of the composition. In some embodiments, the ionizable lipid comprises but not limited to heptadecan-9-yl 8-[2-hydroxyethyl-(6-oxo-6-undecoxyhexyl)amino]octanoate (SM-102™) (4 hydroxybutyl)azanediyl)bis(hexane-6,1-diyl)bis (2-hexyldecanoate) (ALC-0315™, Pfizer), or a combination thereof.

Helper Lipid.

A helper lipid is a lipid used to increase particle stability and fluidity of lipid nanoparticles. A help lipid can be but is not limited to phosphatidylcholine, cholesterol or a derivative thereof, a polyethylene glycol-lipid (PEG-lipid), or a mixture thereof. Without wishing to be bound by theories, phosphatidylcholine can help increase the bilayer stability of the lipid nanoparticle and can reduce non-specific binding; cholesterol can fill the gaps between the lipid components forming the lipid nanoparticles and thereby enhancing particle stability by modulating membrane integrity and rigidity; PEGylated lipids (PEG lipids) can enhance colloidal stability and circulation time of lipid nanoparticles in vivo.

In some embodiments, the helper lipid comprises 5 to 60 mol % of the composition. In certain embodiments, the helper lipid comprises about 5, 10, 15, 20, 25, 30, 35, 40, 45, 50, 55, and 60 mol % of the composition, or any range of carbons defined by the foregoing endpoints, such as 5 to 60 mol %, 5 to 55 mol %, 5 to 50 mol %, 5 to 45 mol %, 5 to 40 mol %, 5 to 35 mol %, 5 to 30 mol %, 5 to 25 mol %, 5 to 20 mol %, 5 to 15 mol %, 5 to 10 mol %, 10 to 60 mol %, 10 to 55 mol %, 10 to 50 mol %, 10 to 45 mol %, 10 to 40 mol %, 10 to 35 mol %, 10 to 30 mol %, 10 to 25 mol %, 10 to 20 mol %, 10 to 15 mol %,15 to 60 mol %, 15 to 55 mol %, 15 to 50 mol %, 15 to 45 mol %, 15 to 40 mol %, 15 to 35 mol %, 15 to 30 mol %, 15 to 25 mol %, 15 to 20 mol %, 20 to 60 mol %, 20 to 55 mol %, 20 to 50 mol %, 20 to 45 mol %, 20 to 40 mol %, 20 to 35 mol %, 20 to 30 mol %, 20 to 25 mol %, 25 to 60 mol %, 25 to 55 mol %, 25 to 50 mol %, 25 to 45 mol %, 25 to 40 mol %, 25 to 35 mol %, 25 to 30 mol %, 30 to 60 mol %, 30 to 55 mol %, 30 to 50 mol %, 30 to 45 mol %, 30 to 40 mol %, 30 to 35 mol %, 40 to 60 mol %, 40 to 55 mol %, 40 to 50 mol %, 40 to 45 mol %, 50 to 55 mol %, or 50 to 60 mol % of the composition.

Phosphatidylcholine. In some embodiments, the phosphatidylcholine comprises 5 to 10 mol % of the composition. In certain embodiments, the phosphatidylcholine comprises about 5, 6, 7, 8, 9, or 10 mol % of the composition, or any range of carbons defined by the foregoing endpoints, such as 5 to 10 mol %, 5 to 9 mol %, 5 to 8 mol %, 5 to 7 mol %, 5 to 6 mol %, 6 to 10 mol %, 6 to 9 mol %, 6 to 8 mol %, 6 to 7 mol %, 7 to 10 mol %, 7 to 9 mol %, 7 to 8 mol %, 8 to 10 mol %, 8 to 9 mol %, or 9 to 10 mol % of the composition. Examples of phosphatidylcholine include but are not limited to distearoylphosphatidylcholine (DSPC), dioleoylphosphatidylethanolamine (DPOE), or a mixture thereof.

Cholesterol. In some embodiments, the cholesterol or a derivative thereof comprises 30 to 40 mol % of the composition. In certain embodiments, the cholesterol or a derivative thereof comprises about 30, 32, 34, 36, 38, or 40 mol % of the composition, or any range of carbons defined by the foregoing endpoints, such as 30 to 40 mol %, 30 to 38 mol %, 30 to 36 mol %, 30 to 34 mol %, 30 to 32 mol %, 32 to 40 mol %, 32 to 38 mol %, 32 to 36 mol %, 32 to 34 mol %, 34 to 40 mol %, 34 to 38 mol %, 34 to 36 mol %, 36 to 40 mol %, 36 to 38 mol %, or 38 to 40 mol % of the composition. Examples of the the cholesterol or a derivative thereof includes but are not limited to cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (3β,5β)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

PEG-lipid. In some embodiments, the PEG-lipid comprises 1 to 10 mol % of the composition. In certain embodiments, the PEG-lipid comprises about 1, 2, 4, 6, 8, or 10 mol % of the composition, or any range of carbons defined by the foregoing endpoints, such as 1 to 10 mol %, 1 to 8 mol %, 1 to 6 mol %, 1 to 4 mol %, 1 to 2 mol %, 2 to 10 mol %, 2 to 8 mol %, 2 to 6 mol %, 2 to 4 mol %, 4 to 10 mol %, 4 to 8 mol %, 4 to 6 mol %, 6 to 10 mol %, 6 to 8 mol %, or 8 to 10 mol % of the composition. Examples of the PEG-lipid include but are not limited to DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof. In some embodiments, the function of a PEG-lipid in the composition/lipid nanoparticle can be provided by the compound of the present disclosure, especially by embodiments of the present disclosure where the attachment group of $R_1$ comprises a PEG moiety. In those circumstances, the composition does not need to comprise a PEG-lipid.

Examples. The table below lists some exemplary compositions according to the present disclosure. However, the present disclosure is not limited to the exemplary compositions or those described in the specification.

TABLE

Exemplary Embodiments of the Formulation of the Present Disclosure

| Embodiments | L1: Ionizable lipid | L2: Phosphatidylcholine | L3: Cholesterol | L4: PEG-Lipid | L5 the compound of the present disclosure |
|---|---|---|---|---|---|
| C1 (control) | SM-102 50 mol % | DSPC 10 mol % | Cholesterol 38.5 mol % | DMG-PEG2000 1.5 mol % | none |
| C2-1 | SM-102 45 mol % | DSPC 9 mol % | Cholesterol 34.65 mol % | DMG-PEG2000 1.35 mol % | Compound 22 10 mol % |
| C2-2 | SM-102 45 mol % | DSPC 9 mol % | Cholesterol 34.65 mol % | DMG-PEG2000 1.35 mol % | Compound 23 10 mol % |

TABLE-continued

Exemplary Embodiments of the Formulation of the Present Disclosure

| Embodiments | L1: Ionizable lipid | L2: Phosphatidylcholine | L3: Cholesterol | L4: PEG-Lipid | L5 the compound of the present disclosure |
|---|---|---|---|---|---|
| C2-3 | SM-102 45 mol % | DSPC 9 mol % | Cholesterol 34.65 mol % | DMG-PEG2000 1.35 mol % | Compound 24 10 mol % |
| C2-4 | SM-102 45 mol % | DSPC 9 mol % | Cholesterol 34.65 mol % | DMG-PEG2000 1.35 mol % | Compound 25 10 mol % |
| C2-5 | SM-102 45 mol % | DSPC 9 mol % | Cholesterol 34.65 mol % | DMG-PEG2000 1.35 mol % | Compound 22 + Compound 23 10 mol % |
| C2-6 | SM-102 45 mol % | DSPC 9 mol % | Cholesterol 34.65 mol % | DMG-PEG2000 1.35 mol % | Compound 24 + Compound 25 10 mol % |
| C2-7 | ALC-0315 45 mol % | DSPC 9 mol % | Cholesterol 34.65 mol % | DMG-PEG2000 1.35 mol % | Compound 22 10 mol % |
| C2-8 | ALC-0315 45 mol % | DSPC 9 mol % | Cholesterol 34.65 mol % | DMG-PEG2000 1.35 mol % | Compound 24 10 mol % |
| C3-1 | SM-102 47.5 mol % | DSPC 9.5 mol % | Cholesterol 36.5 mol % | DMG-PEG2000 1.5 mol % | Compound 22 5 mol % |
| C3-2 | SM-102 47.5 mol % | DSPC 9.5 mol % | Cholesterol 36.5 mol % | DMG-PEG2000 1.5 mol % | Compound 23 5 mol % |
| C3-3 | SM-102 47.5 mol % | DSPC 9.5 mol % | Cholesterol 36.5 mol % | DMG-PEG2000 1.5 mol % | Compound 24 5 mol % |
| C3-4 | SM-102 47.5 mol % | DSPC 9.5 mol % | Cholesterol 36.5 mol % | DMG-PEG2000 1.5 mol % | Compound 25 5 mol % |
| C3-5 | ALC-0315 47.5 mol % | DSPC 9.5 mol % | Cholesterol 36.5 mol % | DMG-PEG2000 1.5 mol % | Compound 22 5 mol % |
| C3-6 | ALC-0315 47.5 mol % | DSPC 9.5 mol % | Cholesterol 36.5 mol % | DMG-PEG2000 1.5 mol % | Compound 24 5 mol % |
| C4-1 | SM-102 40 mol % | DSPC 8 mol % | Cholesterol 30.5 mol % | DMG-PEG2000 1.5 mol % | Compound 22 20 mol % |
| C4-2 | SM-102 40 mol % | DSPC 8 mol % | Cholesterol 30.5 mol % | DMG-PEG2000 1.5 mol % | Compound 23 20 mol % |
| C4-3 | SM-102 40 mol % | DSPC 8 mol % | Cholesterol 30.5 mol % | DMG-PEG2000 1.5 mol % | Compound 24 20 mol % |
| C4-4 | SM-102 40 mol % | DSPC 8 mol % | Cholesterol 30.5 mol % | DMG-PEG2000 1.5 mol % | Compound 25 20 mol % |
| C4-5 | SM-102 40 mol % | DSPC 8 mol % | Cholesterol 30.5 mol % | DMG-PEG2000 1.5 mol % | Compound 22 + Compound 23 20 mol % |
| C4-6 | SM-102 40 mol % | DSPC 8 mol % | Cholesterol 30.5 mol % | DMG-PEG2000 1.5 mol % | Compound 24 + Compound 25 20 mol % |
| C4-7 | ALC-0315 40 mol % | DSPC 8 mol % | Cholesterol 30.5 mol % | DMG-PEG2000 1.5 mol % | Compound 22 20 mol % |
| C4-8 | ALC-0315 40 mol % | DSPC 8 mol % | Cholesterol 30.5 mol % | DMG-PEG2000 1.5 mol % | Compound 23 20 mol % |
| C5-1 | SM-102 45 mol % | DSPC 9 mol % | Cholesterol 34.5 mol % | DMG-PEG2000 1.5 mol % | Compound 22 10 mol % |
| C5-2 | SM-102 45 mol % | DSPC 9 mol % | Cholesterol 34.5 mol % | DMG-PEG2000 1.5 mol % | Compound 23 10 mol % |
| C5-3 | SM-102 45 mol % | DSPC 9 mol % | Cholesterol 34.5 mol % | DMG-PEG2000 1.5 mol % | Compound 24 10 mol % |

TABLE-continued

Exemplary Embodiments of the Formulation of the Present Disclosure

| Embodiments | L1: Ionizable lipid | L2: Phosphatidylcholine | L3: Cholesterol | L4: PEG-Lipid | L5 the compound of the present disclosure |
|---|---|---|---|---|---|
| C5-4 | SM-102 45 mol % | DSPC 9 mol % | Cholesterol 34.5 mol % | DMG-PEG2000 1.5 mol % | Compound 25 10 mol % |
| C6-1 | SM-102 50 mol % | DSPC 10 mol % | Cholesterol 38.5 mol % | DMG-PEG2000 1.5 mol % | Compound 22 10 mol % |
| C6-2 | SM-102 50 mol % | DSPC 10 mol % | Cholesterol 38.5 mol % | DMG-PEG2000 1.5 mol % | Compound 23 10 mol % |
| C6-3 | SM-102 50 mol % | DSPC 10 mol % | Cholesterol 38.5 mol % | DMG-PEG2000 1.5 mol % | Compound 24 10 mol % |
| C6-4 | SM-102 50 mol % | DSPC 10 mol % | Cholesterol 38.5 mol % | DMG-PEG2000 1.5 mol % | Compound 25 10 mol % |
| C6-5 | SM-102 50 mol % | DSPC 10 mol % | Cholesterol 38.5 mol % | DMG-PEG2000 1.5 mol % | Compound 22 + Compound 23 10 mol % |
| C6-6 | SM-102 50 mol % | DSPC 10 mol % | Cholesterol 38.5 mol % | DMG-PEG2000 1.5 mol % | Compound 24 + Compound 25 10 mol % |
| C6-7 | ALC-0315 50 mol % | DSPC 10 mol % | Cholesterol 38.5 mol % | DMG-PEG2000 1.5 mol % | Compound 24 10 mol % |
| C6-8 | ALC-0315 50 mol % | DSPC 10 mol % | Cholesterol 38.5 mol % | DMG-PEG2000 1.5 mol % | Compound 25 10 mol % |

Lipid Nanoparticle (Lnp)

Another aspect of the present disclosure is related to a lipid nanoparticle (LNP). The lipid nanoparticle of the present disclosure comprises a membrane defining an inner space, wherein the membrane is formed with a plurality of lipid components comprising the compound of the present disclosure. The membrane of the lipid nanoparticle can be a bilayer structure, which can be a single bilayer structure or a multiple bilayer structure. In some embodiments, the plurality of lipid components can further comprise an ionizable lipid, a helper lipid, or a combination thereof. The ionizable lipid and the helper lipid can be those described above. Without wishing to be bound by theories, the membrane is formed via hydrophobic interaction between the plurality of the lipid components, while in some circumstances, there might be electrostatic interaction involved in the formation of the membrane. In some embodiments, the plurality of lipid components does not comprise glycolipid C34 or α-galactosylceramide (α-GalCer). In some embodiments, the plurality of lipid compounds comprises glycolipid C34 or α-galactosylceramide (α-GalCer), and the glycolipid C34 or α-galactosylceramide (α-GalCer) comprises less than about 100%, 90%, 80%, 70%, 60%, 50%, 40%, 30%, 25%, 20%, 15%, 10%, 5% molar ratio of the plurality of lipid compounds, or any range defined by the foregoing endpoints, such as 100% to 5%, 90% to 5%, 70% to 5%, 70% to 5%, 60% to 5%, 50% to 5%, 40% to 5%, 30% to 5%, 25% to 5%, 20% to 5%, 15% to 5%, 10% to 5%, 100% to 10%, 90% to 10%, 70% to 10%, 70% to 10%, 60% to 10%, 50% to 10%, 40% to 10%, 30% to 10%, 25% to 10%, 20% to 10%, or 15% to 10%.

In some embodiments, the plurality of lipid components of the LNP's membrane might comprise a first compound of the present disclosure and a second compound of the present disclosure. In some embodiments, the plurality of lipid components might comprise more than one, two, or three compounds, each is independently according to the compound of the present disclosure. The first compound, the second compound, or anyone, or any two of the more than one, two, or three compounds can be designed to have the same targeting moiety of the $R_1$ group, different targeting moiety of the $R_1$ group targeting the same target, or different targeting moiety of the $R_1$ group targeting different targets.

In some embodiments, the compound of the present disclosure comprises at least 0.1%, 0.5%, 1%, 2%, 3%, 4%, 5%10%, 15%, 20%, 25%, 30%, 35%, 40%, 45, 50%, 550% 60%, 65%, or 70%, of the plurality of lipid components forming the membrane of the LNP, or any range defined by the foregoing endpoints, such as 0.1% to 70%, 0.1% to 60%, 0.1% to 50%, 0.1% to 40%, 0.1% to 35%, 0.1% to 30%, 0.1% to 25%, 0.1% to 20%, 0.1% to 15%, 0.1% to 10%, 0.1% to 5%, 0.1% to 4%, 0.1% to 3%, 0.1% to 2%, 0.1% to 1%, 0.1% to 0.5%, 0.5% to 70%, 0.5% to 60%, 0.5% to 50%, 0.5% to 40%, 0.5% to 35%, 0.5% to 30%, 0.5% to 25%, 0.5% to 20%, 0.5% to 15%, 0.5% to 10%, 0.5% to 5%, 0.5% to 4%, 0.5% to 3%, 0.5% to 2%, 0.5% to 1%, 1% to 70%, 1% to 60%, 1% to 50%, 1% to 40%, 1% to 35%, 1% to 30%, 1% to 25%, 1% to 20%, 1% to 15%, 1% to 10%, 1% to 5%, 1% to 4%, 1% to 3%, 1% to 2%, 5% to 70%, 5% to 60%, 5% to 50%, 5% to 40%, 5% to 35%, 5% to 30%, 5% to 25%, 5% to 20%, 5% to 15%, 5% to 10%, 10% to 70%, 10% to 60%, 10% to 50%, 10% to 40%, 10% to 35%, 10% to 30%, 10% to 25%, 10% to 20%, 10 to 15%, 20% to 70%, 20% to 60%, 20% to 50%, 20% to 40%, 20% to 30%, 30% to 70%, 30% to 60%, 30% to 50%, 30% to 40%, 50% to 70%, 50% to 65%, 50% to 60%, 60% to 70%, or 60% to 65%.

Size of the LNP.

In some embodiments, the LNP of the present disclosure has a diameter of 0.01, 0.05, 0.1, 0.15, 0.2, 0.3, 0.4, 0.5, 0.6, 0.7, 0.8, 0.9, 1, 1.5, 2, 2.5, 3, 3.5, 4, 4.5, or 5 microns, or any range defined by the foregoing endpoints, such as 0.00 to 5, 0.01 to 4, 0.00 to 3, 0.01 to 2, 0.01 to 1, 0.01 to 0.8, 0.01 to 0.6, 0.01 to 0.4, 0.01 to 0.2, 0.01 to 0.1, 0.01 to 0.05, 0.01 to 0.01, 0.05 to 5, 0.05 to 4, 0.05 to 3, 0.05 to 2, 0.05 to 1, 0.05 to 0.8, 0.05 to 0.6, 0.05 to 0.4, 0.05 to 0.2, 0.05 to 0.1, 0.1 to 5, 0.1 to 4, 0.1 to 3, 0.1 to 2, 0.1 to 1, 0.1 to 0.8, 0.1 to 0.6, 0.1 to 0.4, 0.1 to 0.2, 0.5 to 5, 0.5 to 4, 0.5 to 3, 0.5 to 2, 0.5 to 1, 0.5 to 0.8, 1 to 5, 1 to 4, 1 to 3, or 1 to 2 microns. The size of the LNP can be determined by using, but not limited to, Dynamic Light Scattering (DLS). In some embodiments, the LNP of the present disclosure has a polydispersity index (PDI) of about 0.01, 0.05, 0.1, 0.2, 0.3, 0.4, 0.5, 0.6, 0.7, 0.8, 0.9, or 1, or any range defined by the foregoing endpoints, such as 0.01 to 1, 0.01 to 0.9, 0.01 to 0.8, 0.01 to 0.7, 0.01 to 0.6, 0.01 to 0.5, 0.01 to 0.4, 0.01 to 0.3, 0.01 to 0.2, 0.01 to 0.1, 0.01 to 0.05, 0.1 to 1, 0.1 to 0.9, 0.1 to 0.8, 0.1 to 0.7, 0.1 to 0.6, 0.1 to 0.5, 0.1 to 0.4, 0.1 to 0.3, or 0.1 to 0.2.

Zeta Potential and Molecular Weight.

Without wishing to be bound by theories, the zeta potential and molecular weight of an exemplary targeting LNP may affect the cellular uptake of the exemplary targeting LNP. In some embodiments, the exemplary targeting LNP of the present disclosure comprises a zeta potential of about −50, −40, −30, −20, −15, −10, −5, 0, +5, +10, +15, +20, +30, +40, or +50, or any range defined by the foregoing endpoints, such as −50 to +50, −50 to +40, −50 to +30, −50 to +20, −50 to +15, −50 to +10, −50 to +5, −50 to −5, −50 to −10, −50 to −15, −50 to −20, −20 to +50, −20 to +40, −20 to +30, −20 to +20, −20 to +15, −20 to +10, −20 to +5, −20 to −5, −20 to −10, −20 to −15, −15 to +50, −15 to +40, −15 to +30, −15 to +20, −15 to +15, −15 to +10, −15 to +5, −15 to −5, −15 to −10, +5 to +50, +5 to +40, +5 to +30, +5 to +20, +5 to +15, or +5 to +10. In some embodiments, the exemplary targeting LNP of the present disclosure comprises a molecular weight of about 1, 2, 3, 4, 5, 6, 7, 8, 10, 12, 15, 20, 25, 30, 35, 40, 45, 50 kDa, or any range defined by the foregoing endpoints, such as 1 to 50 kDa, 1 to 40 kDa, 1 to 30 kDa, 1 to 20 kDa, 1 to 15 kDa, 1 to 10 kDa, 1 to 5 kDa, 2 to 50 kDa, 2 to 40 kDa, 2 to 30 kDa, 2 to 20 kDa, 2 to 15 kDa, 2 to 10 kDa, 2 to 5 kDa, 5 to 50 kDa, 5 to 40 kDa, 5 to 30 kDa, 5 to 20 kDa, 5 to 15 kDa, 5 to 10 kDa, 8 to 50 kDa, 8 to 45 kDa, 8 to 40 kDa, 8 to 35 kDa, 8 to 30 kDa, 8 to 25 kDa, 8 to 20 kDa, 8 to 15 kDa, 8 to 10 kDa, 12 to 50 kDa, 12 to 45 kDa, 12 to 35 kDa, 12 to 25 kDa, 12 to 15 kDa, 25 to 50 kDa, 25 to 40 kDa, or 25 to 30 kDa.

Payload

In some embodiments, the membrane of the LNP defines an inner space configured to encapsulate or carry a payload (i.e., a cargo). As described herein, "encapsulate a payload" or "carry a payload" refers to the condition that the payload is retained within the LNP by the membrane thereof. The payload can be either contained within the inner space defined by the LNP or embedded within the membrane (e.g., embedded within the bilayer structure). The payload might be able to move freely within the inner space or be attached covalently or non-covalently to the membrane. The encapsulation can be substantial, complete, or partial and does not exclude the possibility that part of the payload might be exposed to the environment outside the LNP. In the embodiments of partial encapsulation, at least 1%, 5%, 10%, 20%, 30%, 40%, 50%, 60%, 70%, 80%, 90%, or 95% of the payload is retained, enclosed, or surrounded by the membrane of the LNP. In some embodiments, the payload can be a biomolecule such as a nucleic acid, a compound, a polypeptide, a protein, a glycan head, or a combination thereof.

In some embodiments, the payload is a ribonucleic acid (RNA, e.g., an mRNA) or deoxyribonucleic acid (DNA, e.g., a double-strand DNA or a single-strand DNA), which, after being delivered by using the LNP of the present disclosure to a target cell, can encode a polypeptide or a protein in vivo. Nucleic acid, such as a mRNA molecule used in the present disclosure, can be prepared by in vitro transcription from a reference nucleic acid. The in vitro transcription can be performed as described in the PCT patent publication WO2014/152027, filed on Mar. 13, 2014, which is incorporated by reference in its entirety.

In some embodiments, the polypeptide or the protein is immunogenic (e.g., antigenic) to an organism to which the exemplary targeting LNP is administered. In such embodiments, the exemplary targeting LNP of the present disclosure is used to encapsulate and carry an immunogenic protein or a nucleic acid configured to encode the immunogenic protein in vivo, such as an mRNA molecule in an RNA vaccine. The immunogenic protein can be a protein of a pathogen of viral (e.g., Severe Acute Respiratory Syndrome Coronavirus (SARS-CoV, including SARS-CoV-2), influenza (flu), respiratory syncytial virus (RSV), EBV, DENGUE, VZV, HIV, ZIKA, or NIPAH), bacterial, or fungal origin. In some embodiments, an immunogenic protein can be a spike protein of a virus. In certain embodiments, the spike protein can be of coronavirus (CoV) origin, such as SARS-CoV, MERS-CoV, and SARS-CoV-2. In some embodiments, examples of the coronavirus (CoV) described herein include but are not limited to, alpha-SARS-CoV2, beta-SARS-CoV2, gamma-SARS-CoV2, delta-SARS-CoV2, omicron-SARS-CoV2, and variants thereof.

In some embodiments, the payload is a nucleic acid, which can be a polynucleotide having an open reading frame configured to encode a polypeptide or protein in vivo. Such a polynucleotide might be modified with a 5'terminal cap, which is generated during an in vitro-transcription reaction using the following chemical RNA cap analogs: 3"-O-Me-m7G(5)ppp(5') G [the ARCA cap], G(5)ppp(5')A, G(5')ppp(5')G, m7G(5')ppp(5')A, or m7G(5')ppp(5')G (New England BioLabs, Ipswich, Mass.). A 5'-capping of a modified polynucleotide may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-0 methyl-transferase to generate m7G(5')ppp(5')G-2'-O-methyl. Cap 2 structure may be generated from the Cap 1 structure followed by the 2'-O-methylation of the 5'-antepenultimate nucleotide using a 2'-0 methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source. After being transfected into mammalian cells, the modified polynucleotides have a stability of between 12-18 hours, or greater than 18 hours, e.g., 24, 36, 48, 60, 72, or greater than 72 hours.

In some embodiments, the nucleic acid might be modified. In some embodiments, the nucleic acid might have several (more than one) modifications, the same or different from each other. In some embodiments, the nucleic acid contains, in a particular region, one, two, or more (optionally different) nucleoside or nucleotide modifications. In some embodiments, a modified nucleic acid (e.g., a modified mRNA polynucleotide) exhibits reduced degradation in a cell or organism relative to unmodified ones. In some embodiments, a modified nucleic acid may exhibit reduced immunogenicity in an organism, respectively (e.g., a reduced innate response).

In some embodiments, the modification can comprise chemical modifications. In some embodiments, the modification can be naturally-occurring, non-naturally-occurring, or both. Some exemplary modifications useful in the present disclosure include but are not limited to, modifications of a sugar, a nucleobase, an internucleoside linkage (e.g., to a linking phosphate, to a phosphodiester linkage, or to the phosphodiester backbone), or a combination thereof. In some embodiments, the nucleic acid (e.g., RNA) used as a payload of the present disclosure can be codon optimized. For example, the nucleic acid can be modified to enhance the G/C content thereof. The G/C content of a nucleic acid may influence the stability thereof. A nucleic acid having an increased amount of guanine (G) and/or cytosine (C) residues may be functionally more stable than those containing a large amount of adenine (A) and thymine (T) or uracil (U) nucleotides. For example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid.

In some embodiments, the nucleic acid might further comprise a sequence encoding a signal peptide. The signal peptide might comprise three regions: (1) an N-terminal region of differing length, which usually comprises positively charged amino acids, (2) a hydrophobic region, and (3) a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. A signal peptide usually is not responsible for the final destination of the mature protein, but it is not limited in the present disclosure. Signal peptides are usually cleaved from precursor proteins by an endoplasmic reticulum (ER)-resident signal peptidase. They might remain uncleaved and function as a membrane anchor. In some embodiments, a signal peptide might be designed to fuse with the polypeptide or protein to be encoded by the payload at its C-terminus or N-terminus.

In some embodiments, the payload can be a therapeutic or prophylactic reagent for treating or preventing a disease (e.g., cancer or an infectious disease). For example, the payload can be an anti-viral agent, including but not limited to ribavirin, penciclovir, nitazoxanide, nafamostat, chloroquine, remdesivir (GS-5734) and favipiravir (T-705), interferon, adefovir, tenofovir, acyclovir, brivudin, cidofovir, fomivirsen, foscarnet, ganciclovir, amantadine, rimantadine, zanamivir, remdesivir, molnupiravir, and paxlovid. In other examples, the payload can be an anti-cancer agent. In certain embodiments, the payload is a nucleic acid configured to encode a therapeutic or prophylactic reagent.

In some embodiments, the N/P ratio (positively-chargeable amine (nitrogen atom of the ionizable lipid, N=nitrogen) groups to negatively-charged nucleic acid phosphate (P) groups) of the exemplary targeting LNP encapsulating a nucleic acid is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, or any range defined by the foregoing endpoints, include or exclude, such as 1 to 50, 1 to 40, 1 to 30, 1 to 20, 1 to 10, 1 to 5, 5 to 50, 5 to 40, 5 to 30, 5 to 20, 5 to 10, 10 to 50, 10 to 40, 10 to 30, 10 to 20, 8 to 40, 8 to 20, 8 to 12, 9 to 50, 9 to 30, or 9 to 15. In another embodiment, the exemplary targeting LNP encapsulating a mRNA has a nanoparticle/mRNA (N/P) ratio of about 10 or about 20.

In some embodiments where the payload of the LNP is a nucleic acid configured to encode a polypeptide or protein in a target cell, after uptake by the target cell, the LNP is configured to encode in vivo 1, 2, 3, 4, 5, 6, 7, 8, 9, 10, 15, 20, 25, 30, 35, 40, 45, or 50 copies of the polypeptide or protein, or any range defined by the foregoing endpoints, include or exclude, such as, 1 to 50, 1 to 40, 1 to 30, 1 to 20, 1 to 10, 1 to 5, 2 to 50, 2 to 40, 2 to 30, 2 to 20, 2 to 15, 2 to 10, 2 to 8, 2 to 6, 2 to 5, 2 to 4, 5 to 50, 5 to 40, 5 to 30, 5 to 20, 5 to 15, 5 to 10, 5 to 8, 4 to 50, 4 to 45, 4 to 35, 4 to 25, 4 to 15, 4 to 9, 4 to 6, 7 to 50, 7 to 45, 7 to 35, 7 to 25, 7 to 15, or 7 to 9 copies. In some embodiments, after uptake by the target cell, the LNP is configured to encode in vivo the polypeptide or protein continually and instantly until the nucleic acid (i.e., the payload) is deactivated in vivo.

Kit for Preparing a Lipid Nanoparticle.

One aspect of the present disclosure is directed to a kit/reagent mixture for preparing a targeting LNP formulation of the present disclosure. The kit comprises a first reagent and a second reagent, wherein the first reagent comprises the compound of the present disclosure, and the second reagent comprises an ionizable lipid, a helper lipid, or a mixture thereof. The ionizable lipid and the helper lipid can be those described herein. In some embodiments, the second reagent comprises the ionizable lipid, and in some embodiments, the kit further comprises a third reagent comprising the helper lipid. In some embodiments, the kit further comprises a fourth reagent comprising a payload, wherein the payload can be as those described herein.

Packaging. All the components of the kit of the present disclosure can be packaged in a physical container, respectively. In some embodiments, the first reagent and the second reagent are contained in the same container; in other words, in a ready-to-use package. In some other embodiments, the first reagent and the second reagent are contained in separate containers, so a user can decide whether and when to mix the first reagent and the second reagent.

Compositions/Formulations

One aspect of the present disclosure is directed to a composition comprising the LNP of the present disclosure. The LNP of the composition might encapsulate a payload and is configured to deliver the payload to a target region of an organism. The payload can be as described herein, comprising a nucleic acid, a compound, a peptide, a protein, a glycan head, or a combination thereof. In some embodiments, the payload can be an immunogenic protein or a nucleic acid configured to encode the immunogenic protein in vivo. In some embodiments, the formulation further comprises a pharmaceutically acceptable excipient, adjuvant, or a combination thereof. In certain embodiments, the composition is a pharmaceutical composition or pharmaceutical formulation.

In some embodiments, the composition comprises 0.01, 0.05, 0.1, 0.5, 1, 2, 3, 4, 5, 10, 15, 20, 25, 30, 40, 50, 60, 70, 80, 90, 95% (w/w) the LNP of the present disclosure, which encapsulates or does not encapsulate a payload, or any range defined by the foregoing endpoints, such as, included or excluded, 0.01% to 95% (w/w), 0.01% to 90% (w/w), 0.01% to 80% (w/w), 0.01% to 70% (w/w), 0.01% to 60% (w/w), 0.01% to 50% (w/w), 0.01% to 40% (w/w), 0.01% to 30% (w/w), 0.01% to 20% (w/w), 0.01% to 10% (w/w), 0.01% to 5% (w/w), 0.01% to 1% (w/w), 0.01% to 0.1% (w/w), 0.1% to 95% (w/w), 0.1% to 90% (w/w), 0.1% to 80% (w/w), 0.1% to 70% (w/w), 0.1% to 60% (w/w), 0.1% to 50% (w/w), 0.1% to 40% (w/w), 0.1% to 30% (w/w), 0.1% to 20% (w/w), 0.1% to 10% (w/w), 0.1% to 5% (w/w), 0.1% to 1% (w/w), 1% to 95% (w/w), 1% to 90% (w/w), 1% to 80% (w/w), 1% to 70% (w/w), 10% to 60% (w/w), 1% to 50% (w/w), 1% to 40% (w/w), 1% to 30% (w/w), 1% to 20% (w/w), 1% to 10% (w/w), 1% to 5% (w/w), 5% to 95% (w/w), 5% to 90% (w/w), 5% to 80% (w/w), 5% to 70% (w/w), 5% to 60% (w/w), 5% to 50% (w/w), 5% to 40% (w/w), 5% to 30% (w/w), 5% to 20% (w/w), or 5% to 10% (w/w). The rest of the percentages of the composition can be an excipient as described herein.

In some embodiments, the composition is an mRNA vaccine, wherein the LNP encapsulates an mRNA configured to encode an immunogenic protein in vivo. The immunogenic protein can be a virus spike protein or other antigenic molecule of a pathogen. In certain embodiments, the composition of the present invention can be a COVID-19 mRNA vaccine.

An exemplary COVID-19 mRNA vaccine, as described herein, can be designed based on an mRNA technology to remove the glycan shields of a coronavirus (e.g., SARS-CoV-2) spike protein for better exposing the conserved regions of the spike protein. The mRNA vaccine of coronavirus spike protein has a deletion of glycosylation sites in the receptor binding domain (RBD) or the subunit 2 (S2) domain to expose highly conserved epitopes and elicit antibodies and CD8 T-cell response with broader protection against the alpha, beta, gamma, delta, omicron and various variants, as compared to the unmodified mRNA. The vaccine can be a Low Sugar Universal Vaccine (LSUV) as described in WO2022/221835 (where the mRNA comprises a sequence selected from SEQ ID NO 1-52), WO2022/221837A2 (where the mRNA comprises a sequence selected from SEQ ID No 1-21) and US20200046826A1 (where the mRNA comprises a sequence selected from SEQ ID No 1-20), which are herein incorporated by reference in their entirety.

In some embodiments, the composition/formulation of the present invention is configured to treat or prevent a disease (e.g., cancer). In such embodiments, the payload carried by the LNP can be a therapeutic reagent, a prophylactic reagent, or a nucleic acid configured to encode the therapeutic reagent or the prophylactic reagent in vivo. For example, the composition can be a personalized cancer vaccine (e.g., melanoma), a KRAS vaccine (KRAS-driven), or a checkpoint vaccine (e.g., PD-1, PDL-1 related).

In some embodiments, the composition/formulation of the present invention can be administered together with another composition (e.g., a vaccine or a medicine). Examples of another composition can be but are not limited to, influenza (flu) vaccine, adenovirus vaccine, anthrax vaccine, cholera vaccine, diphtheria vaccine, hepatitis A or B vaccine, HPV vaccine, measles vaccine, mumps vaccine, smallpox vaccine, rotavirus vaccine, tuberculosis vaccine, pneumococcal vaccine, and *Haemophilus influenzae* type b vaccine.

Combination Compositions

In some embodiments, the composition can be a combination composition (e.g., a combo vaccine) comprising a first LNP encapsulating a first payload and a second LNP encapsulating a second payload. The first LNP and the second LNP can be as the LNPs described herein but are different from each other in terms of the structure or properties of the copolymers thereof. For example, wherein the first LNP and the second LNP are different in size, copolymers forming the membrane thereof, payload encapsulated within the LNP, or a combination thereof.

For example, the first LNP comprises a glycan head configured to bind DC-SIGN, while the second LNP comprises a glycan head configured to bind CD1d. In another example, the first LNP comprises a glycan configured to target an antigen-presenting cell, while the second LNP comprises a glycan configured to target a cancer cell.

In some embodiments, the first payload and the second payload are different from each other. For example, the first payload can be a protein or peptide, while the second payload can be a nucleic acid. In certain embodiments, the first payload and the second payload can both be mRNA molecules but encode different proteins. For example, the first payload can be a mRNA configured to encode a spike protein of delta-SARS-CoV2, while the second payload can be a mRNA configured to encode a spike protein of omicron-SARS-CoV2.

Additional Components of the Composition

In some embodiments, the composition of the present disclosure can further comprise an adjuvant and/or a non-active substance, such as a pharmaceutically acceptable excipient. In certain embodiments, the adjuvant can be but is not limited to C34, Gluco-C34, 7DW8-5, C17, C23, C30, α-galactosylceramide (α-GalCer), Aluminum salt (e.g., aluminum hydroxide, aluminum phosphate, alum (potassium aluminum sulfate), mixed aluminum salts), Squalene, MF59® (an oil-in-water emulsion comprising squalene, TWEEN 80®, and SPAN 85®), QS-21, Freund's complete adjuvant, Freund's incomplete adjuvant, AS03® (an oil-in-water emulsion comprising α-tocopherol, squalene and polysorbate 80), CpG 1018® (a synthetic, Toll-like receptor 9 (TLR9) agonist adjuvant), or a combination thereof.

In certain embodiments, the pharmaceutically acceptable excipient might comprise a solvent, dispersion media, diluent, dispersion, suspension aid, surface active agent, isotonic agent, thickening or emulsifying agent, preservative, polymer, peptide, protein, cell, hyaluronidase, or mixtures thereof. Various excipients for formulating pharmaceutical compositions and techniques for preparing the composition are known in the art (see Remington: The Science and Practice of Pharmacy, 22nd Edition, Edited by Allen, Loyd V., Jr, Pharmaceutical Press). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Formulation of standard pharmaceutically acceptable excipients may be carried out using routine methods in the pharmaceutical art (See Remington's Pharmaceutical Sciences, 19th Edition, Mack Publishing Company, Eastern Pennsylvania, USA.).

In some embodiments, the composition further comprises a phosphate conjugate. Without wishing to be bound by theories, the phosphate conjugate can increase in vivo circulation times and/or increase the targeted delivery of the LNP of the present disclosure. Phosphate conjugates for use with the present disclosure may be made using the methods described in the PCT Publication No. WO2013/033438, filed on Aug. 30, 2012, or U.S. Publication No. US2013/0196948, filed on Jun. 23, 2011, the content of each of which is herein incorporated by reference in its entirety. As a non-limiting example, the phosphate conjugates may include a compound of any one of the formulas described in the PCT Publication No. WO2013/033438, filed on Aug. 30, 2012, herein incorporated by reference in its entirety.

In some embodiments, the composition further comprises a conjugate to enhance the delivery of the LNP of the present disclosure. Without wishing to be bound by theories, the conjugate selected to be used may inhibit the phagocytic clearance of the LNP in a subject. In some examples, the conjugate may be a human membrane protein CD47 or a "self" peptide derived therefrom (e.g., the "self" particles described by Rodriguez et al. (Science 2013, 339, 971-975), herein incorporated by reference in its entirety).

In some embodiments where the payload is an immunogenic agent or a nucleic acid configured to encode the immunogenic agent, the composition further comprises an immunostimulatory agent to enhance the immune response induced by the immunogenic agent. As a non-limiting example, the composition may comprise a Th1 immunostimulatory agent, which may enhance a Th1-based response of the immune system (see PCT Publication No. WO2010/123569 and U.S. Publication No. 2011/0223201, each of which is herein incorporated by reference in its entirety).

In some embodiments, the composition does not include viral components (e.g., viral capsids, viral enzymes, or other viral proteins, for example, those needed for viral-based replication), nor is it packaged within, encapsulated within, linked to, or otherwise associated with a virus or viral particle.

Methods of Use

One aspect of the present disclosure is directed to methods of using the LNP or the targeting formulation of the present disclosure. Particularly, the methods are conducted to obtain a desired effect, such as targeted delivering a payload, preventing or treating a disease, or boosting an adaptive immune response in a subject. In some embodiments, the subject can be but not limited to an animal or a human, to whom the payload is designed to exhibit its efficacy, to whom the treatment or prevention of disease is needed, or to whom the adaptive immune response thereof is required to be boosted.

Methods of Targeted Payload Delivery in a Subject

In some embodiments, a method of targeted delivery of a payload in a subject is provided, which comprises administering an effective amount of the LNP to the subject or the targeting formulation of the present disclosure. The LNP and the payload are as described herein, and the payload is encapsulated by the LNP. Without wishing to be bound by any theories, the targeted delivery is fulfilled by the compound of the present disclosure. Particularly, the R1 group of the compound of the present disclosure provides the desired binding affinity/specificity targeting a desired region of the subject via the glycosyl group thereof.

Methods of Preventing or Treating a Disease in a Subject

In some embodiments, a method of preventing or treating a disease in a subject is provided, which comprises administering an effective amount of the LNP to the subject or the formulation of the present disclosure. The LNP of this method encapsulates a payload, and the payload is a therapeutic agent or derives a therapeutic agent configured to prevent and/or treat the disease.

Without wishing to be bound by any theories, the LNP or the formulation of the present disclosure provides targeted delivery via the compound of the present disclosure. Therefore, by using the LNP of the present disclosure to deliver the payload, the efficacy of the payload can be more effectively performed. For example, in the embodiments that the $R_1$ group of the compound comprises a structure binding specifically to the DC-SIGN on dendritic cells, an antigenic or immunogenic payload can be effectively delivered to the dendritic cells to provoke immune responses for preventing disease of concern. This strategy is beneficial in delivering an antigen or a nucleic acid encoding an antigen of a vaccine. Some other examples include having an $R_1$ group designed to target cancer cells so that an anti-tumor reagent can be delivered effectively to a cancer microenvironment. This strategy can increase the efficacy of the anti-tumor reagent and reduce the treatment's side effects.

In some embodiments, the disease is characterized by dysfunctional or aberrant protein or polypeptide activity. For example, the disease is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disease can be cancer or infectious diseases. In certain embodiments, the disease can be a viral-associated infection, including, but not limited to, human parainfluenza virus 3, respiratory syncytial virus (RSV), cytomegalovirus (CMV), human metapneumovirus (hMPV), or SARS-CoV-2 (COVID-19) associated infections.

Methods of Boosting an Adaptive Immune Response

In some embodiments, a method of boosting an adaptive immune response is provided, comprising administering an effective amount of the LNP of the present disclosure to a subject. The LNP of this method encapsulates a payload within an inner space defined by a membrane of the LNP, and the payload is a therapeutic agent or derives a therapeutic agent configured to provoke an adaptive immune response in the subject.

Without wishing to be bound by any theories, the LNP of the present disclosure provides targeted delivery to an immune cell via the compound of the present disclosure. In some embodiments, the $R_1$ group of the compound comprises a structure that binds to an antigen-presenting cell with the desired specificity or affinity. For example, the $R_1$ group might comprise a structure binding specifically to the DC-SIGN on dendritic cells so that the LNP is able to deliver the immunogenic payload specifically to the dendritic cells to facilitate the onset of an adaptive immune response.

In some embodiments, the boosted adaptive immune response is against a disease, including but not limited to cancer or an infectious disease. The infectious disease, for example, can be a viral-associated infection, including, but not limited to, human parainfluenza virus 3, respiratory syncytial virus (RSV), cytomegalovirus (CMV), human metapneumovirus (hMPV), or SARS-CoV-2 (COVID-19) associated infections.

Administration

Regarding the methods of the present disclosure, in some embodiments, the subject is administered with a single dose of the LNP or the targeting formulation of the present disclosure, which encapsulates or does not encapsulate a payload. Yet in some embodiments, the subject is administered with the LNP in an initial dose followed by at least one booster dose, e.g., one, two, three, four, five, six, seven, eight, nine, ten, eleven, twelve, thirteen, fourteen, fifteen, sixteen, seventeen, eighteen, nineteen, twenty, or more follow-up doses, with an interval of each dose in about, 1, 2, 3, 4, 5, 6, 7 days, about 1, 2, 3, 4, 5, 6, 7, 8, 9, or 10 weeks, or about 1, 2, 3, 4, 5, 6, 7, 8, 9, 10, 11, or 12 months, or any range defined by the foregoing endpoints, such as, included or excluded, 1 to 7 days, 1 to 5 days, 1 to 3 days, 1 to 10 weeks, 1 to 8 weeks, 1 to 6 weeks, 1 to 4 weeks, 1 to 2 weeks, 1 to 12 months, 1 to 8 months, 1 to 6 months, 1 to 4 months, 1 to 2 months, or 6 to 12 months. In certain embodiments, the LNP of the present disclosure encapsulating a payload is administered twice at the same or different doses, and the two administrations are separated by 1 day, 3 days, 5 days, 1 week, 2 weeks, 1 month, 2 months, 3 months, 6 months, 1 year, 1 to 5 days, 1 to 2 weeks, 1 to 3 months, 1 to 6 months, 1 month to 1 year, 3 months to 1 year, or 6 months to 1 year.

Administration route. The LNP or formulation as described herein may be administered by any route. Suitable routes include but are not limited to, oral, nasal, mucosal, submucosal, intravenous, intramuscular, intraperitoneal, subcutaneous, intradermal, transdermal, and buccal routes. Some practical topical applications include but are not limited to, a drop, spray, aerosol, gel, or ointment to the mucosal epithelium of the eye, nose, mouth, anus, or vagina. Other possible routes of administration are by spray, aerosol, or powder application through inhalation via the respiratory tract.

Effective amount of administration. The effective amount described herein refers to the amount sufficient to provide a desired effect. In the embodiments where the purpose of administering the LNP of the present disclosure is to treat a disease, the effective amount refers to a therapeutically effective amount, while in some other embodiments where the purpose is to prevent a disease, the effective amount refers to a prophylactically effective amount.

Yet in some other embodiments where the purpose of administering the LNP with payload is to boost an adaptive immune response, the effective amount can be determined as an amount sufficient to induce an antigen-specific immune response in a subject to whom the LNP and payload are administered. The antigen-specific immune response can be characterized by measuring an anti-antigenic polypeptide (i.e., the payload or the product of the payload) antibody titer produced in a subject to whom the LNP and payload are administered. In some embodiments, the measurement can be conducted using an Enzyme-linked immunosorbent assay (ELISA).

In some embodiments, an antibody titer is used to assess whether a subject has had an infection or to determine whether immunizations are required. In some embodiments, an antibody titer is used to determine the strength of an autoimmune response, to determine whether a booster immunization is needed or whether an immunization has been boosted, to determine whether a previous vaccine was effective, and/or to identify any recent or prior infections.

The effective amount of the methods of the present disclosure can be determined based on several factors, including but not limited to the conditions of the subjects (age, gender, species, body weight, health status, etc.), the progress of the disease to be treated, the administration route, the dosage and interval of the administration, and the nature of the payload. Regarding the nature of the payload, for example, in embodiments where the LNP of the present disclosure is used to carry an mRNA as in a mRNA vaccine, the effective amount can be determined based on the effective amount of the mRNA required to provoke sufficient immune response in the subject. Accordingly, in some embodiments that the payload is mRNA, the effective amount of the methods of the present disclosure is about 5, 10, 15, 20, 25, 30, 35, 40, 45, 50, 55, 60, 65, 70, 75, 80, 90, 100, 125, 150, 175, 200, 250, 300, 350, 400, 450, 500, 550, 600, 650, 700, 750, 800, 850, 900, 950 or 1000 micrograms (μg or ug), or any range defined by the foregoing endpoints, such as, include or exclude, 5 micrograms to 1000 micrograms, 5 micrograms to 900 micrograms, 5 micrograms to 800 micrograms, 5 micrograms to 700 micrograms, 5 micrograms to 600 micrograms, 5 micrograms to 500 micrograms, 5 micrograms to 400 micrograms, 5 micrograms to 300 micrograms, 5 micrograms to 200 micrograms, 5 micrograms to 175 micrograms, 5 micrograms to 150 micrograms, 5 micrograms to 125 micrograms, 5 micrograms to 100 micrograms, 5 micrograms to 90 micrograms, 5 micrograms to 80 micrograms, 5 micrograms to 70 micrograms, 5 micrograms to 60 micrograms, 5 micrograms to 50 micrograms, 5 micrograms to 40 micrograms, 5 micrograms to 30 micrograms, 5 micrograms to 20 micrograms, 5 micrograms to 10 micrograms, 10 micrograms to 1000 micrograms, 10 micrograms to 900 micrograms, 10 micrograms to 800 micrograms, 10 micrograms to 700 micrograms, 10 micrograms to 600 micrograms, 10 micrograms to 500 micrograms, 10 micrograms to 400 micrograms, 10 micrograms to 300 micrograms, 10 micrograms to 200 micrograms, 10 micrograms to 175 micrograms, 10 micrograms to 150 micrograms, 10 micrograms to 125 micrograms, 10 micrograms to 100 micrograms, 10 micrograms to 90 micrograms, 10 micrograms to 80 micrograms, 10 micrograms to 70 micrograms, 10 micrograms to 60 micrograms, 10 micrograms to 50 micrograms, 10 micrograms to 40 micrograms, 10 micrograms to 30 micrograms, 10 micrograms to 20 micrograms, 50 micrograms to 1000 micrograms, 50 micrograms to 900 micrograms, 50 micrograms to 800 micrograms, 50 micrograms to 700 micrograms, 50 micrograms to 600 micrograms, 50 micrograms to 500 micrograms, 50 micrograms to 400 micrograms, 50 micrograms to 300 micrograms, 50 micrograms to 200 micrograms, 50 micrograms to 175 micrograms, 50 micrograms to 150 micrograms, 50 micrograms to 125 micrograms, 50 micrograms to 100 micrograms, 50 micrograms to 90 micrograms, 50 micrograms to 80 micrograms, 50 micrograms to 70 micrograms, or 50 micrograms to 60 micrograms. 100 micrograms to 1000 micrograms, 100 micrograms to 900 micrograms, 100 micrograms to 800 micrograms, 100 micrograms to 700 micrograms, 100 micrograms to 600 micrograms, 100 micrograms to 500 micrograms, 100 micrograms to 400 micrograms, 100 micrograms to 300 micrograms, 100 micrograms to 200 micrograms, 100 micrograms to 175 micrograms, 100 micrograms to 150 micrograms, 300 micrograms to 1000 micrograms, 300 micrograms to 900 micrograms, 300 micrograms to 800 micrograms, 300 micrograms to 700 micrograms, 300 micrograms to 600 micrograms, 300 micrograms to 500 micrograms, 300 micrograms to 400 micrograms, 500 micrograms to 1000 micrograms, 500 micrograms to 900 micrograms, 500 micrograms to 800 micrograms, 500 micrograms to 700 micrograms, 500 micrograms to 600 micrograms, 600 micrograms to 800 micrograms, or 700 micrograms to 900 micrograms.

Nevertheless, given the targeted delivery provided by the LNP of the present disclosure, one can expect that the effective amount required in the methods of the present disclosure might be lower than the effective amount required in other non-targeted delivery methods. For example, the effective amount required in the methods of the present disclosure might be lower than the effective amount required in other non-targeted delivery methods by at least 1, 2, 3, 4, 5, 6, 7, 8, 9, 10, 15, 20, 25, 30, 35, 40, 45, 50, 60, 70, 80, 90, 95, or 99%, or any range defined by the foregoing endpoints, such as, included or excluded, 1 to 99%, 1 to 95%, 1 to 90%, 1 to 80%, 1 to 70%, 1 to 60%, 1 to 50%, 1 to 40%, 1 to 30%, 1 to 20%, 1 to 10%, 1 to 5%, 5 to 99%, 5 to 95%, 5 to 90%, 5 to 80%, 5 to 70%, 5 to 60%, 5 to 50%, 5 to 40%, 5 to 30%, 5 to 20%, 5 to 10%, 10 to 90%, 10 to 80%, 10 to 70%, 10 to 60%, 10 to 50%, 10 to 40%, 10 to 30%, 10 to 20%, 30 to 99%, 30 to 95%, 30 to 90%, 30 to 80%, 30 to 70%, 30 to 60%, 30 to 50%, 30 to 40%, 50 to 99%, 50 to 95%, 50 to 90%, 50 to 80%, 50 to 70%, 50 to 60%, 70 to 99%, 70 to 95%, 70 to 90%, 70 to 80%, 80 to 99%, 80 to 95%, 80 to 90%, 90 to 99%, or 95 to 99%.

Furthermore, in some embodiments where the LNP of the present disclosure is used to deliver an antigenic agent or a nucleic acid encoding the antigenic agent to induce antibodies against the antigenic agent, the titer of the antibody induced by the present disclosure, compared with the titer of the antibody induced by non-targeted delivery methods, increase 1, 2, 3, 4, 5, 6, 7, 8, 9, or 10 logs, or any range defined by the foregoing endpoints, such as, included or excluded 1 to 10 logs, 1 to 8 logs, 1 to 6 logs, 1 to 4 logs, 2 to 9 logs, 2 to 7 logs, 2 to 5 logs, 3 to 10 logs, 3 to 8 logs, 3 to 5 logs, or 4 to 6 logs.

In some other embodiments, where the LNP of the present disclosure is used to deliver an antigenic agent or a nucleic acid encoding the antigenic agent to induce an immune response against the antigenic agent, the antibody titer against the antigenic agent induced by the present disclosure, compared with that of non-targeted delivery methods, is 0.1, 0.2, 0.5, 1, 2, 3, 4, 5, 6, 7, 8, 9, or 10 times higher, or any range defined by the foregoing endpoints, such as, included or excluded, 0.1 to 10, 0.1 to 9, 0.1 to 8, 0.1 to 7, 0.1 to 6, 0.1 to 5, 0.1 to 4, 0.1 to 3, 0.1 to 2, 0.1 to 1, 0.1 to 0.5, 0.5 to 10, 0.5 to 9, 0.5 to 8, 0.5 to 7, 0.5 to 6, 0.5 to 5, 0.5 to 4, 0.5 to 3, 0.5 to 2, 0.5 to 1, 1 to 10, 1 to 9, 1 to 8, 1 to 7, 1 to 6, 1 to 5, 1 to 4, 1 to 3, 1 to 2, 3 to 10, 3 to 9, 3 to 8, 3 to 7, 3 to 6, 3 to 5, 3 to 4, 5 to 10, 5 to 9, 5 to 8, 5 to 7, 5 to 6, 7 to 10, 7 to 9, 7 to 8, or 8 to 10.

Yet in some embodiments where the LNP of the present disclosure is used to deliver an antigenic agent or a nucleic acid encoding the antigenic agent to induce an immune response against the antigenic agent, the immune response is induced 1, 2, 3, 4, 5, 6, 7, 8, 9, 10, 12, 14, 16, 18, or 20 days earlier than the immune response induced by non-targeted delivery methods, or any range defined by the foregoing endpoints, such as, included or excluded, 1 to 20, 1 to 18, 1 to 14, 1 to 10, 1 to 6, 2 to 20, 2 to 18, 2 to 14, 2 to 10, 2 to 6, 5 to 20, 5 to 18, 5 to 14, or 5 to 10 days earlier.

In some embodiments, the LNP, as described herein in the methods of the present disclosure, is administered at a dosage level sufficient to deliver a payload from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, per subject body weight per day, one or more times a day, to obtain the desired in vivo effect.

Definition

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry, and recombinant DNA technology, which are within the skill of the art. The materials, methods, and examples are illustrative only and not limiting. The following is presented by way of illustration and is not intended to limit the scope of the disclosure.

Numbers expressing quantities of ingredients, properties such as molecular weight, reaction conditions and results, and so forth, used to describe and claim certain embodiments of the present disclosure are to be understood as being modified in some instances by the term "about." A skilled artisan in the field would understand the meaning of the term "about" in the context of the value that it qualifies. The numerical values presented in some embodiments of the present disclosure may contain certain errors resulting from the standard deviation in their respective testing measurements. For example, the term "about," as used herein, refers to a measurable value such as an amount, a temporal duration, and the like and is meant to encompass variations of 20%, +10%, +5%, +1%, or +0.1% from the specified value, as such variations are appropriate.

As used herein, "substantially" means sufficient to work for the intended purpose. The term "substantially" thus allows for minor, insignificant variations from an absolute or perfect state, dimension, measurement, result, or the like, such as expected by a person of ordinary skill in the field, but that does not appreciably affect overall performance. When used with respect to numerical values or parameters or characteristics expressed as numerical values, "substantially" means within ten percent.

As used herein, "treat," "treatment," and "treating" refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

As used herein, "preventing" and "prevention" are used interchangeably with "prophylaxis" and can mean complete prevention of infection or prevention of the development of symptoms of that infection, a delay in the onset of a disease or its symptoms, or a decrease in the severity of a subsequently developed infection or its symptoms.

As used herein, "glycan" or "glycosyl group refers to a polysaccharide, oligosaccharide, or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc.).

As used herein, "alkyl" refers to a hydrocarbon chain that may be a straight chain or branched chain, saturated or unsaturated, containing the indicated number of carbon atoms. For example, $C_{1-6}$ indicates that the group may have from 1 to 6 (inclusive) carbon atoms in it. Non-limiting examples include methyl, ethyl, iso-propyl, tert-butyl, n-hexyl. A "heteroalkyl" group is an alkyl group in which at least one carbon of the chain has been replaced by a heteroatom. In some embodiments, the heteroalkyl group has 1 to 20 carbon atoms. The term "alkoxy" is intended to mean the moiety —OR, where R is alkyl. The term "aryloxy" is intended to mean the moiety —OR, where R is aryl.

As used herein, "alkenyl" refers to a hydrocarbon chain including at least one double bond, which may be a straight chain or branched chain, and containing the indicated number of carbon atoms. For example, $C_{2-6}$ indicates that the group may have from 2 to 6 (inclusive) carbon atoms in it. Non-limiting examples include ethenyl and prop-1-en-2-yl.

As used herein, "alkynyl" refers to a hydrocarbon chain including at least one triple bond, which may be a straight chain or branched chain, and containing the indicated number of carbon atoms. For example, $C_{2-6}$ indicates that the group may have from 2 to 6 (inclusive) carbon atoms in it. Non-limiting examples include ethynyl and 3,3-dimethylbut-1-yn-1-yl.

As used herein, "cycloalkyl" refers to a nonaromatic cyclic, bicylic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. A cycloalkyl can include one or more elements of unsaturation; a cycloalkyl that includes an element of unsaturation is herein also referred to as a "cycloalkenyl". Examples include cyclopropyl, cyclobutyl, cyclopentyl, cyclopentenyl, cyclohexyl, cyclohexenyl, cycloheptyl, and cyclooctyl.

As used herein, "heterocycloalkyl" refers to a nonaromatic 5-8 membered monocyclic, 8-12 membered bicyclic, or 11-14 membered tricyclic ring fused or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Heterocycloalkyls can also include oxidized ring members, such as —N(O)—, —S(O)—, and —$S(O)_2$—. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

As used herein, "aryl" or "aryl group" refers to a moiety formed by the removal of one or more hydrogen ("H") or deuterium ("D") from an aromatic compound. The aryl group may be a single ring (monocyclic) or have multiple rings (bicyclic, or more) fused together or linked covalently. A "carbocyclic aryl" has only carbon atoms in the aromatic ring(s). A "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Heteroaryls can also include oxidized ring members, such as —N(O)—, —S(O)—, and —$S(O)_2$—. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

As used herein, "amine" refers to a compound that contains a basic nitrogen atom with a lone pair. The term "amino" refers to the functional group or moiety —$NH_2$, —NHR, or —$NR_2$, where R is the same or different at each occurrence and can be an alkyl group or an aryl group.

As used herein, "halogen" or "halo" refers to fluorine, bromine, chlorine, or iodine. In particular, it typically refers to fluorine or chlorine when attached to an alkyl group and further includes bromine or iodine when on an aryl or heteroaryl group.

As used herein, the term "haloalkyl" refers to an alkyl as defined herein, which is substituted by one or more halo groups. The haloalkyl can be monohaloalkyl, dihaloalkyl, trihaloalkyl, or polyhaloalkyl, including perhaloalkyl. A monohaloalkyl can have one chloro or fluoro within the alkyl group. Chloro and fluoro are commonly present as substituents on alkyl or cycloalkyl groups; fluoro, chloro, and bromo are often present on aryl or heteroaryl groups. Dihaloalkyl and polyhaloalkyl groups can have two or more of the same halo atoms or a combination of different halo groups on the alkyl. Typically, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, 2,2,2-trifluoroethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl.

As used herein, unless otherwise specified, the term "heteroatom" refers to a nitrogen (N), oxygen (O), or sulfur (S) atom.

Example

Example 1: Synthesis of Exemplary Compounds of the Present Disclosure

Chemical Materials and Methods

For chemical synthesis, all starting materials and commercially obtained reagents were purchased from Sigma-Aldrich and used as received unless otherwise noted. All reactions were performed in oven-dried glassware under a nitrogen atmosphere using dry solvents. $^{1}H$ and $^{13}C$ NMR spectra were recorded on Brucker AV-600 spectrometer, and were referenced to the solvent used ($CDCl_3$ at δ 7.24 and 77.23, $CD_3OD$ at δ 3.31 and 49.2, and $D_2O$ at δ 4.80, and DMSO-$d_6$ at δ 2.5 and 39.51 for $^{1}H$ and $^{13}C$, respectively). Chemical shifts (6) are reported in ppm using the following convention: chemical shift, multiplicity (s=singlet, d=doublet, t=triplet, q=quartet, m=multiplet), integration, and coupling constants (J), with Jreported in Hz. High-resolution mass spectra were recorded under ESI-TOF mass spectroscopy conditions. Silica gel (E, Merck) was used for flash chromatography. IMPACT system (Intein Mediated Purification with Affinity Chitinbinding Tag) was purchased from New England Biolabs. His-tag purification resin was purchased from Roche. HiTrap IMAC column (5 mL) was purchased from GE Healthcare Life Sciences. Gel permeation chromatography (GPC) equipped with Ultimate 3000 liquid chromatography associated with a 101 refractive index detector and Shodex columns was used to analyze the polymeric products using THF as the eluent at 30° C. with 1 mL $min^{-1}$ flow rate. The calibration was based on the narrow linear poly(styrene) Shodex standard (SM-105). The Mw and dispersity of the polymeric products were calculated using DIONEX chromeleon software. Transmission electron microscopy (TEM) images were obtained by a FEI Tecnai G2 F20 S-Twin.

The chemical materials and methods described herein apply to all examples described in the present disclosure.

Synthesis and Results

The exemplary compounds described here were synthesized according to the synthesis Scheme 1, Scheme 2, and Scheme 3 below. The detailed synthesis procedures are described below.

Scheme 1
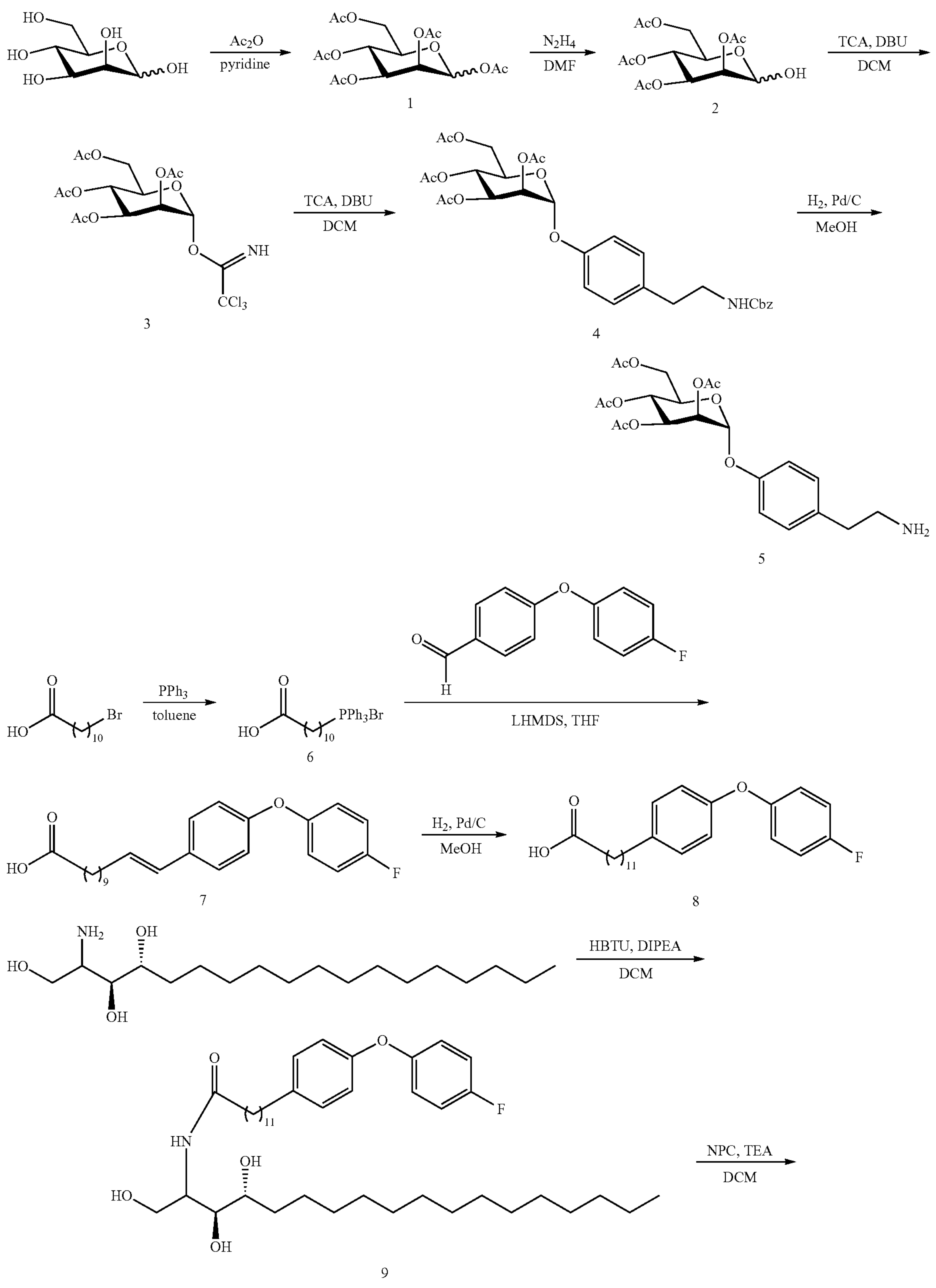

-continued
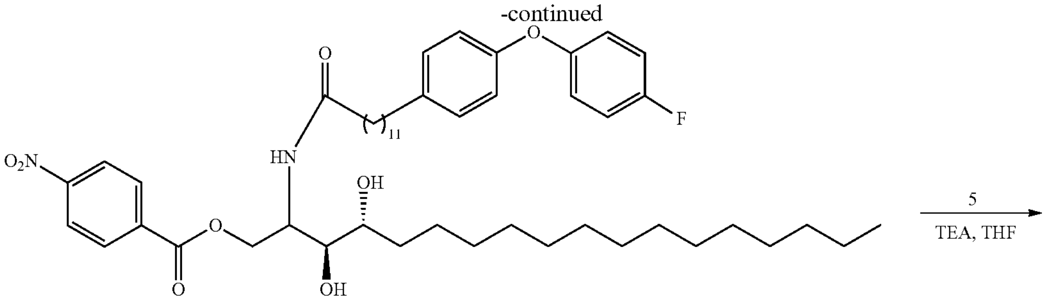
10
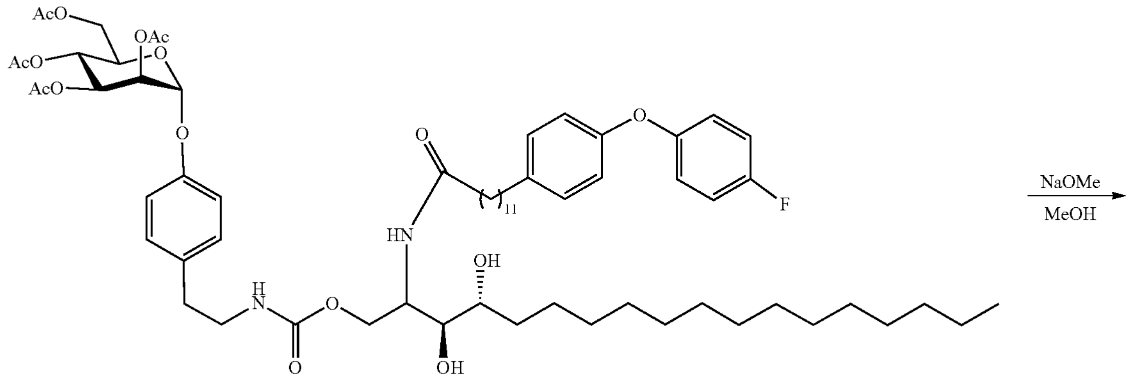
11
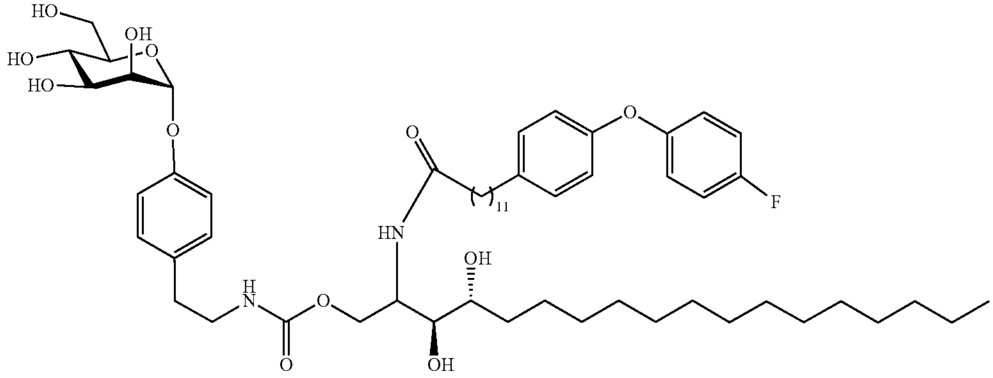
12
Scheme 2
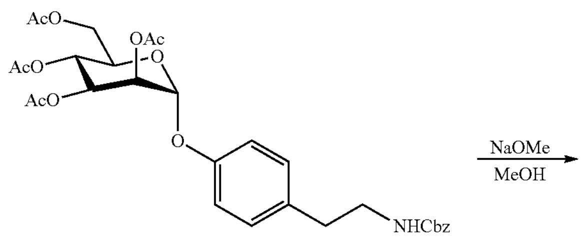
4
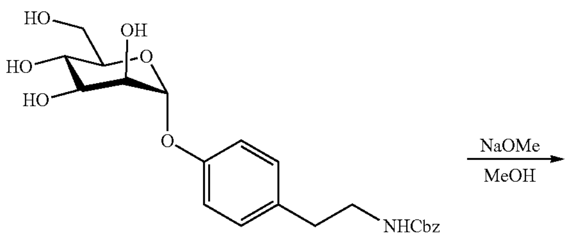
13

-continued
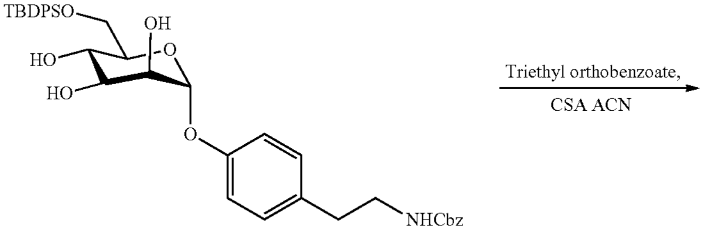
14
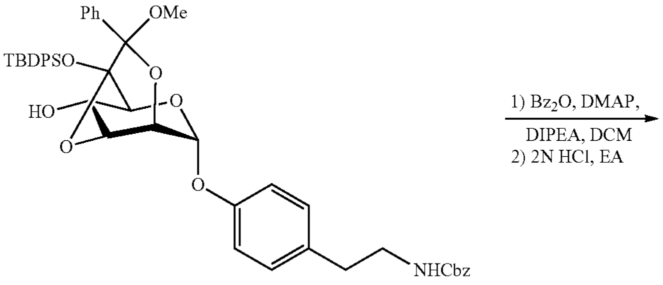
15
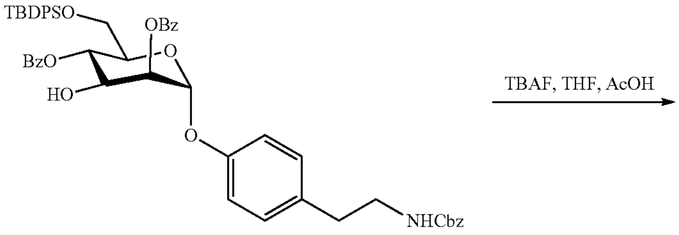
16
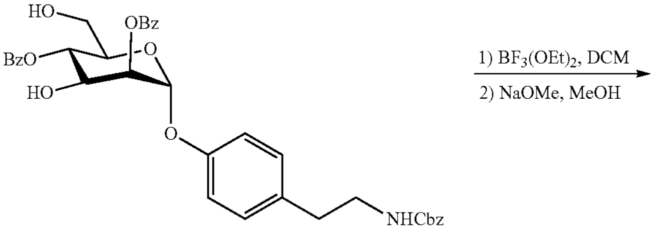
17
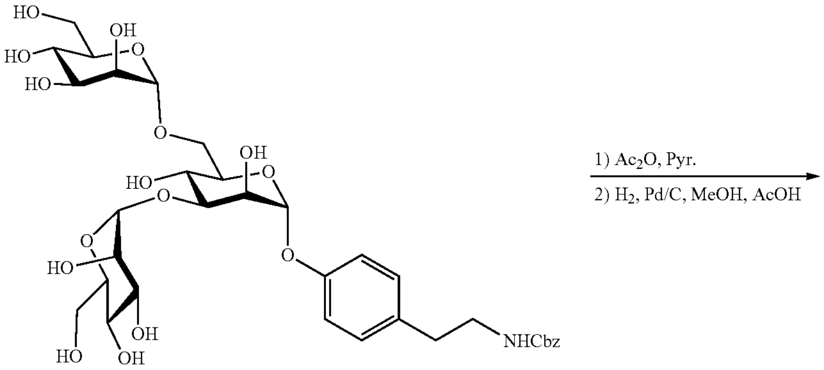
18

-continued
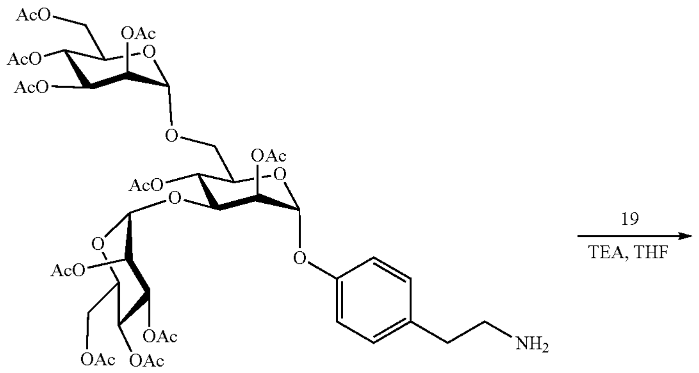
19
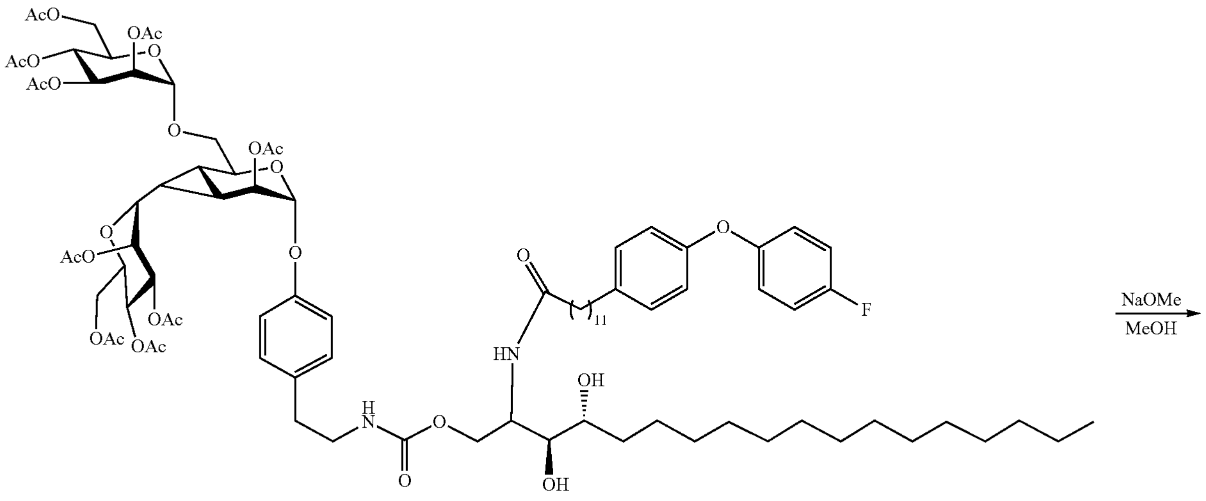
20
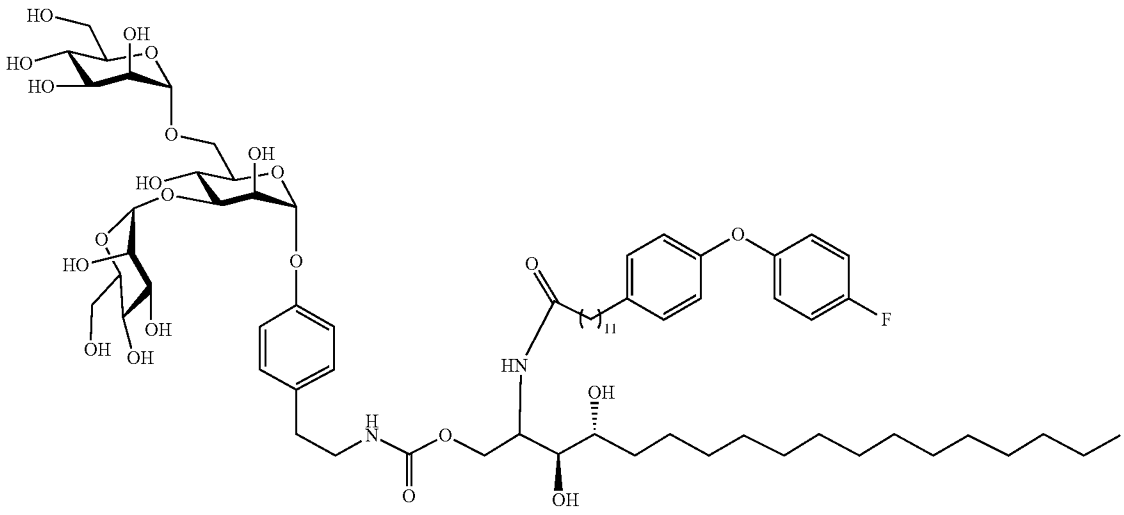
21

Scheme 3

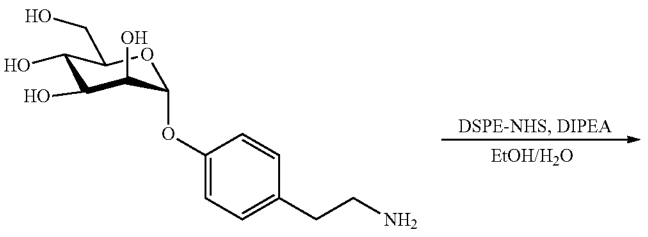

22s

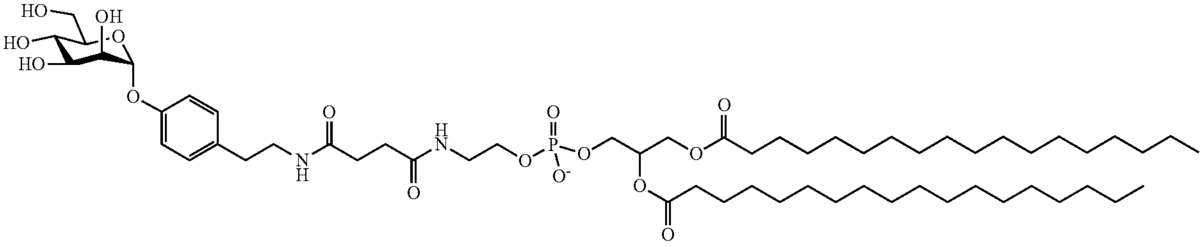

22

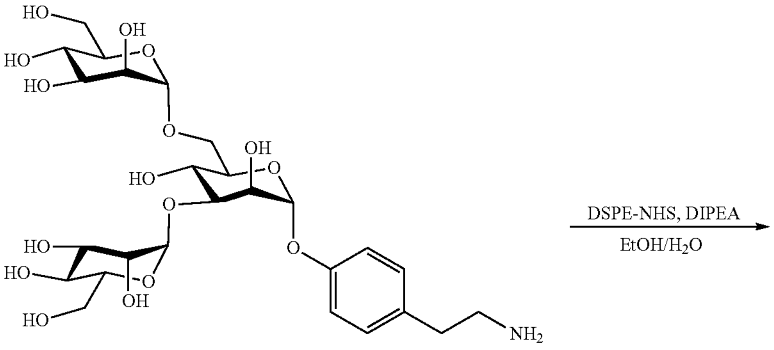

23s

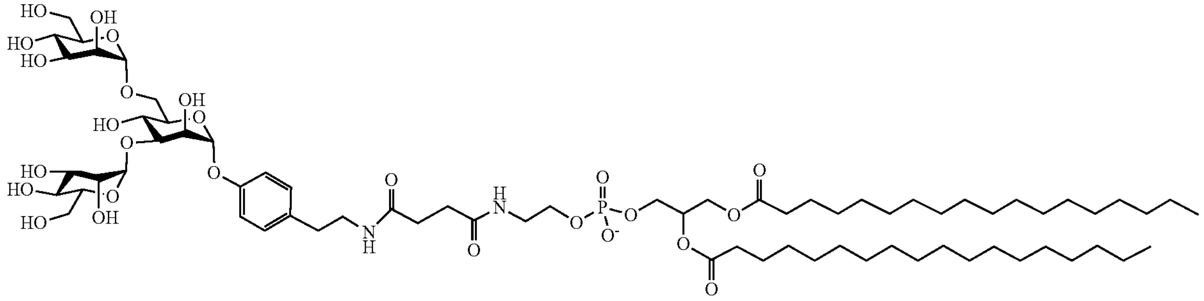

23

Compounds 1 to 5

Compounds 1-5 were synthesized and characterized according to a published protocol (ACS Nano 2021, 15, 309-321).

Compound 8

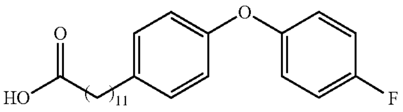

(11-Carboxynonyl)triphenylphosphonium bromide 6 (2.5 g, 10 mmol) was prepared by refluxing triphenylphosphine (10 mmol) and 11-bromoundecanoic acid (10 mmol). It was then dissolved in 50 ml of tetrahydrofuran (THF) and cooled to 0° C. lithium bis(trimethylsilyl)amide (LHMDS; 1 M in THF, 20 mmol) was added to the solution to produce an orange ylide. After that, 4-(4-Fluorophenoxy)benzaldehyde (12 mmol) in 20 ml of THF was added dropwise to the solution and stirred for 4 h at room temperature. The reaction was quenched with methanol and concentrated. The residue was extracted with EA and brine and then dried over $MgSO_4$. After removal of the solvent, the mixture was chromatographed on silica gel (EA-Hex=1:2) to give the unsaturated fatty acid 7. The saturated fatty acid was prepared by catalytic hydrogenation in 50 ml of methanol containing 10 mol % of 10% palladium on charcoal (Pd/C).

The reaction mixture was stirred under $H_2$ at room temperature overnight. The hydrogenated product was filtered through Celite and the resulting solution was concentrated and chromatographed on silica gel (EA-Hex=1:2) to give the product as a yellow solid (66%).

Compound 9

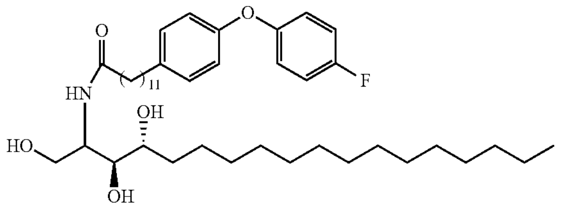

Compound 9. Compound 8 (1 mmol) in THF (10 mL) was added EDC (1.5 mmol), HOBt (1.5 mmol), DMAP (0.1 mmol), trimethylamine (2 mmol), and phytosphingosine (1.2 mmol), and the resulting solution was stirred under nitrogen at rt for 12 h. The solvent was then removed by evaporation, followed by extraction with EA/$H_2O$. The collected organic layer was washed with saturated $NaHCO_3$ (aq), water and brine, and dried over $MgSO_4$. The crude product was purified by column chromatography on silica gel (EA/Hex 1:1) to yield 9 (74%).

Compound 10

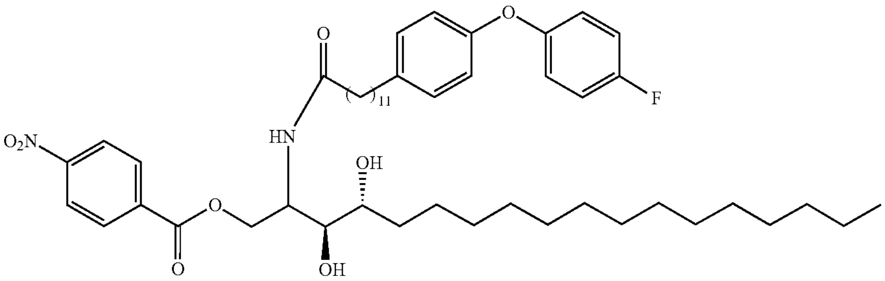

Compound 9 (1 mmol) in THF (10 mL) was added 4-nitrophenylchloroformate (2 mmol), trimethylamine (2 mmol), and the resulting solution was stirred under nitrogen at rt for 12 h. The solvent was then removed by evaporation, and the crude compound was directly used for the next step without further purification.

Compound 11

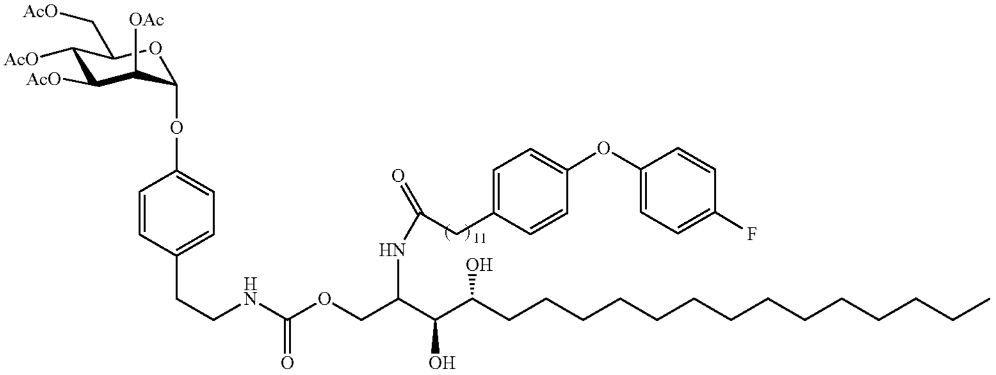

Compound 5 (1 mmol) in THF (10 mL) was added 10 (1 mmol) and trimethylamine (2 mmol), and the resulting solution was stirred under nitrogen at rt for 2 h. The solvent was then removed by evaporation, followed by extraction with EA/$H_2O$. The collected organic layer was washed with saturated $NaHCO_3$(aq), water and brine, and dried over $MgSO_4$. The crude product was purified by column chromatography on silica gel (EA/Hex 1:1+10% MeOH) to yield 11 (59%).

Compound 12

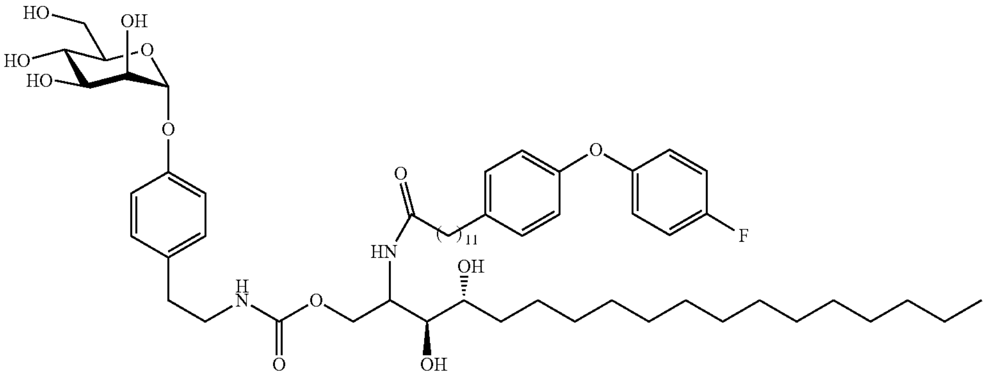

Compound 11 in MeOH was added NaOMe (0.2 eq), and the resulting solution was stirred under nitrogen at room temperature for 2 hours. The mixture was neutralized by IR-120 and then filtered and concentrated to dryness in vacuo to give compound 12 (quant.).

Compound 13

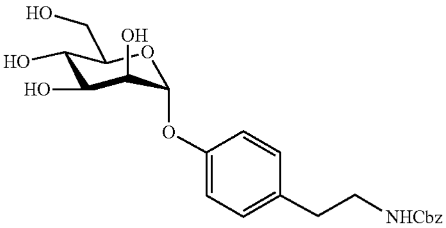

Compound 4 in MeOH was added NaOMe (0.2 eq), and the resulting solution was stirred under nitrogen at rt for 2 h. The mixture was neutralized by IR-120 and then filtered and concentrated to dryness in vacuo to give compound 13 (quant.).

Compound 14

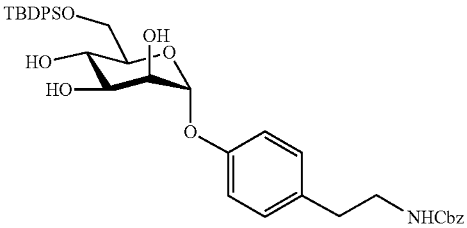

Compound 13 (1 mmol) in MeOH was added NaOMe (0.2 eq), and the resulting solution was stirred under nitrogen at rt for 2 h. The mixture was neutralized by IR-120 and then filtered and concentrated to dryness in vacuo. It was then dissolved in anhydrous DCM (10 mL) and treated with imidazole (1.5 mmol) at 0° C., followed by the addition of TBDPSCl (1.2 mmol). The mixture was stirred at room temperature for 2.5 h under a nitrogen atmosphere. The reaction was quenched by the addition of MeOH. After stirring at room temperature for 10 min, the solvent was removed under reduced pressure to give a dry residue that was purified by column chromatography with MeOH/DCM (1/10) to give compound 14 (82%).

Compound 15

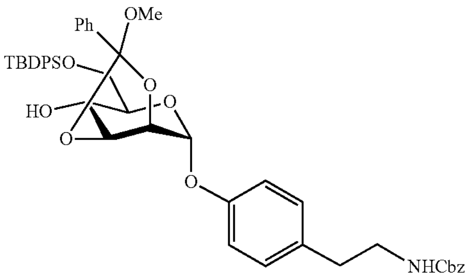

To a solution of compound 14 (1 mmol) and a catalytic amount of CSA (0.1 mmol) in $CH_3CN$ (20 mL) was added trimethyl orthobenzoate (3 mmol) at room temperature under atmospheric pressure of nitrogen. After stirring for 30 min, $Et_3N$ was added to quench the reaction, and the resulting mixture was dried under reduced pressure. The residue was purified by column chromatography with EA/Hex (1/2) to give compound 15 (79%).

Compound 16

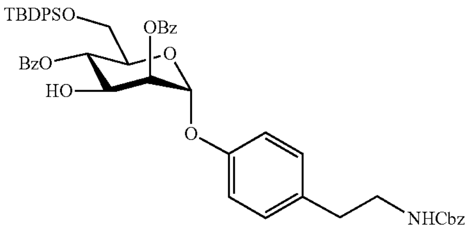

Compound 15 (1 mmol) was dissolved in DCM (10 mL) and sequentially mixed with DIPEA (2 mmol), benzoic anhydride (2 mmol), and DMAP (0.1 mmol). After stirring for 2 hr, the solvent was evaporated under reduced pressure to give a dry residue and then poured into EA (20 mL) and 2 N HCl (10 mL) with vigorous stirring for 30 min. The solvent was then removed by evaporation, followed by extraction with EA/$H_2O$. The collected organic layer was washed with ice-cold saturated $NaHCO_3$(aq), water and brine, and dried over $MgSO_4$. The dry residue was purified by column chromatography with EA/Hex (1/2) to give compound 16 (71%).

Compound 17

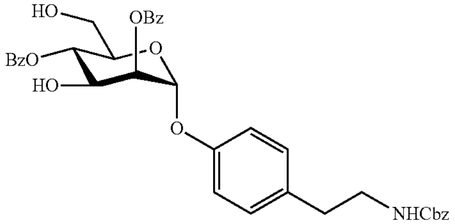

Compound 16 (1 mmol) was added AcOH (4 mmol) and 1 M TBAF (2.4 mmol in THF) at 0° C. The resulting mixture was warmed up to room temperature gradually, stirred for another 2 h, and then diluted with EA. The organic layer was washed with saturated $NaHCO_3$(aq), water, and brine, dried with anhydrous $MgSO_4$, and concentrated under reduced pressure. The dry residue was purified by column chromatography with EA/Hex (1/2) to give compound 47 (88%).

Compound 18

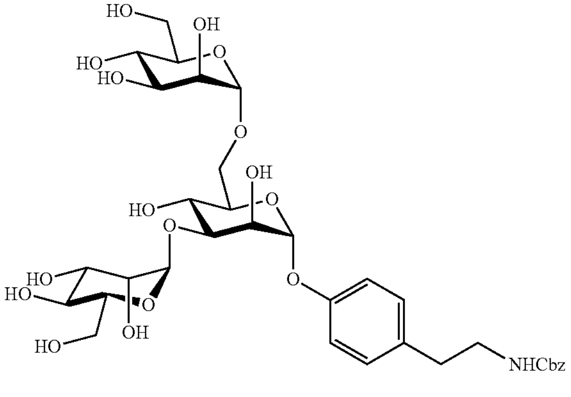

To a stirred solution of 17 (1 mmol) and 4 A molecular sieve (0.1 g) in anhydrous DCM (10 mL) was cooled to −40° C. and then $BF_3(OEt)_2$ (0.1 mmol) was added dropwise to the solution. A solution of 3 in anhydrous DCM was added dropwise to the above mixture and stirred for 1 h at −40° C. After that, the reaction was gradually warmed to room temperature and stirred for another 1 h. The solution was quenched by adding triethylamine, then filtered and added saturated. $NaHCO_3$ aq. and extracted with DCM. The organic layer was dried with $MgSO_4$ and evaporated to dryness. The residue was purified by flash column chromatography on silica gel to give a trisaccharide product. The product was then dissolved in MeOH, and NaOMe (0.2 eq) was added, and the resulting solution was stirred at room temperature for 2 h. The mixture was neutralized by IR-120 and then filtered and concentrated to dryness in vacuo. The deacetylated mixture was purified by Bio-Gel P-2 Gel (Biorad) with $H_2O$ as eluent to obtain a pure trisaccharide. The compound was lyophilized to dryness to give compound 18 (39%).

Compound 19

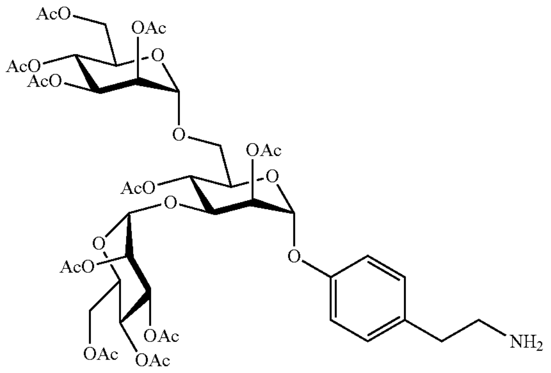

Compound 13 (1 mmol) in MeOH was added NaOMe (0.2 eq), and the resulting solution was stirred under nitrogen at rt for 2 h. The mixture was neutralized by IR-120 and then filtered and concentrated to dryness in vacuo.

Compound 20

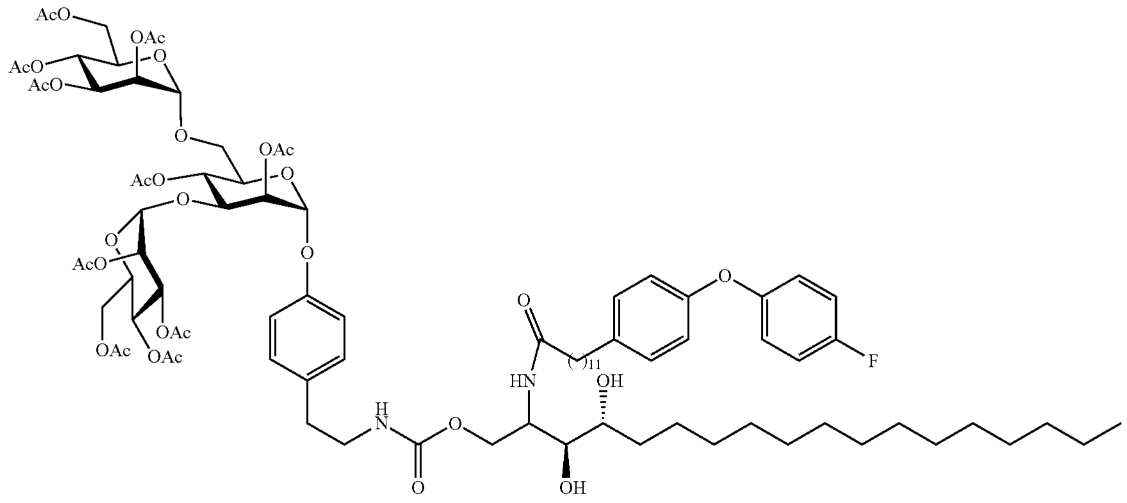

Compound 19 (1 mmol) in THF (10 mL) was added 10 (1 mmol) and trimethylamine (2 mmol), and the resulting solution was stirred under nitrogen at rt for 2 h. The solvent was then removed by evaporation, followed by extraction with EA/$H_2O$. The collected organic layer was washed with saturated $NaHCO_3$(aq), water and brine, and dried over $MgSO_4$. The crude product was purified by column chromatography on silica gel (EA/Hex 1:1+10% MeOH) to yield 20.

Compound 21

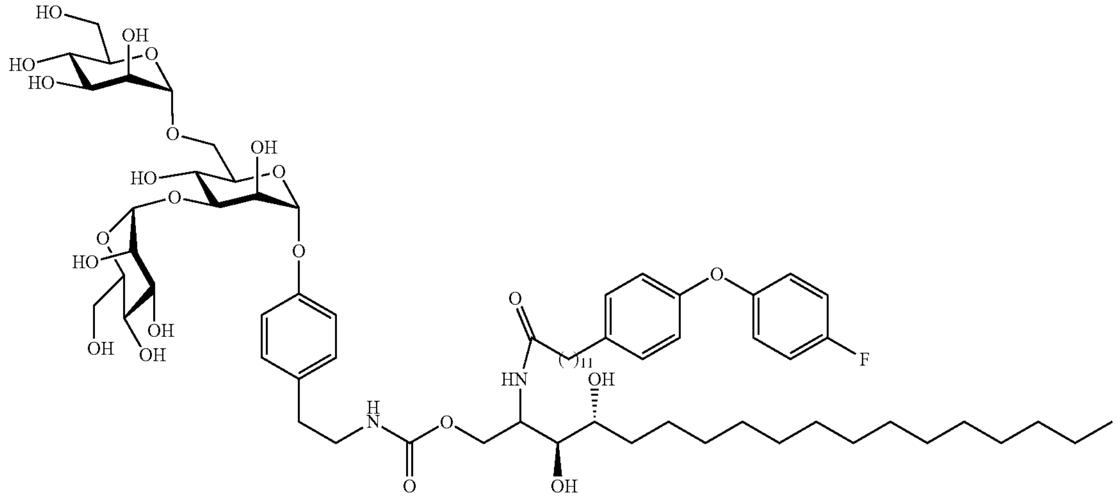

Figure 12:
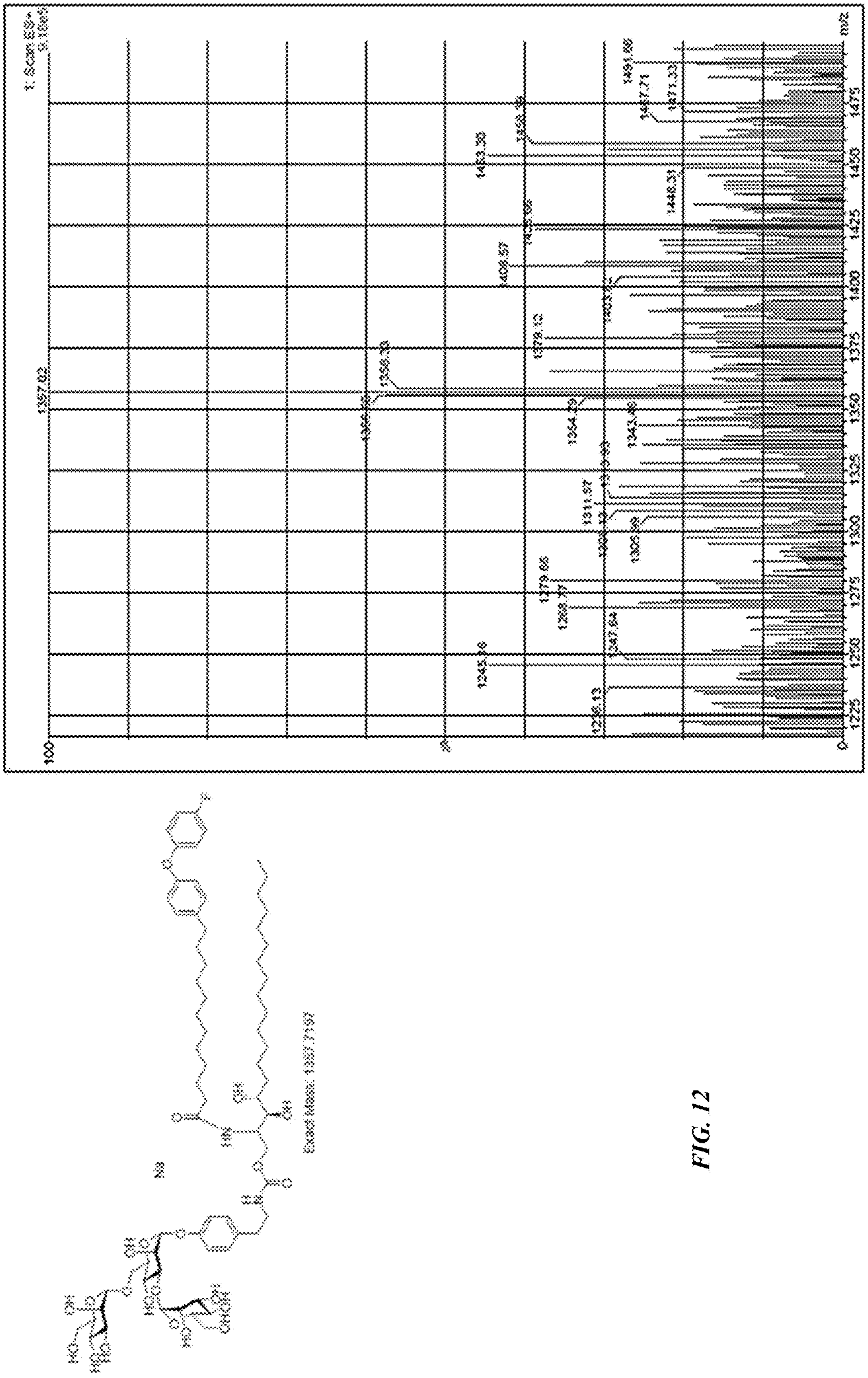
FIG. 12 shows the LCMS spectrum of compound 21 of the present disclosure.

Compound 20 in MeOH was added NaOMe (0.2 eq), and the resulting solution was stirred under nitrogen at room temperature for 2 hours. The mixture was neutralized by IR-120 and then filtered and concentrated to dryness in vacuo to give compound 21 (quant.). The resulting compound 21 was examined using LCMS spectrum, which shows peaks at 1236.13, 1245.16, 1247.64, 1268.77, 1279.86, 1305.99, 1308.13, 1311.57, 1313.93, 1343.46, 1354.29, 1355.60, 1358.33, 1379.12, 1403.82, 1408.57, 1425.66, 1448.31, 1453.30, 1458.39, 1467.71, 1471.33, and 1491.66 (FIG. 12).

Compound 22
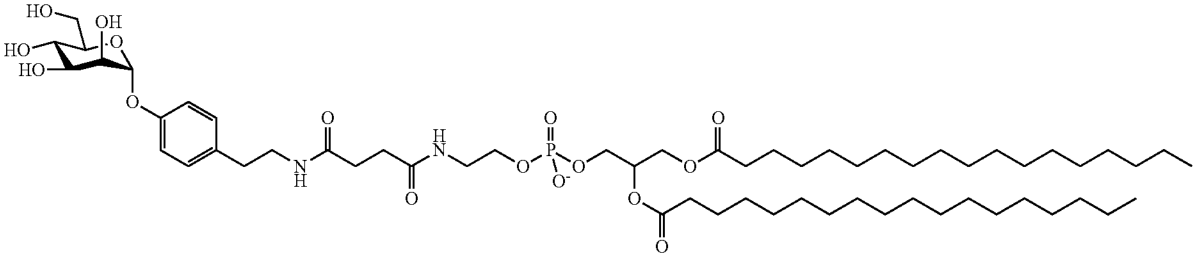
Arylmannoside 22s (0.1 mmol) in EtOH/$H_2O$ (0.5/0.5 mL) was added to DSPE-NHS (0.1 mmol), and trimethylamine (2 mmol), and the resulting solution was stirred at rt for 12 h. The solvent was removed by evaporation and the crude product was purified Bio-Gel P-2 Gel with $H_2O$ as eluent to yield 22 (79%).

Compound 23
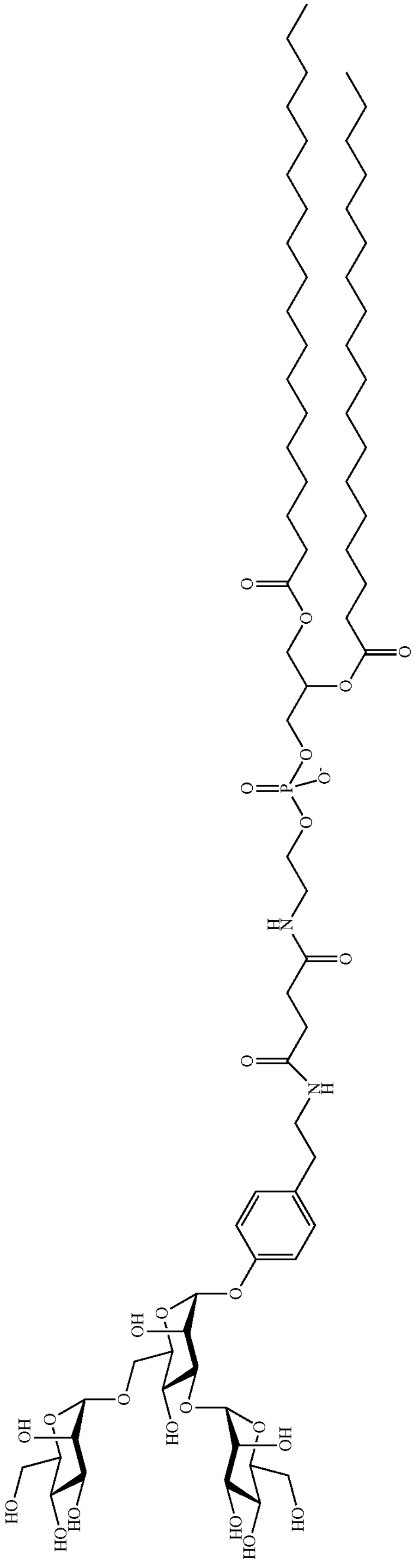

Aryltrimannoside 23s (0.1 mmol) in EtOH/$H_2O$ (0.5/0.5 mL) was added DSPE-NHS (0.1 mmol) and trimethylamine (2 mmol), and the resulting solution was stirred at room temperature for 12 h. The solvent was removed by evaporation and the crude product was purified Bio-Gel P-2 Gel with $H_2O$ as eluent to yield 23 (76%).

Example 2: Preparation and Characterization of the LNP of the Present Disclosure Preparation of LNP A lipid mix solution in EtOH (10 mg/ml) having a molar ratio of 50% SM-102, 10% DSPC, 38.5% cholesterol, and 1.5% DMG-PEG2000 was prepared. An LNP formulation was prepared by mixing the compound of the present disclosure with the lipid mix solution (with a molar ratio of 45% SM-102, 9% DSPC, 34.5% cholesterol, 1.5% DMG-PEG2000, and 10% compound of the present disclosure). The LNP formulation was added into a 1.5 mL tube. Then, a mRNA payload, diluted with citrate buffer before use (10 mM, pH4), was added to the tube at a final concentration of 0.18 ug/uL. The mRNA aqueous solution in the tube was then quickly added to an ethanol solution and mixed well by vortex for 1 minute. The resulting solution was then dialyzed by micro float-A-Lyzer (8-10 kD) against PBS at 4° C. overnight to obtain the LNP of this example. The resulting LNP can be stored at 4° C. for a few days before use.

Characterization of LNP

Size Measurement. The LNP prepared above was examined using dynamic light scattering (DNP) to measure its size. First, 5 μL of the LNP solution was transferred to a clean 1.5 mL tube and diluted with 95 μL of PBS. The mixture was then transferred to a cuvette, and the particle size of the LNP was measured using a Nano ZS machine. The following table shows the sizes and the Polydispersity Index (PDI) of the LNP samples prepared.

TABLE the size and PDI measurement

| Sample | Size (nm)_Mean ± SD | PDI_Mean ± SD |
|---|---|---|
| Compound 24-LNP | 138.5 ± 0.7074 | 0.1498 ± 0.002694 |
| Compound 25-LNP | 161 ± 0.3246 | 0.1221 ± 0.02095 |
| Compound 12-LNP | 177.5 ± 1.79 | 0.1381 ± 0.02234 |
| Compound 22-LNP | 191.7 ± 1.617 | 0.1625 ± 0.0294 |
| Compound 23-LNP | 170.7 ± 1.353 | 0.1109 ± 0.01918 |

Zeta potential and encapsulation efficiency. Next, the encapsulation efficiency of the LNP of the present disclosure was evaluated using a Quant-it Ribogreen assay. A 2000-fold diluted quant-it Ribogreen reagent with 1×TE (working solution) was prepared. Then, an RNA standard dilution series from 0-50 ng/mL (100 μL) was prepared to obtain a standard curve. 5 μL of the LNP solution prepared above was transferred to a clean tube and diluted to a final volume of 100 μL. The working solution of the quant-it Ribogreen reagent (100 μL) was then added to the LNP sample. The fluorescence signal of the sample was then detected using a microplate reader (ex/em 485/535). According to the standard curve, the fluorescence signal was used to calculate the concentration of unencapsulated mRNA in solution (ng/mL). For zeta potential measurement, 0.75 mL DP-intermediate was introduced into capillary cells and measured at 25° C. using Malvern Zetasizer Pro equipment.

TABLE

Zeta potential and encapsulation efficiency

| Sample | Zeta potential (mV) | Encapsulation efficiency (%) |
|---|---|---|
| Compound 24-LNP | 0.113 | 92.15 |
| Compound 25-LNP | −4.382 | 86.69 |
| Compound 12-LNP | 0.932 | 81.47 |
| Compound 22-LNP | −0.5107 | 82.86 |
| Compound 23-LNP | 0.3875 | 90.00 |

Example 3: In Vitro Uptake and Transfection of mRNA-LNPs in Dendritic Cells

Experiment 3-1

Splenic cell preparation and BMDC culture. This example tested the uptake of several exemplary LNPs (as shown in the table below) according to the embodiments of the present disclosure in bone marrow-derived dendritic cells (BMDCs) and splenic cells. To prepare splenic cells, the mouse spleen was homogenized with the frosted end of a glass slide and treated with RBC lysis buffer (Sigma) to deplete red blood cells (RBCs), followed by passing through the cell strainer (BD Biosciences). Bone marrow was isolated from mouse femurs and tibiae and treated with RBC lysis buffer (Sigma-Aldrich) to deplete RBCs. Cells were then cultured in RPMI-1640 containing 10% heat-inactivated FBS (Thermo Fisher Scientific), 1% Penicillin/Streptomycin (Thermo Fisher Scientific), 50 M 2-mercaptoethanol (Thermo Fisher Scientific), and 20 ng/ml recombinant mouse GM-CSF (eBioscience) at a density of 2×10' cells/ml. The cells were supplemented with an equal volume of the complete culture medium (RPMI-1640, 100 U/ml Pen/Strep, 55 μM 2-mercaptoethanol, and 10% FBS) at day 3 and refreshed with one-half the volume of the medium at day 6. On day 8, the suspended cells were harvested.

Table of the exemplary LNPs tested in this experiment.

| Example | L1: Ionizable lipid | L2: Phosphatidylcholine | L3: Cholesterol | L4: PEG-Lipid | L5 the compound of the present disclosure |
|---|---|---|---|---|---|
| 1 | 45 mol % | 9 mol % | 34.5 mol % | 1.5 mol % | Compound 24 10 mol % |
| 2 | 45 mol % | 9 mol % | 34.5 mol % | 1.5 mol % | Compound 25 10 mol % |
| 3 N.C. (no LNP) | none | none | none | none | none |
| 4 P.C. | 50 mol % | 10 mol % | 38.5 mol % | 1.5 mol % | none |

Treatment of LNPs to splenic cells and BMDCs. Splenic cells or BMDCs were incubated with different FITC-labeled LNP formulations in RPMI-1640 at 37° C. for 1 hour. Cells were blocked with an Fc receptor binding inhibitor (clone: 93, eBioscience) for 20 minutes. Splenocytes were stained with antibodies against CD3 (clone: 17A2, BV421-conjugated, Biolegend), CD19 (clone: 1D3, PECy7-conjugated, BD Biosciences). BMDCs were stained with antibodies against CD11c (clone N418 APC-conjugated, Biolegend). Labeled cells were analyzed using FACSC and Flow Cytometer (BD Biosciences).

Flow Cytometry. After incubation with different mRNA-LNPs, BMDC cells were washed with ice-cold FACS buffer (1% FBS in 1×DPBS with 0.1% Sodium Azide), and incubated with purified anti-mouse CD16/32 antibody (BioLegend) in FACS buffer on ice for 20 min, followed by washing with FACS buffer. BMDCs were stained with APC anti-mouse CD11c antibody (BioLengend) at 4° C. for 30 min, and washed with FACS buffer. Finally, BMDCs were stained with propidium iodide (Sigma-Aldrich). Flow cytometry was performed on a FACS Canto™ flow cytometer (BD Bioscience).

Figure 2:
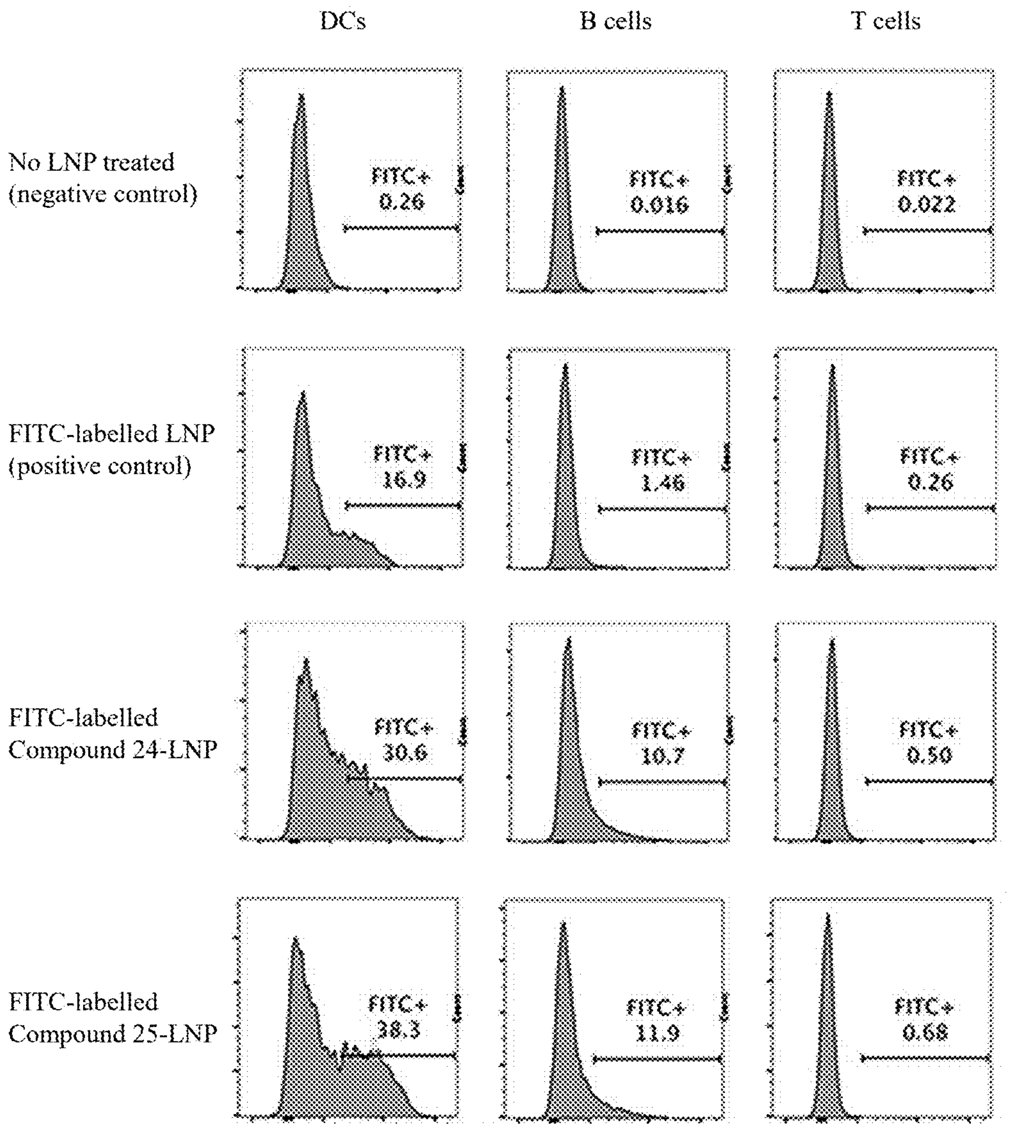
FIG. 2 provides a graphic representation of the FACS analysis results demonstrating the efficacy of the exemplary novel dendritic cell-targeting formulations of the present disclosure. The experiments showed the uptake of the exemplary novel dendritic targeting formulations of the present disclosure according to embodiments of the present disclosure targeting dendritic cells (DC), B cells, and T cells, compared with conventional LNPs. The FITC+ values shown in the figures are fluorescent intensities in arbitrary units (A.U.).

Results. The FACS results are shown in FIG. 1 and FIG. 2 and the table below. FIG. 1 shows that the BMDCs showed specific uptake of the LNPs made using compounds of the present disclosure compared with non-BMDCs. A traditional LNP (i.e., without using the compound of the present disclosure) showed slightly higher uptake by the BMDCs than the non-BDMCs, but the specificity was insignificant compared to that of the LNPs of the present disclosure (56.1/8.62 or 55.2/6.64 vs. 0.48/0.12). Similarly, in FIG. 2, dendritic cells (DCs) showed specific uptake of the LNPs of the present disclosure at least 3 times higher than B cells (30.6/10.7 and 38.3/11.9) and at least 6 times higher than T cells (30.6/0.5 and 38.3/0.68). DCs showed higher uptake of traditional LNPs but the inclination was less significant than that of the LNPs of the present disclosure.

Table of the uptake results (arbitrary unit of the FITC signals)

| Experiment 3-1 | L5 the compound of the present disclosure | FITC signal (A.U.) | | | | |
|---|---|---|---|---|---|---|
| | | BMDC | Non-BMDC | DCs | B cells | T cells |
| Example 1 | Compound 24 | 56.1 | 8.62 | 30.6 | 10.7 | 0.50 |
| Example 2 | Compound 25 | 55.2 | 6.64 | 38.3 | 11.9 | 0.68 |
| Example 3 | Negative control | 0.17 | 0.18 | 0.26 | 0.016 | 0.022 |
| Example 4 | Positive control | 0.48 | 0.12 | 16.9 | 1.46 | 0.26 |

Experiment 3-2

Exemplary LNPs (as shown in the table below) made using different formulations according to the embodiments of the present disclosure were tested in this experiment. Both uptake and transfection were tested to assess whether the payload delivered by the LNPs of the present disclosure can be expressed properly in targeted cells. Bone marrow-derived dendritic cells (BMDCs) were isolated from murine tibia and femurs of 57BL/6 mice. Bone marrow cells were stimulated for 8 days with 20 ng/mL GM-CSF in RPMI medium (RPMI-1640, 100 U/ml Pen/Strep, 55 uM 2-mercaptoethanol and 10% FBS). After 8 days of culture, $1\times10^6$ BMDCs (centrifuge 400 g, 5 mins and replace medium with 1 ml Opti-MEM) were plated in 6-well plates, and different samples of LNPs encapsulating mRNA were diluted by 0.25 mL Opti-MEM and incubated with BMDC.

For uptake analysis, FITC-labelled LNPs encapsulating mRNA that encodes a SARS COV2 Spike protein were incubated with the BMDCs at 37° C. for 2 hours. For transfection analysis, the LNPs encapsulating eGFP mRNA were incubated with the BMDCs at 37° C. for 4 hours. After 4 hours of transfection, BMDCs were supplemented with the 1.25 ml complete RPMI medium and incubated at 37° C. for 48 hours. The experiments were conducted using FACS, similar to that described above.

Table of the exemplary LNPs tested in this experiment.

| Example | L1: Ionizable lipid | L2: Phosphatidylcholine | L3: Cholesterol | L4: PEG-Lipid | L5 the compound of the present disclosure |
|---|---|---|---|---|---|
| 1 | 47.5 mol % | 9.5 mol % | 36.5 mol % | 1.5 mol % | 5 mol % Compound 22 |
| 2 | 45 mol % | 9 mol % | 34.5 mol % | 1.5 mol % | 10 mol % Compound 22 |
| 3 | 40 mol % | 8 mol % | 30.5 mol % | 1.5 mol % | 20 mol % Compound 22 |
| 4 | 47.5 mol % | 9.5 mol % | 36.5 mol % | 1.5 mol % | 5 mol % Compound 23 |
| 5 | 45 mol % | 9 mol % | 34.5 mol % | 1.5 mol % | 10 mol % Compound 23 |
| 6 | 40 mol % | 8 mol % | 30.5 mol % | 1.5 mol % | 20 mol % Compound 23 |
| 7 (control) | 50 mol % | 10 mol % | 38.5 mol % | 1.5 mol % | none |

Figure 3:
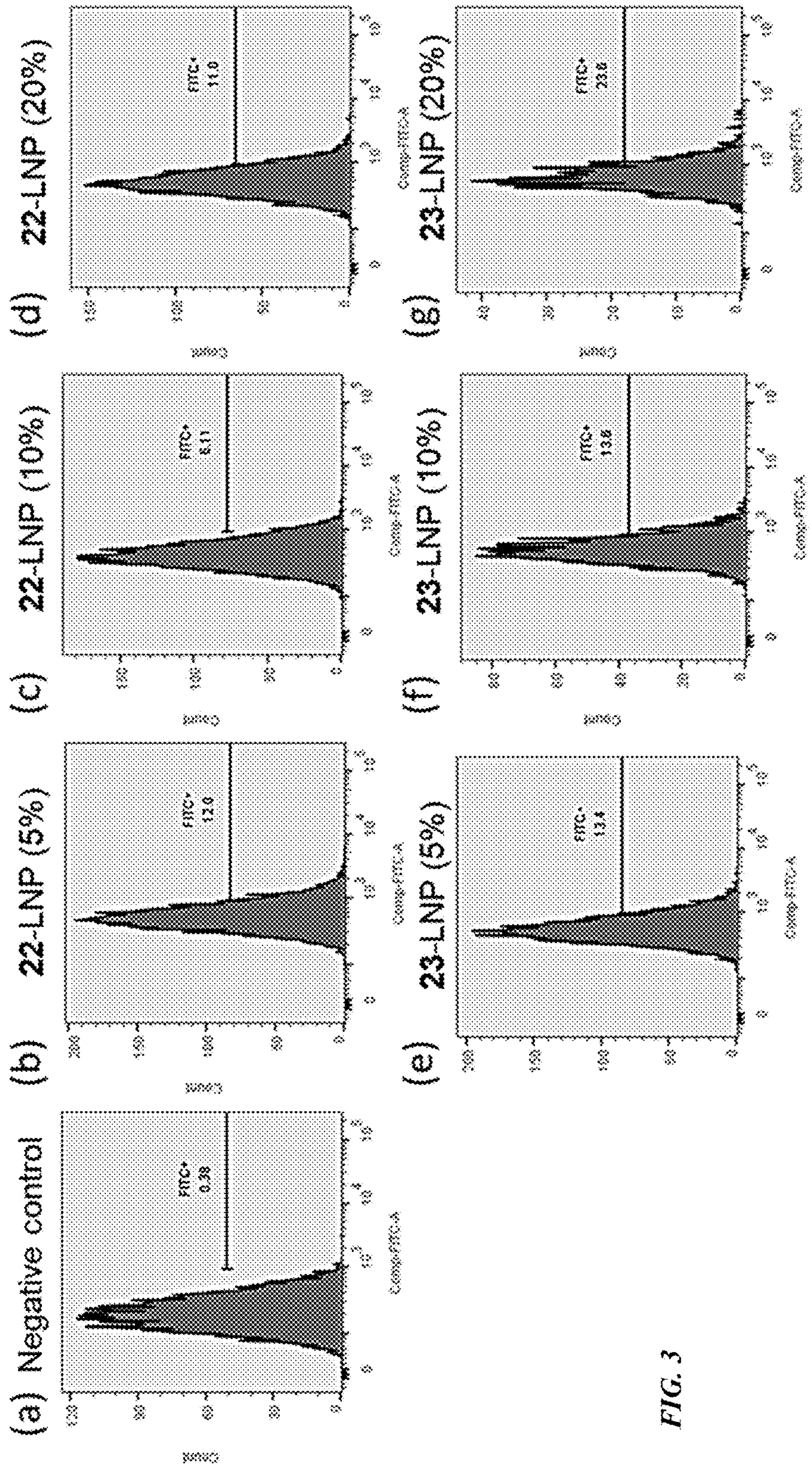
FIG. 3 provides a graphic representation showing the FACS analysis results demonstrating the efficacy of the exemplary novel dendritic targeting formulations of the present disclosure. The experiments showed the uptake of the dendritic cell-targeting formulations according to embodiments of the present disclosure targeting BDMCs compared with conventional LNPs. The FITC+ values shown in the figures are fluorescent intensities in arbitrary units (A.U.). 22-LNP represents the targeting formulation made using compound 22 of the present disclosure, and the percentage in parentheses indicates the molar ratio of compound 22. Likewise, 23-LNP represents the targeting formulation made using compound 23 of the present disclosure, and the percentage in parentheses indicates the molar ratio of compound 23. The negative control was an LNP without using the present disclosure's novel targeting compound/formulation (i.e., "traditional LNP" as described herein).
Figure 4:
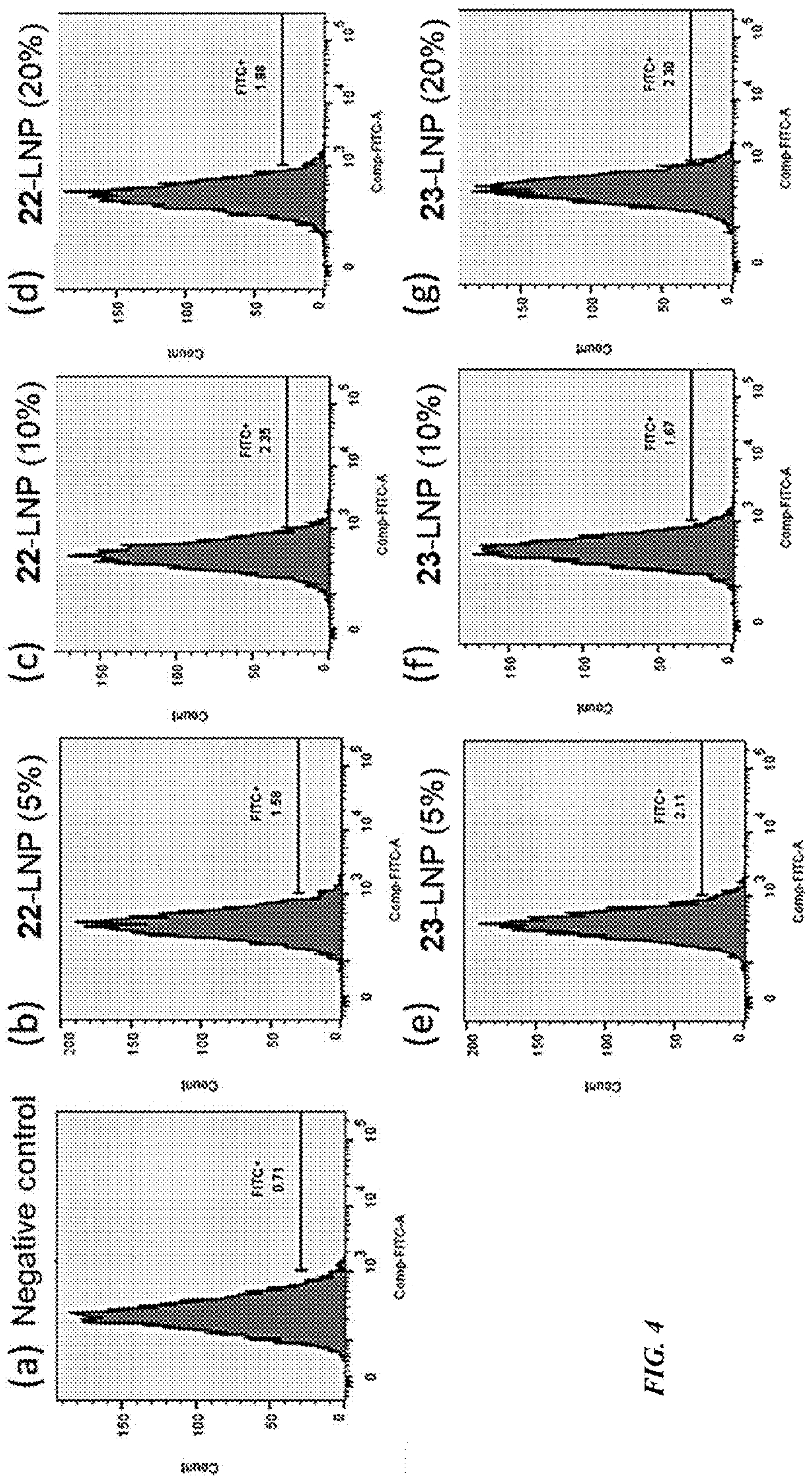
FIG. 4 provides a graphic representation showing the FACS analysis results demonstrating the efficacy of the exemplary novel dendritic cell-targeting formulations of the present disclosure. The experiments showed the transfection of the targeting formulations BDMCs compared with LNPs without the compound of the present disclosure. The FITC+ values shown in the figures are fluorescent intensities in arbitrary units (A.U.). 22-LNP represents the targeting formulation made using compound 22 of the present disclosure, and the percentage in parentheses indicates the molar ratio of compound 22. Likewise, 23-LNP represents the targeting formulation made using compound 23 of the present disclosure, and the percentage in parentheses indicates the molar ratio of compound 23. The negative control was an LNP formed without using the present disclosure's novel targeting compound/formulation (i.e., "traditional LNP" as described herein).

Results. The FACS results are shown in FIG. 3 and FIG. 4 and the table below. LNPs made using the compounds of the present disclosure at different molar ratios all showed higher uptake than the negative control ("traditional" LNP without using the compound of the present disclosure). The data also confirms that the LNPs of the present disclosure not only can deliver the payload into the targeted cells but also can transfect and allow the targeted cells to express the payload. Given the higher specificity towards the targeted cells, the transfection signals detected from the groups using the LNPs of the present disclosures were also significantly higher than those detected from the traditional group. This result suggests that using the LNPs of the present disclosure allows a lower dosage of the payload for a similar outcome.

Table showing the results of uptake and transfection (arbitrary unit of the FITC signals)

| Experiment 3-2 | L5 the compound of the present disclosure | FITC signal intensity (A.U.) derived from uptake | FITC signal intensity (A.U.) derived from transfection |
|---|---|---|---|
| Example 1 | 5 mol % Compound 22 | 12.0 | 1.58 |
| Example 2 | 10 mol % Compound 22 | 6.11 | 2.35 |
| Example 3 | 20 mol % Compound 22 | 11.0 | 1.88 |
| Example 4 | 5 mol % Compound 23 | 13.4 | 2.11 |
| Example 5 | 10 mol % Compound 23 | 13.6 | 1.67 |
| Example 6 | 20 mol % Compound 23 | 23.6 | 2.30 |
| Example 7 (control) | None (traditional LNP) | 0.38 | 0.71 |

Experiment 3-3

To assess the binding of DC-SIGN to the LNPs of the present disclosure, ELISA plates were coated with exemplary LNPs in PBS at 4° C. overnight, respectively. The plates were incubated with diluted DC-SIGN ECD (15 to 0.075 nM in HEPES buffer containing 20 mM HEPES, 150 mM NaCl, 10 mM $CaCl_2$, 0.1% BSA) at pH 7.4, 6.0, and 5.0 for 1 hour at room temperature. The bound DC-SIGN ECD was detected using HRP-conjugated anti-DC-SIGN (B2) IgG antibody (Santa Cruz Biotechnology). After 1 hour of incubation at room temperature, the plates were treated with tetramethlybenzidine (TMB) for 10 min. The optical density was measured at 450 nm after adding 0.5 M sulfuric acid to the plates using a microplate reader. The apparent Kd was calculated using a nonlinear regression curve fit for total binding using GraphPad Prism.

Example 4: In Vivo Delivery of Luciferase mRNA-LNP

This experiment tested the targeted delivery of the LNPs of the present disclosure (shown in the table below) in vivo. The LNPs tested in this experiment carried mRNA encoding luciferase. Mice were injected intravenously with the LNPs (200 μL) and maintained for one hour or six hours before In vivo Imaging System (IVIS®) measurement. For the IVIS measurement, the animals were first anesthetized using the rodent anesthesia system with isoflurane (2.5% (vol/vol) in 0.2 L/min 02 flow). Then, the animals were injected intravenously with D-luciferin solution (dissolved in 1×PBS; 150 mg/kg body weight). After 3 minutes from the injection, the animals were scanned using the IVIS imaging system (data not shown). After imaging, the animals were euthanized in a $CO_2$ chamber. The organs (heart, lungs, liver, spleen, kidneys, and lymph nodes) of the animals were collected, and the luminescence was detected and quantified using the IVIS system.

Table of the exemplary LNPs tested in this experiment.

| Example | L1: Ionizable lipid | L2: Phosphatidylcholine | L3: Cholesterol | L4: PEG-Lipid | L5 the compound of the present disclosure |
|---|---|---|---|---|---|
| 1 | 45 mol % | 9 mol % | 34.5 mol % | 1.5 mol % | 10 mol % Compound 22 |
| 2 | 45 mol % | 9 mol % | 34.5 mol % | 1.5 mol % | 10 mol % Compound 12 |
| 7 (control) | 50 mol % | 10 mol % | 38.5 mol % | 1.5 mol % | none |

Figure 5:
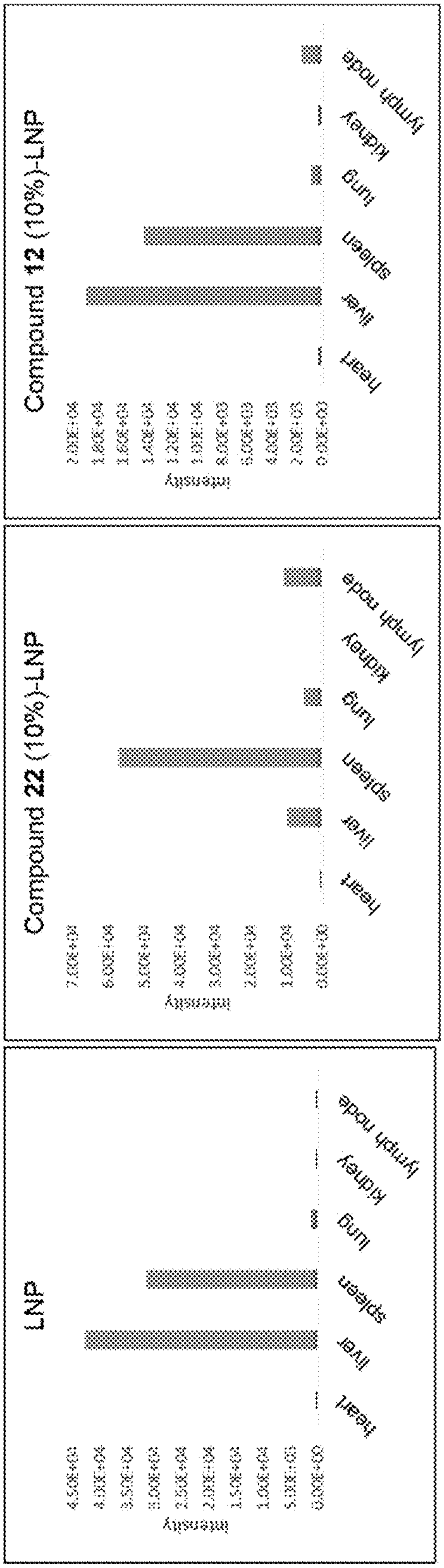
FIG. 5 provides a graphic representation demonstrating the targeting efficacy and specificity of the exemplary formulation based on the distribution of the targeting LNPs in an animal model. The LNPs carried an mRNA configured to encode a luciferase in the targeted cells of the tested animals. The assay would generate detectable luminescence if the LNPs successfully transfect cells and the cells express the luciferase. The results clearly showed tissue-specific targeting of spleen and lymph tissue by the exemplary targeting formulation, thereby providing supporting evidence of immune cell (e.g., dendritic cell) specificity.
Figure 6:
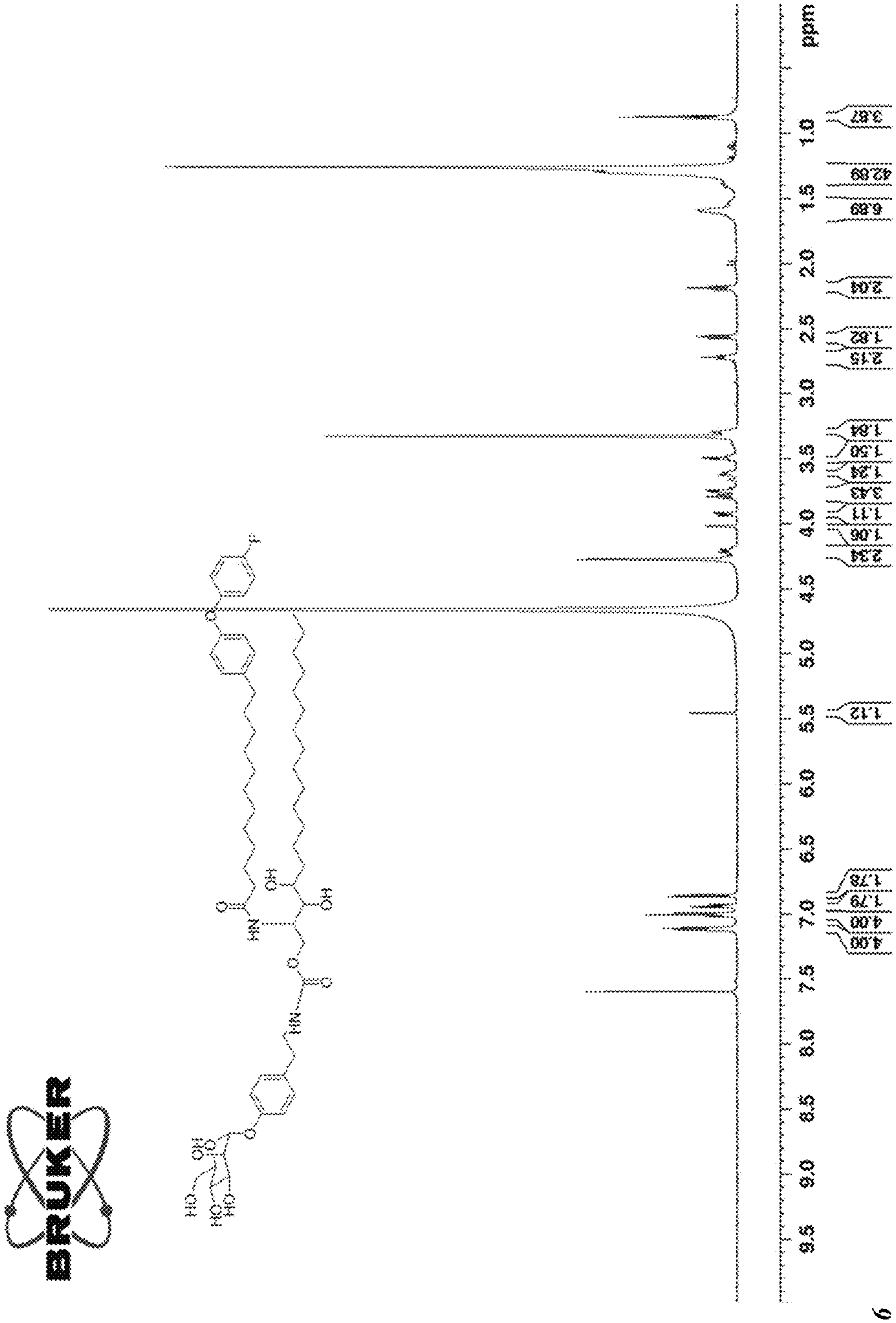
FIG. 6 shows the $^{1}H$ NMR spectrum of compound 12 of the present disclosure.
Figure 7:
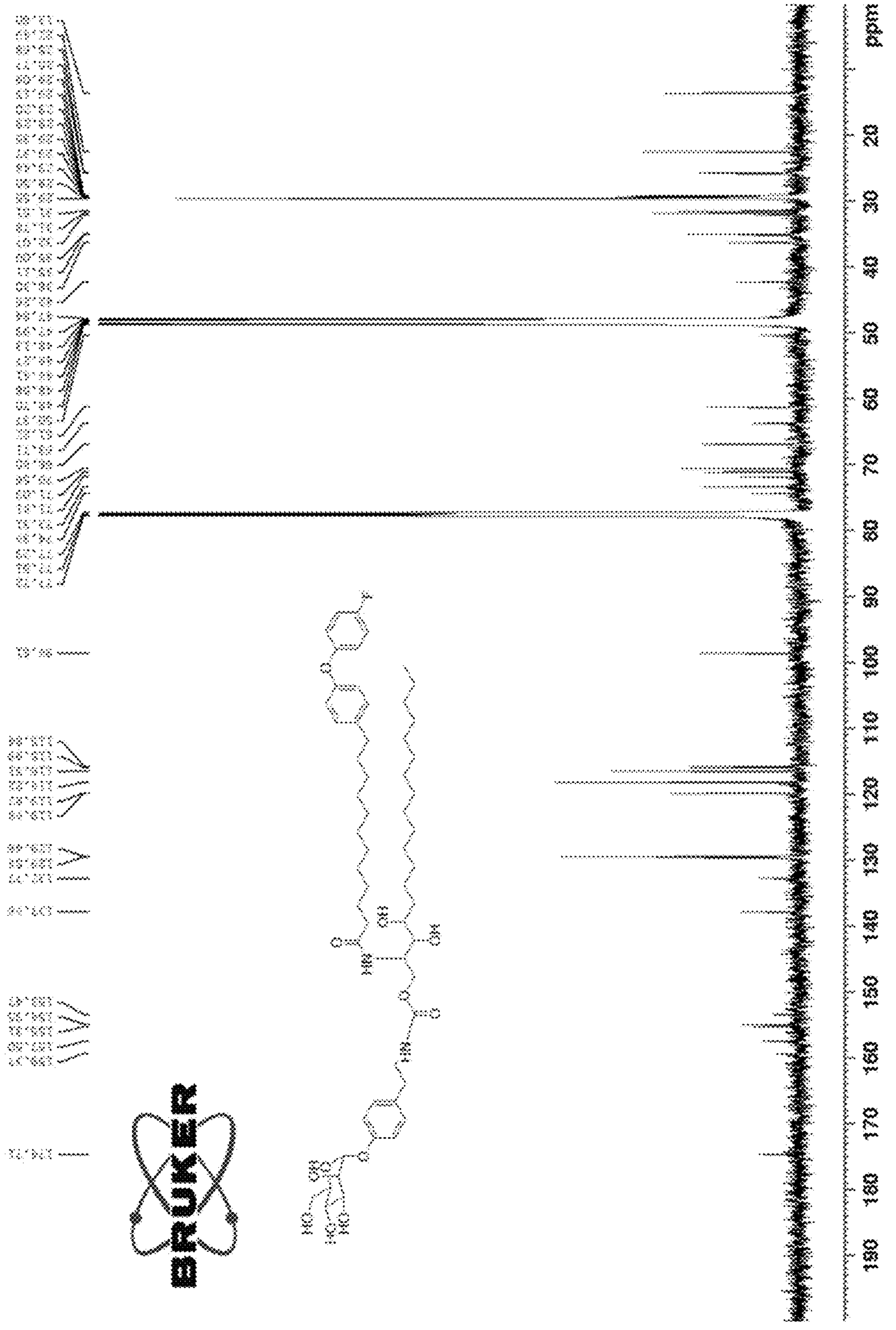
FIG. 7 shows the $^{13}C$ NMR spectrum of compound 12 of the present disclosure.
Figure 8:
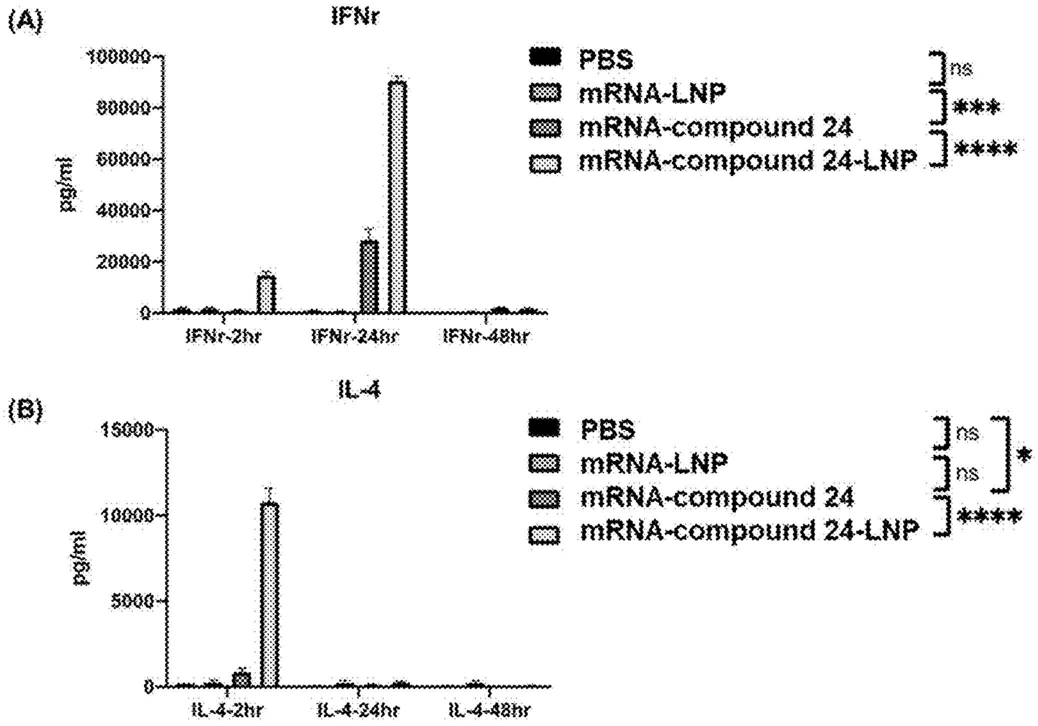
FIG. 8 presents bar charts showing the IFNγ (A) and IL-4 (B) induction by the exemplary targeting LNPs formulation according to an embodiment of the present disclosure in vivo. The sera were collected from experimental animals 2 hours, 24 hours, and 48 hours after administration.

Results. The results (FIG. 5) show that both compound 22-LNP and compound 12-LNP tend to accumulate in spleens and lymph nodes. While compound 12-LNP also accumulated in livers, compound 22-LNP showed high-level specificities targeting spleens and lymph nodes. The results demonstrate the targeting delivery functionalities of the lipid nanoparticle formulations of the present disclosure, which matches the observations of the experiments above.

Example 6: Immunization

Animals. Balb/c mice (8 weeks) were purchased from the National Laboratory Animal Center, Taiwan. All the mice were maintained in a specific pathogen-free environment. Eight-week-old Balb/c mice were immunized i.m. twice at 2-week intervals. Each vaccination contains PBS (100 1). Sera collected from immunized mice were subjected to ELISA analysis 10 days after the last immunization. The experimental protocol was approved by Academia *Sinica*'s Institutional Animal Care and Utilization Committee (approval no. 22-08-1901).

LNPs. For neutralization assay, LNPs, according to an embodiment of the present disclosure, were prepared for this experiment. Two control LNPs were also prepared to compare the performance of the present disclosure's LNPs. The first control LNP was formed using SM-102 and DSPC ("L1+L2") without using the compound of the present disclosure. The second control LNP was a Moderna product for Spikevax ("LNP(M)"). All tested LNPs carried mRNA cargo encoding SARC-CoV-2 spike protein. For IgG titer assay, LNPs of the present disclosure were prepared to carry either a mRNA encoding wild-type SARC-CoV-2 spike protein or a mRNA encoding wild-type SARC-CoV-2 spike protein with low-sugar modification.

Animal Immunizations. BALB/c mice aged 6 to 8 wk old (n=5) were immunized intramuscularly with 15 g of LNPs in phosphate-buffered saline (PBS). Animals were immunized at week 0 and boosted with a second vaccination at week 2, and serum samples were collected from each mouse 2 weeks after the second immunization.

Pseudovirus neutralization assay. Pseudovirus was constructed by the RNAi Core Facility at Academia Sinica using a procedure similar to that described previously. Briefly, the pseudotyped lentivirus carrying SARS-CoV-2 spike protein was generated by transiently transfecting HEK-293T cells with pCMV-AR8.91, pLAS2w.Fluc.Ppuro. HEK-293T cells were seeded one day before transfection, and indicated plasmids were delivered into cells using TransITR-LT1 transfection reagent (Mirus). The culture medium was refreshed at 16 hours and harvested at 48 hours and 72 hours post-transfection. Cell debris was removed by centrifugation at 4,000×g for 10 min, and the supernatant was passed through a 0.45-μm syringe filter (Pall Corporation). The pseudotyped lentivirus was aliquot and then stored at −80° C. To estimate the lentiviral titer by AlarmaBlue assay (Thermo Scientific), The transduction unit (TU) of SARS-CoV-2 pseudotyped lentivirus was estimated by using cell viability assay in responded to the limited dilution of lentivirus. In brief, HEK-293T cells stably expressing the human ACE2 gene were plated on a 96-well plate one day before lentivirus transduction. For the tittering pseudotyped lentivirus, different amounts of lentivirus were added into the culture medium containing polybrene (final concentration 8 μg/ml). Spin infection was carried out at 1,100×g in a 96-well plate for 30 minutes at 37° C. After incubating cells at 37° C. for 16 hr, the culture medium containing virus and polybrene was removed and replaced with fresh complete DMEM containing 2.5 g/ml puromycin. After treating puromycin for 48 hrs, the culture media was removed, and the cell viability was detected using 10% AlamarBlue reagents according to the manufacturer's instructions. The survival rate of uninfected cells (without puromycin treatment) was set as 100%. The virus titer (transduction units) was determined by plotting the survival cells versus the diluted viral dose. For neutralization assay, heat-inactivated sera or antibodies were serially diluted and incubated with 1,000 TU of SARS-CoV-2 pseudotyped lentivirus in DMEM for 1 h at 37° C. The mixture was then inoculated with 10,000 HEK-293T cells stably expressing the human ACE2 gene in a 96-well plate. The culture medium was replaced with fresh complete DMEM (supplemented with 10% FBS and 100 U/mL penicillin/streptomycin) at 16 h postinfection and continuously cultured for another 48 h. The expression level of the luciferase gene was determined by using the Bright-Glo Luciferase Assay System (Promega). The relative light unit (RLU) was detected by Tecan i-control (Infinite 500). The percentage of inhibition was calculated as the ratio of RLU reduction in the presence of diluted serum to the RLU value of no serum control using the formula ($RLU^{control}$-$RLU^{Serum}$)/RLU control.

Measurement of serum IgG titer. ELISA was used to determine the IgG titer of the mouse serum. The wells of a 96-well ELISA plate (Greiner Bio-One) were coated with 100 ng SARS-CoV-2 spike protein (ACROBiosystems, wild-type, Delta, or Omicron, respectively) in 100 mM sodium bicarbonate pH 8.8 at 4° C. overnight. The wells were blocked with 200 μl 5% skim milk in 1×PBS at 37° C. for 1 hour and washed with 200 μl PBST (1×PBS, 0.05% TWEEN 20®, pH 7.4) three times. Mice serum samples with 2-fold serial dilution were added into wells for incubation at 37° C. for 2 hours and washed with 200 μl PBST six times. The wells were incubated with 100 μl HRP conjugated anti-mouse secondary antibody (1:10000, in PBS) at 37° C. for 1 hour and washed with 200 μl PBST six times. 100 μl horseradish peroxidase substrate (1-Step™ Ultra TMB-ELISA Substrate Solution) (Thermo Scientific™) was added into wells, followed by 100 μl 1M $H_2SO_4$. After incubation for 30 minutes, absorbance (OD 450 nm) was measured using SpectraMax M5.

Figure 9:
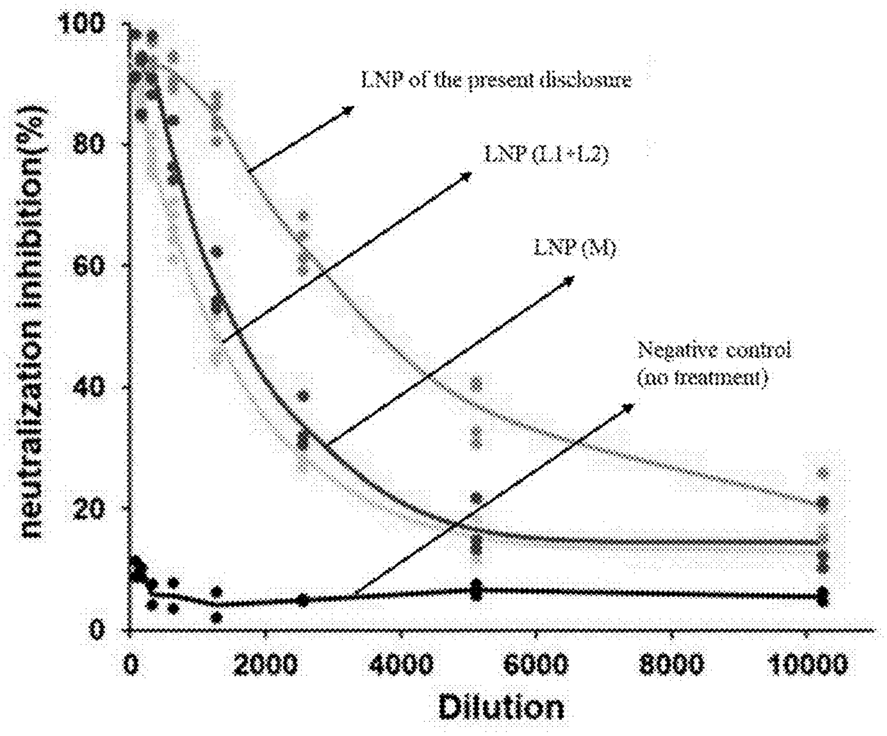
FIG. 9 shows a graphic representation demonstrating the neutralization inhibitory effects of the exemplary LNPs of the present disclosure compared to control LNPs. The neutralization inhibition was evaluated against different dilution factors to show the difference between samples.

Results. FIG. 9 shows that all tested LNPs carrying the mRNA cargo were able to deliver and express the mRNA in vivo, thereby invoking immune responses that resulted in neutralization inhibition. Nevertheless, the inhibitory effect of those tested LNPs differed as the dilution factor increased. Both L1+L2 LNP and LNP (M) only showed a slightly higher inhibitory effect at 1:5000 dilution compared with the negative control, but the LNP of the present disclosure maintained around 40% inhibitory effect. The data demonstrates that the LNP of the present disclosure was able to invoke immune responses at a much lower concentration than other LNPs tested in this experiment.

Figure 10:
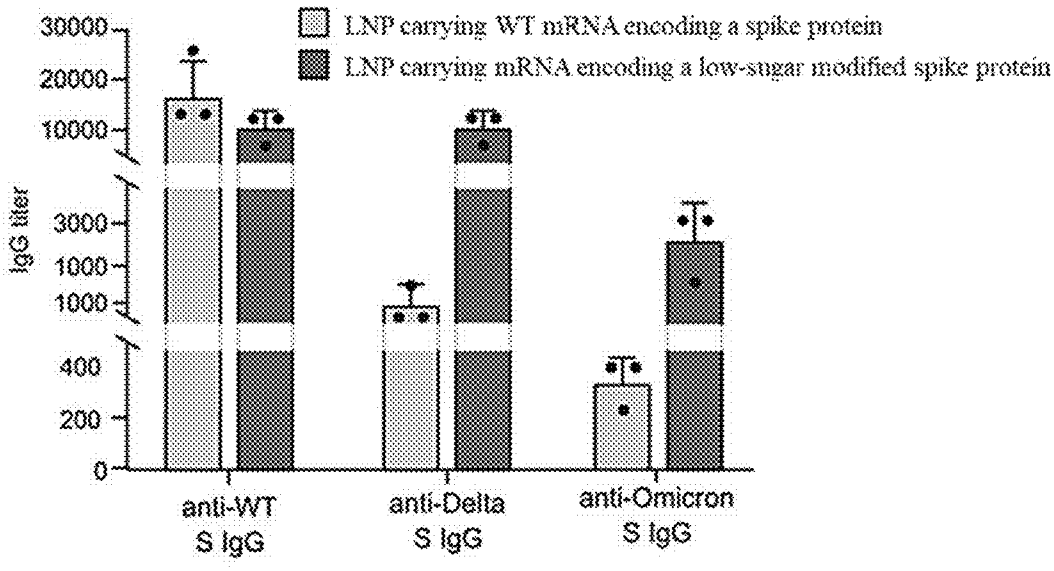
FIG. 10 provides a bar chart demonstrating that the exemplary LNPs according to the present disclosure, carrying mRNA encoding wide-type spike protein, were able to invoke IgG production in vivo against wild-type virus and Delta and Omicron strains thereof.

FIG. 10 verifies that the LNPs of the present disclosure were capable of inducing antigen-specific IgG in vivo. The LNP, carrying mRNA encoding wide-type spike protein, induced IgGs that were still able to recognize the spike proteins of both the Delta variant and Omicron variant at a good level. The data shows that the targeted delivery feature of the LNP can at least partially overcome the immune escape due to the spike protein variations between variants.

Furthermore, it was observed that LNP carrying wild-type SARS-CoV-2 spike protein-encoding mRNA ("WT LNP") and LNP carrying mRNA encoding a low-sugar modified spike protein ("low-sugar LNP") induced comparable IgG titers against wide-type viruses, the WT LNP had lower IgG titers against the Delta and Omicron strains, suggesting an immune escape. In contrast, the low-sugar LNP maintains a high level of IgG titers against the two variant strains. The results demonstrate that removing glycan shields improves the immunogenicity of the LNP formulations.

Figure 11:
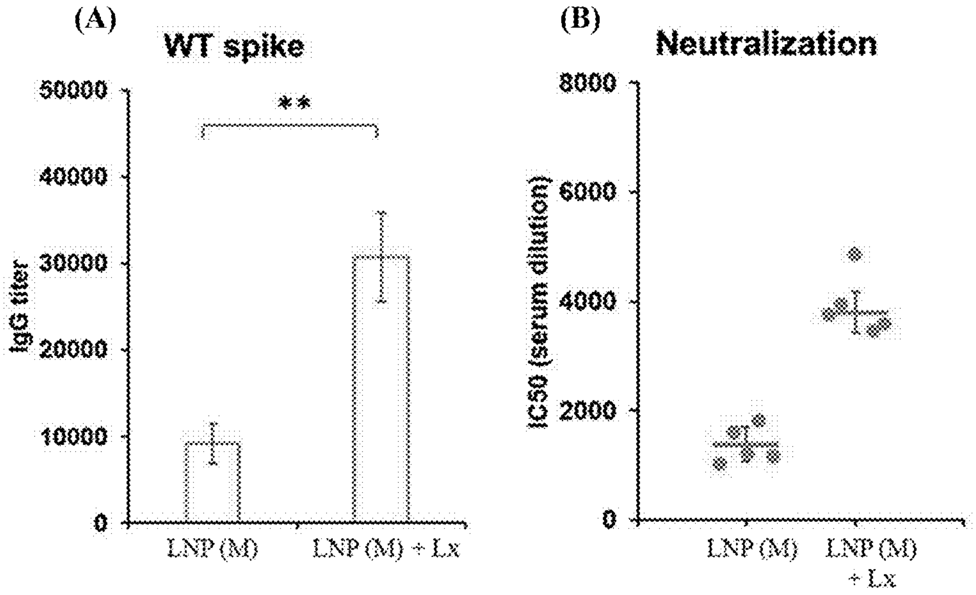
FIG. 11 shows a comparative bar chart demonstrating the IgG titer (A) and neutralization ability (B) induced respectively by commercially available LNPs vs. LNP formulation formulated based on, and/or constructed with, exemplary compounds according to embodiments of the present disclosure. Both LNPs carried mRNA encoding a wide-type spike protein.

FIG. 11 shows the results of an additional experiment. In this experiment, a Moderna LNP was prepared using Moderna's proprietary formulation. In addition, LNP made using the Moderna formulation and adding a compound of the present disclosure was also prepared to test whether the compound of the present disclosure improves the performance of the Moderna formulation. Animals were administered with the LNPs, and IgG titer assay and neutralization assay were all performed as described above in this example. The results demonstrate that the compound of the present disclosure increased the spike protein-specific IgGs. The serum obtained from mice administered with the LNP of the present disclosure's compound also exhibited better neutralization. This experiment confirmed the targeted delivery feature of the compound of the present disclosure and verified that it can be applied to commercially available LNP formulations.

Exemplary Embodiments

Embodiment 1. A compound for forming a lipid nanoparticle, wherein the component comprises the formula:

Formula 1

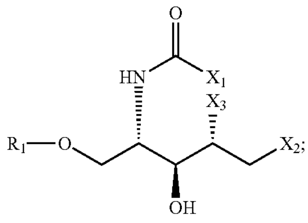

or

Formula 2

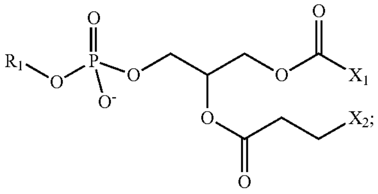

wherein $R_1$ comprises a substituted or non-substituted glycosyl group; wherein $X_1$ and $X_2$ are each independently hydrogen, $C_{1-30}$ alkyl, $C_{1-30}$ alkenyl, $C_{1-30}$ alkynyl, aryl, aryloxy, or a substituted version thereof, or $—(CH_2)nX_4$, n is 0 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof; and wherein $X_3$ is hydrogen, $C_{1-6}$ alkyl, or hydroxyl.

Embodiment 2. The compound of embodiment 1, wherein $R_1$ comprises a formula of $R_2—R_A—$, wherein $R_A$ is an attachment group and $R_2$ is the substituted or non-substituted glycosyl group, and wherein the attachment group comprises an aryl, an alkyl, an amide, an alkylamide, a substituted version thereof, a combination thereof, or a covalent bond.

Embodiment 3. The compound of embodiment 2, wherein $R_A$ comprises the aryl having 0 to 3 substituents, wherein the substituent is $C_{1-6}$ alkyl, halide, or $C_{1-6}$ alkyl halide.

Embodiment 4. The compound of embodiment 3, wherein $R_A$ further comprises a polyethylene glycol (PEG) moiety having 2 to 72 $(OCH_2CH_2)$ subunits.

Embodiment 5. The copolymer of embodiment 3 or embodiment 4, wherein the PEG moiety is linear.

Embodiment 6. The compound of any one of embodiments 1 to 5, wherein the glycosyl group comprises mannoside, fucoside, or a combination thereof.

Embodiment 7. The compound of any one of embodiments 1 to 6, wherein the glycosyl group comprises a terminal mannoside, a terminal fucoside, or both.

Embodiment 8. The compound of any one of embodiments 1 to 7, wherein the glycosyl group comprises a mono-mannoside, a di-mannoside, or a tri-mannoside.

Embodiment 9. The compound of embodiment 8, wherein the tri-mannoside is a linear or branched tri-mannoside.

Embodiment 10. The compound of embodiment 9, wherein the branched tri-mannoside is a α-1,3-α-1,6-tri-mannoside.

Embodiment 11. The compound of any one of embodiments 1 to 10, wherein $R_1$ is a substituted glycosyl group.

Embodiment 12. The compound of embodiment 11, wherein the glycosyl group comprises 1 to 6 substituents, wherein the substituent is $C_{1-6}$ alkyl, $C_{1-6}$ alkenyl, halogen, $C_{1-6}$ alkyl halide, $C_{1-6}$ alkoxy, amine, nitro, $C_{1-6}$ alkyl amine, amide, azido, aryl, cycloalkyl, heterocycloalkyl, sulfite, or a substituted version thereof, or a combination thereof.

Embodiment 13. The compound of embodiment 12, wherein the substituent of the glycosyl group is selected from the group consisting of aryl, 5-membered cycloalkyl, 6-membered cycloalkyl, 5-membered heterocycloalkyl, and 6-membered heterocycloalkyl, and a substituted version thereof, which comprises 1 to 6 substituents selected from the group consisting of $C_{1-6}$ alkyl, halogen, $C_{1-6}$ alkyl halide, $C_{1-6}$ alkoxy, amine, nitro, $C_{1-6}$ alkyl amine, amide, azido, carboxyl, hydroxyl, aryl, cycloalkyl, heterocycloalkyl, or a substituted version thereof, or a combination thereof.

Embodiment 14. The compound of embodiment 12 or embodiment 13, wherein the substituent of the glycosyl group is a substituted or non-substituted aryl, optionally the substituent of the glycosyl group is a phenyl substituted with OH, $CH_3$, $NH_2$, $CF_3$, $OCH_3$, F, Br, Cl, $NO_2$, $N_3$, or a combination thereof.

Embodiment 15. The compound of embodiment 12 or embodiment 13, wherein the heterocycloalkyl comprises 1 to 3 heteroatoms, selected from the group consisting of O, S, and N.

Embodiment 16. The compound of any one of embodiments 1 to 15, wherein $R_1$ is selected from the group consisting of:

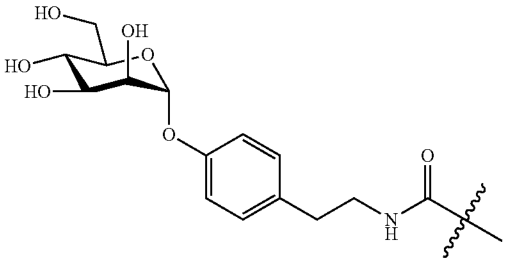
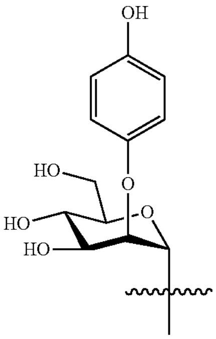
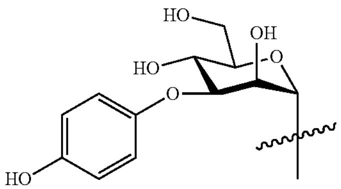
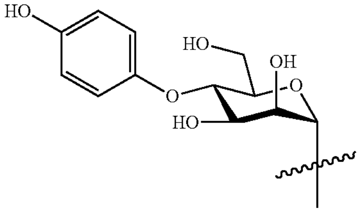
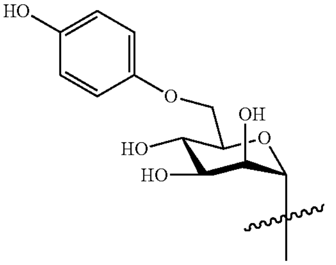
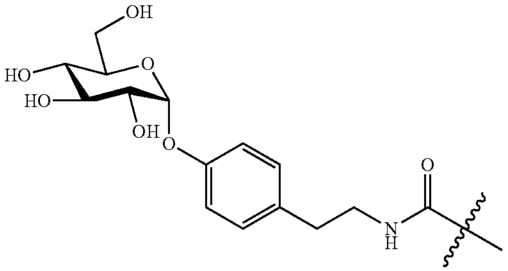
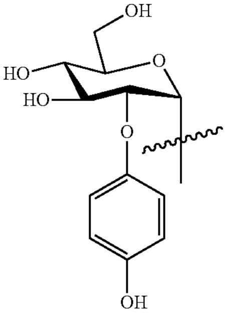
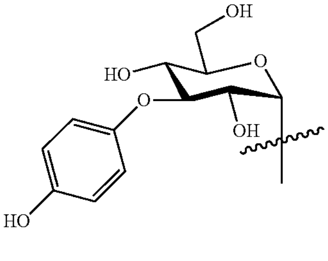
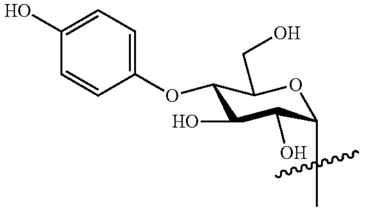
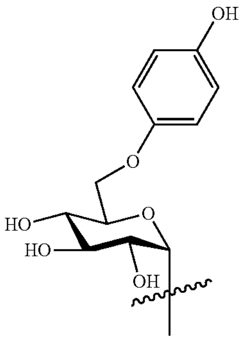
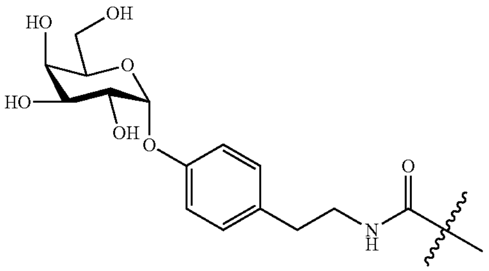

-continued
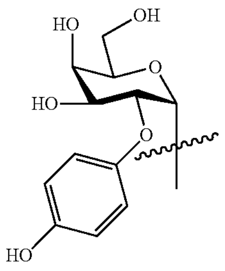
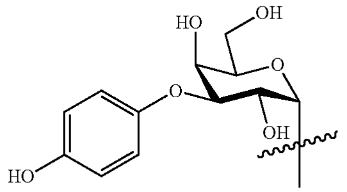
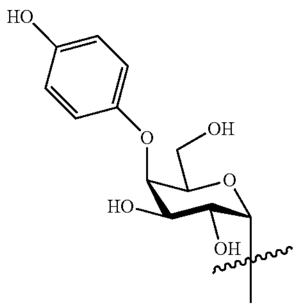
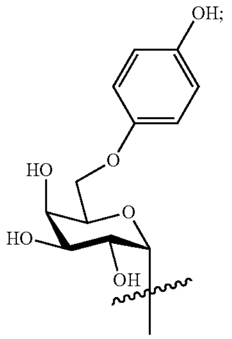
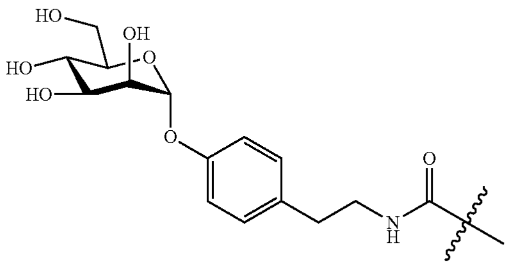
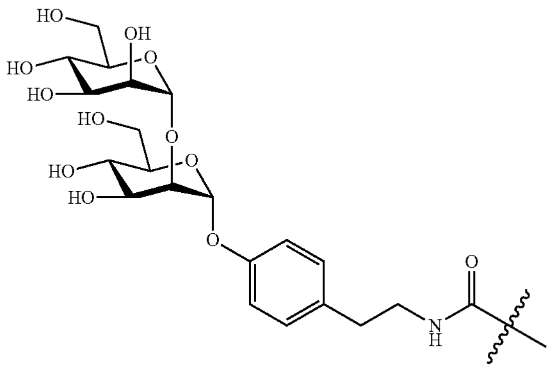
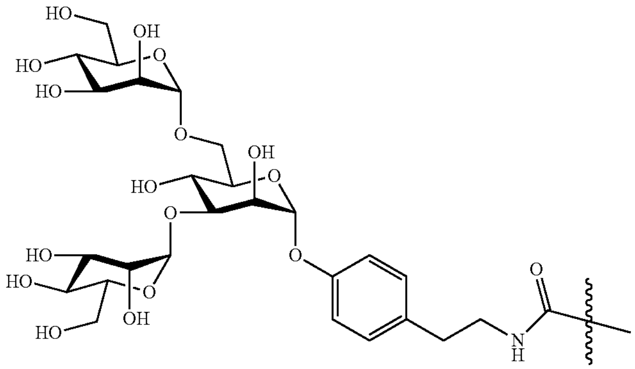
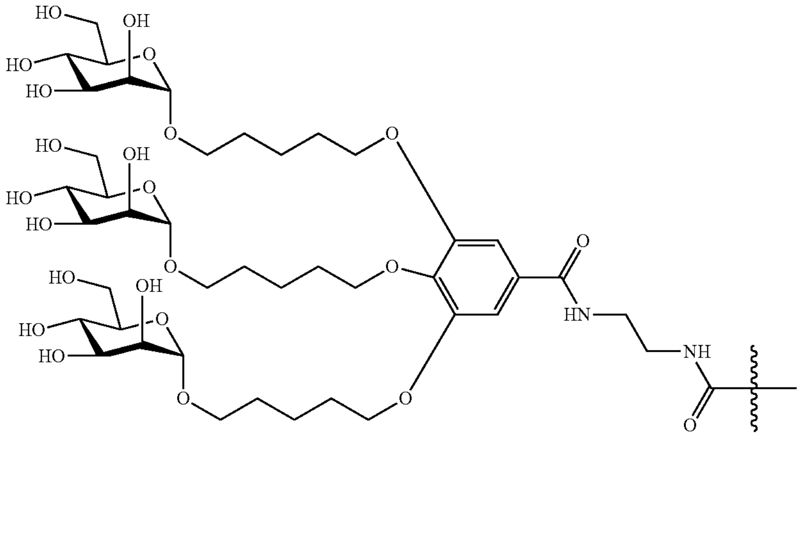

-continued
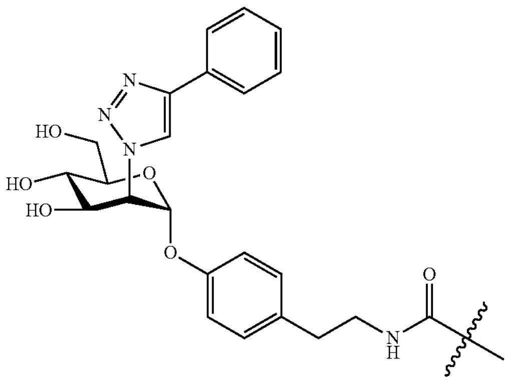
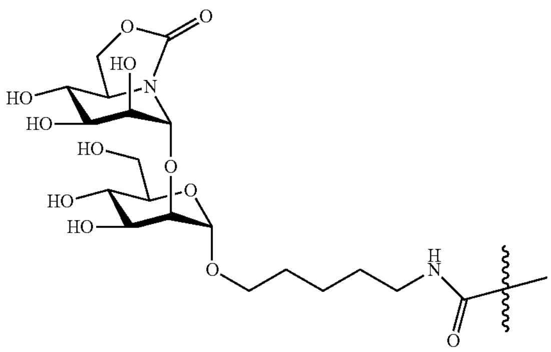
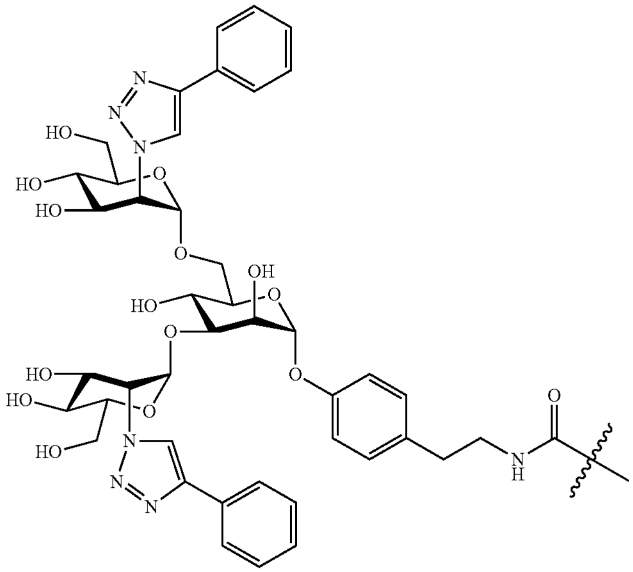
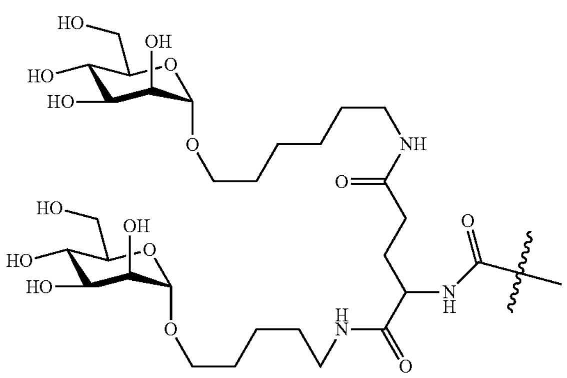
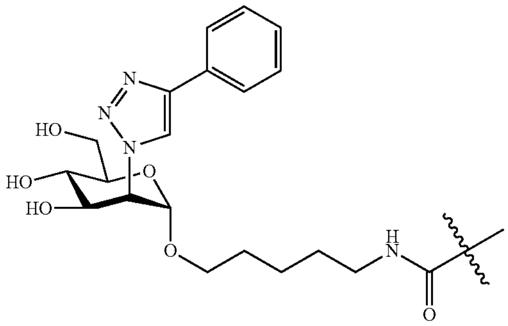
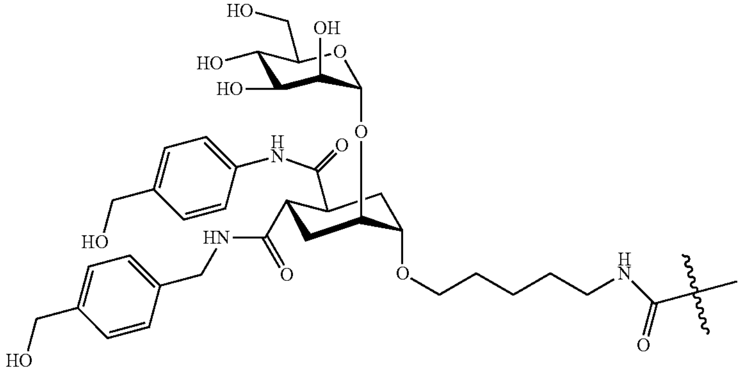

-continued
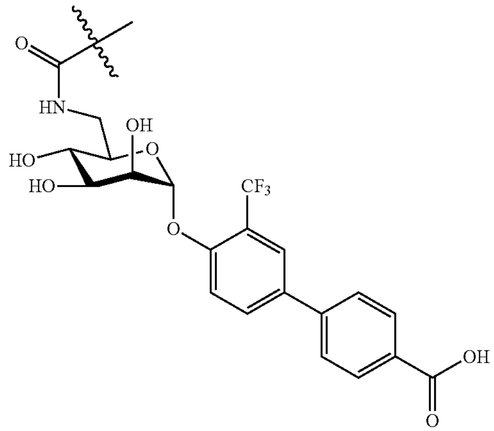
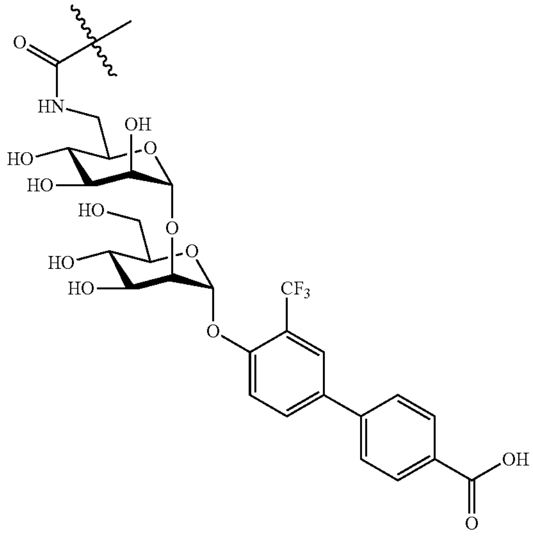
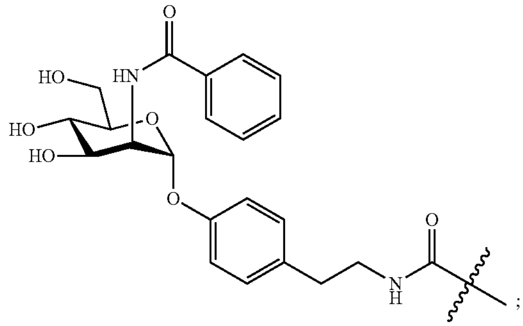
;
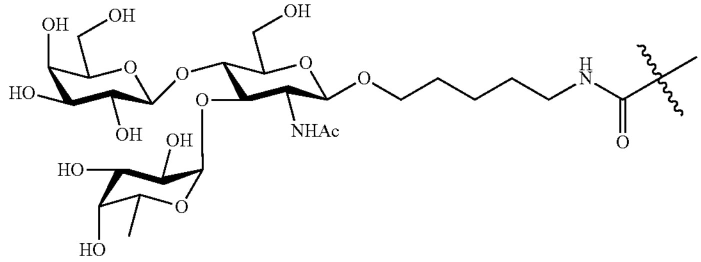
Lewis X
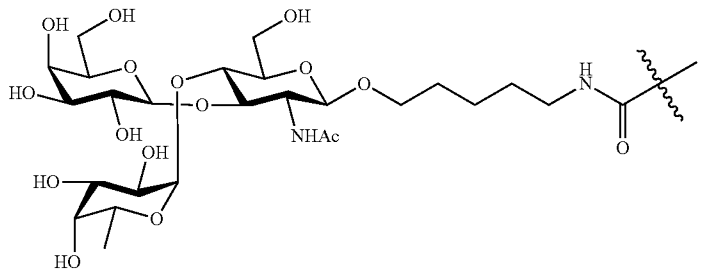
Lewis A -continued
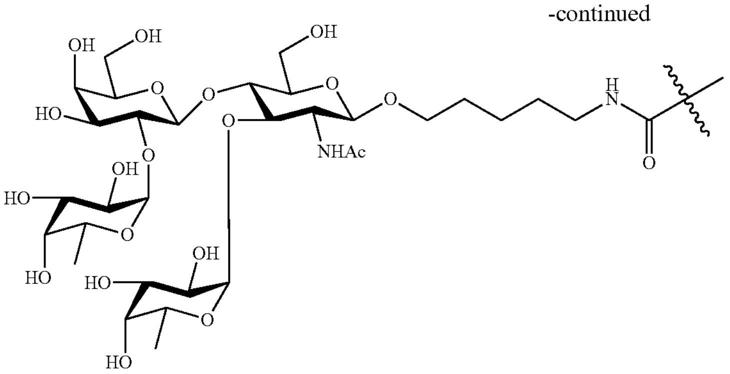
Lewis Y
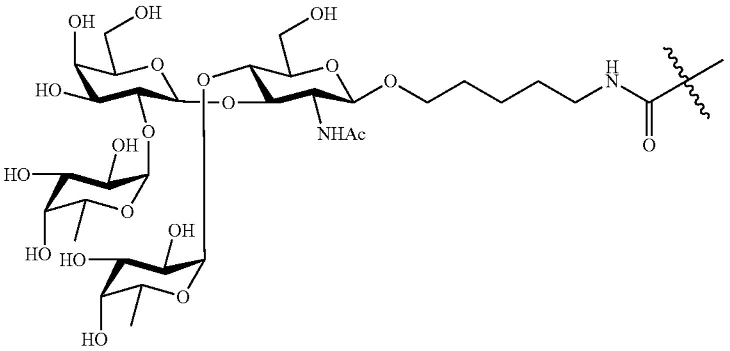
Lewis B
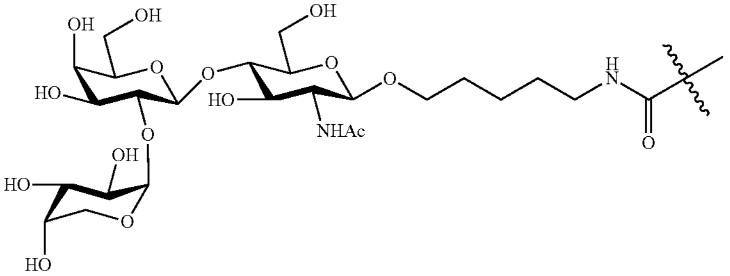
H type 2
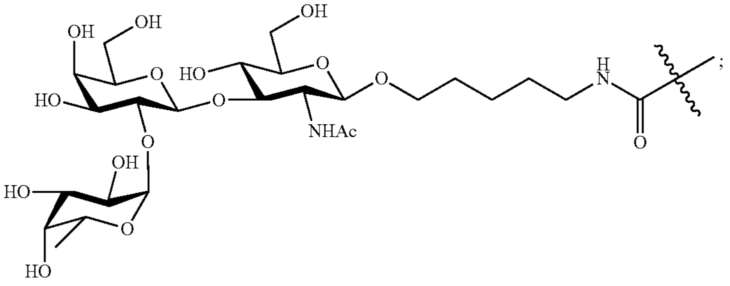
H type 1
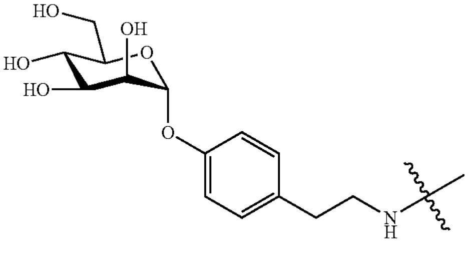
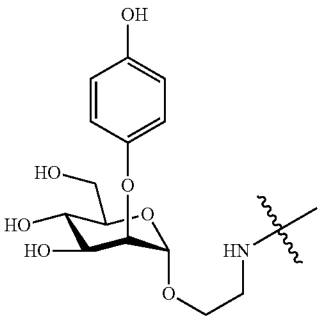

-continued
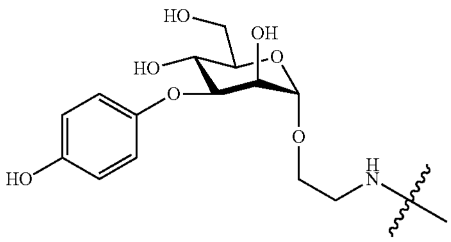
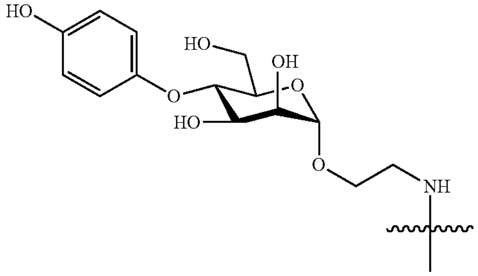
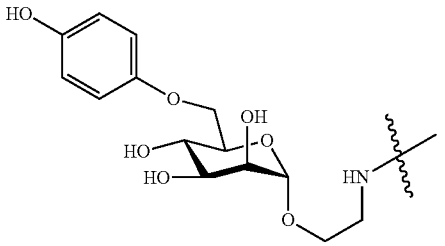
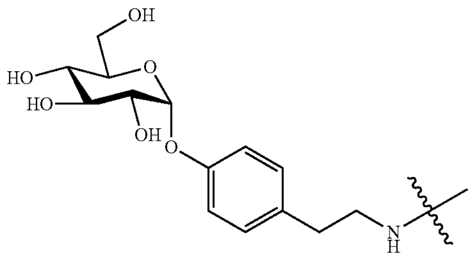
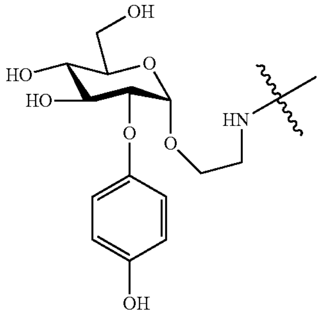
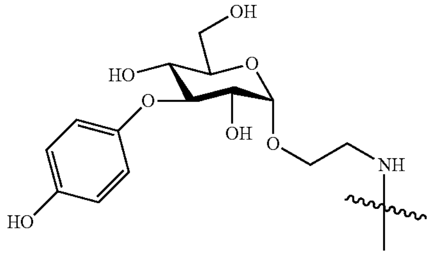
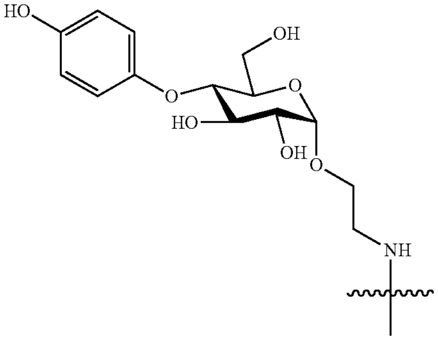
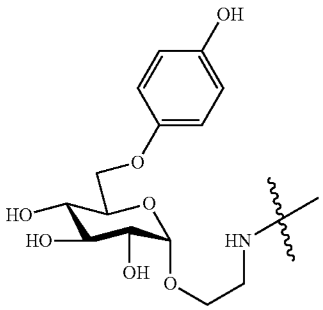
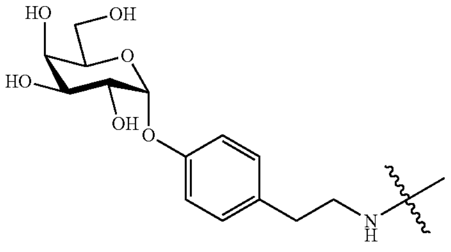
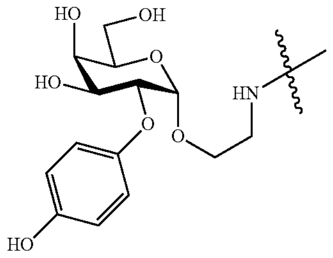
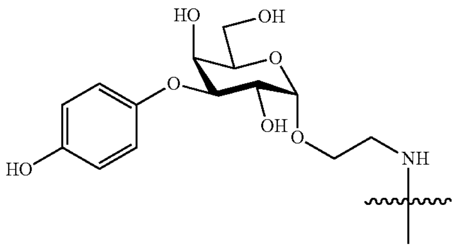
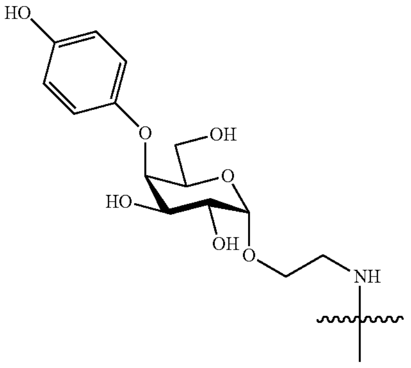

-continued
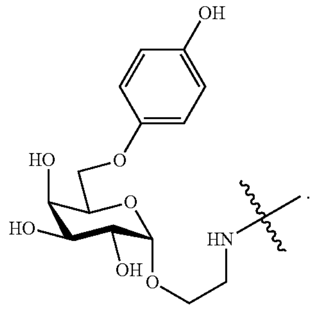
Embodiment 17. The compound of any one of embodiments 1 to 16, wherein the compound is of Formula 1.
Embodiment 18. The compound of any one of embodiments 1 to 16, wherein the compound is of Formula 2.
Embodiment 19. The compound of embodiment 18, wherein the compound is of Formula 3:
Formula 3
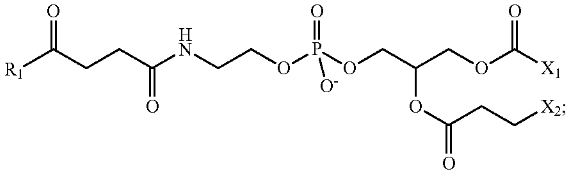
and
wherein $R_1$ is selected from the group consisting of:
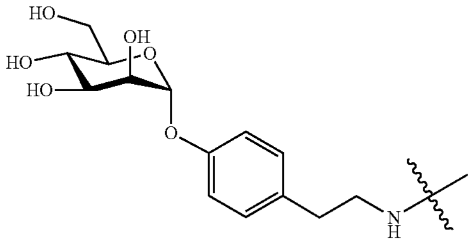
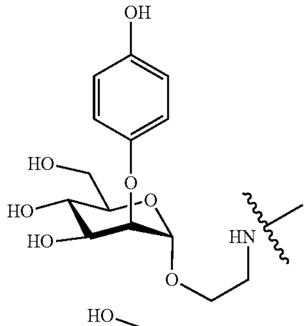
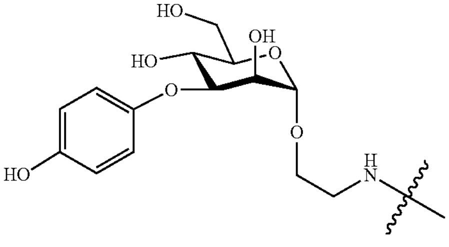
-continued
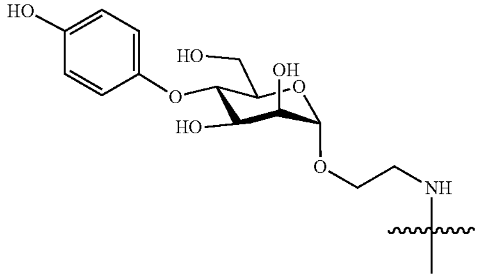
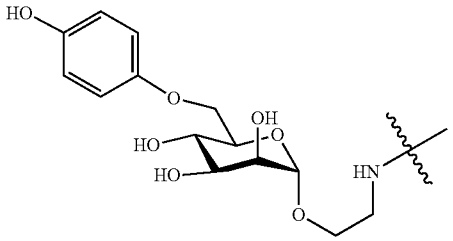
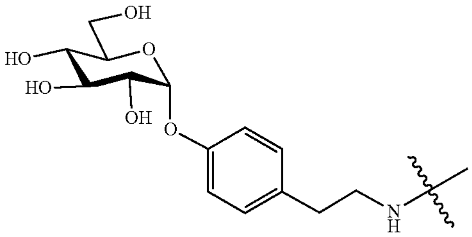
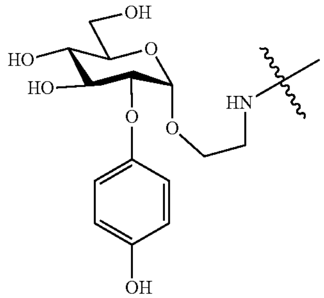
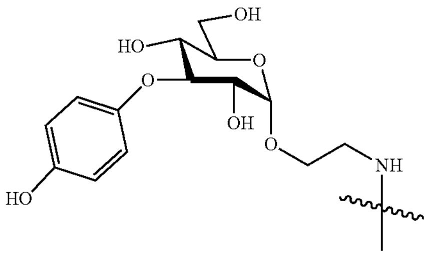

-continued

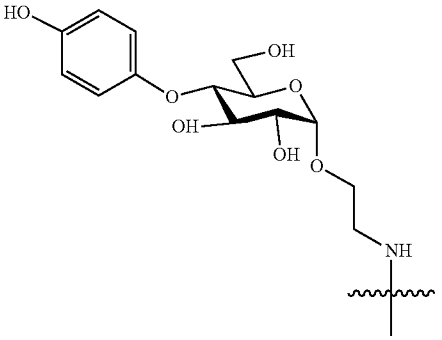

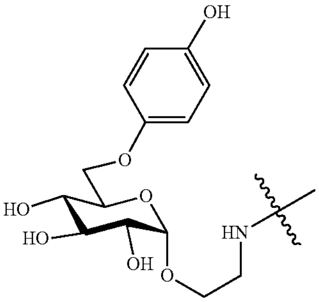

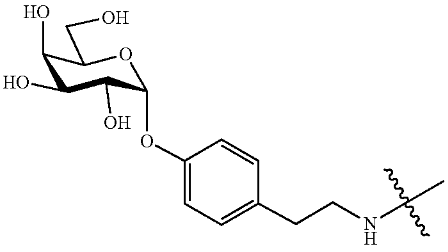

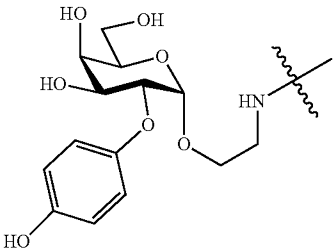

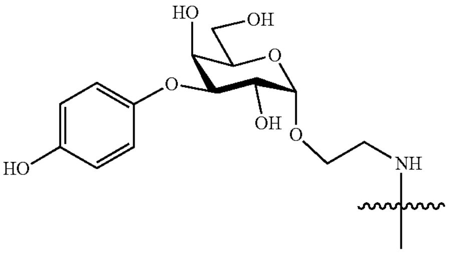

-continued

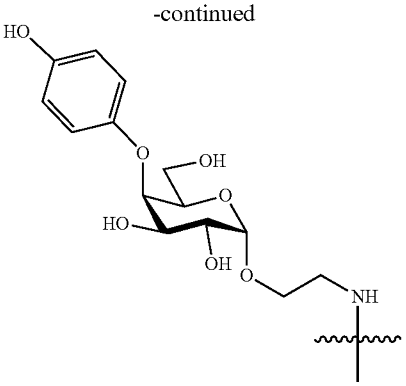

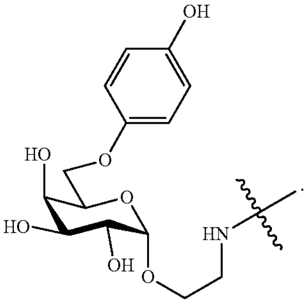

.

Embodiment 20. The compound of any one of embodiments 1 to 19, wherein at least one of $X_1$ and $X_2$ comprises a saturated hydrocarbon chain, comprising at least 2, 3, 4, 5, 6, 7, 8, 9, 10, 11, 12, 13, 14, 15, 16, 17, 18, 19, 20, 22, 24, 26, 28, or 30 carbons.

Embodiment 21. The compound of any one of embodiments 1 to 20, wherein $X_1$ and $X_2$ are each independently hydrogen, $C_{4-30}$ alkyl, $C_{4-30}$ alkenyl, $C_{4-30}$ alkynyl, aryl, aryloxy, or a substituted version thereof, or $—(CH_2)nX_4$, n is 4 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof.

Embodiment 22. The compound of embodiment 21, wherein $X_1$ and $X_2$ are each independently hydrogen, $C_{8-30}$ alkyl, $C_{8-30}$ alkenyl, $C_{8-30}$ alkynyl, aryl, aryloxy, or a substituted version thereof, or $—(CH_2)nX_4$, n is 8 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof.

Embodiment 23. The compound of any one of embodiments 1 to 22, provided that when one of $X_1$ and $X_2$ is hydrogen, the other one is not hydrogen.

Embodiment 24. The compound of any one of embodiments 1 to 23, wherein $X_4$ is an aryl, aryloxy, heterocyclic group, cycloalkyl, heterocycloalkyl, or a combination thereof, and wherein $X_4$ comprises 0 to 6 substituents, selected from the group consisting of $C_{1-6}$ alkyl, halogen, $C_{1-6}$ alkyl halogen, and $C_{1-6}$ alkoxy.

Embodiment 25. The compound of embodiment 24, wherein the substituent is $CH_3$, $CF_3$, F, or $OCH_3$.

Embodiment 26. The compound of embodiment 24 or embodiment 25, wherein $X_4$ comprises 1 to 3 substituents.

Embodiment 27. The compound of any one of embodiments 24 to 26, wherein $X_4$ is $—R_3—O—R_4$, wherein $R_3$ and $R_4$ are each independently aryl, heterocyclic group, cycloalkyl, heterocycloalkyl, each comprising 0 to 6 substituents selected from the group consisting of $C_{1-6}$ alkyl, halogen, $C_{1-6}$ alkyl halogen, and $C_{1-6}$ alkoxy.

Embodiment 28. The compound of any one of embodiments 1 to 27, wherein one of $X_1$ and $X_2$ is $C_{15-30}$ alkyl, and the other one is $-(CH_2)nX_4$.

Embodiment 29. The compound of any one of embodiments 1 to 28, wherein $X_4$ is selected from the group consisting of

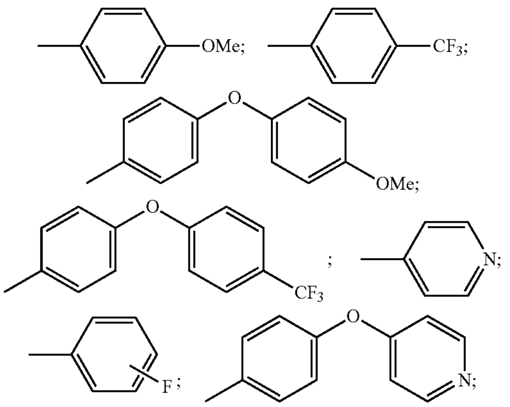

-continued

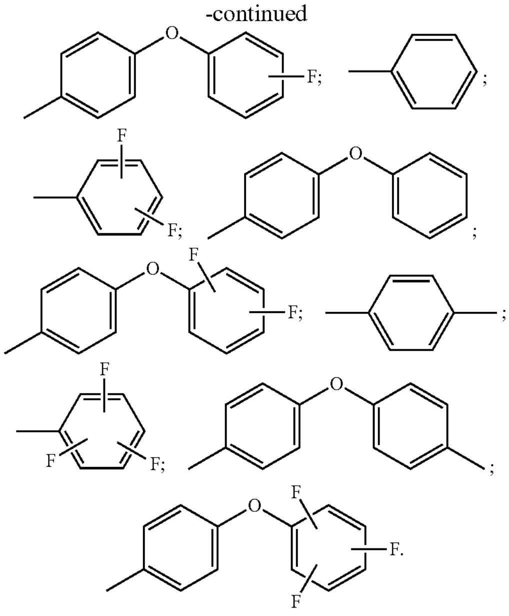

Embodiment 30. The compound of any one of embodiments 1 to 29, selected from the group consisting of:

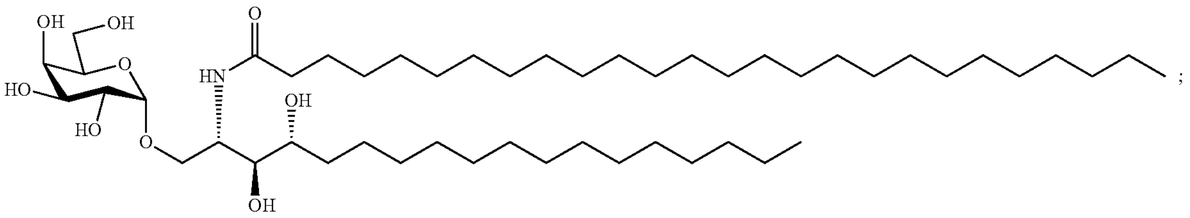

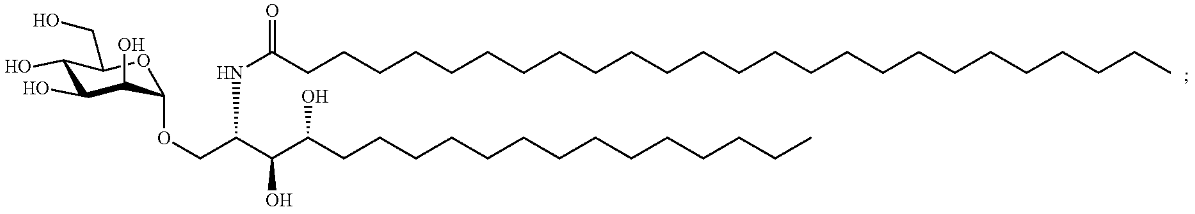

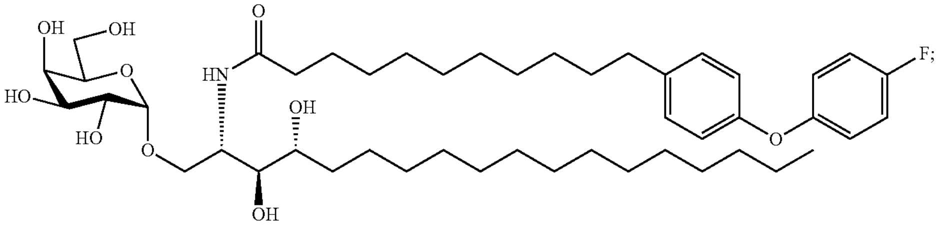

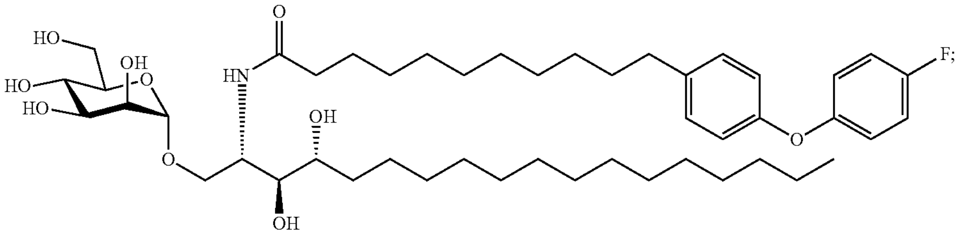

-continued
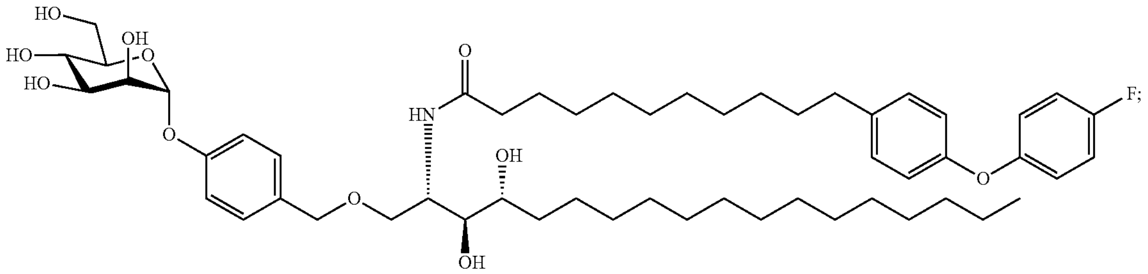
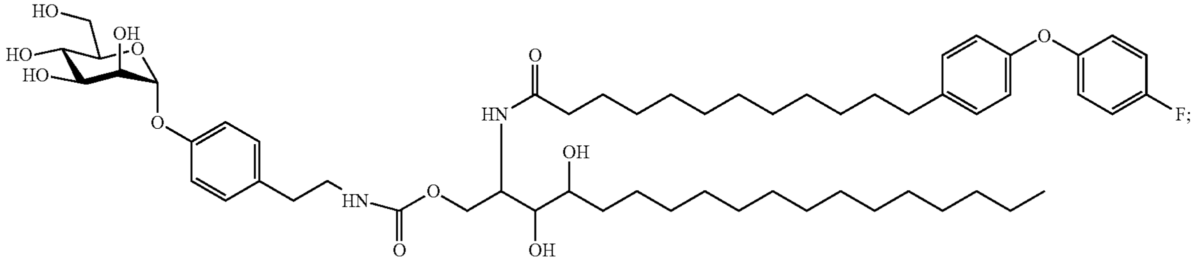
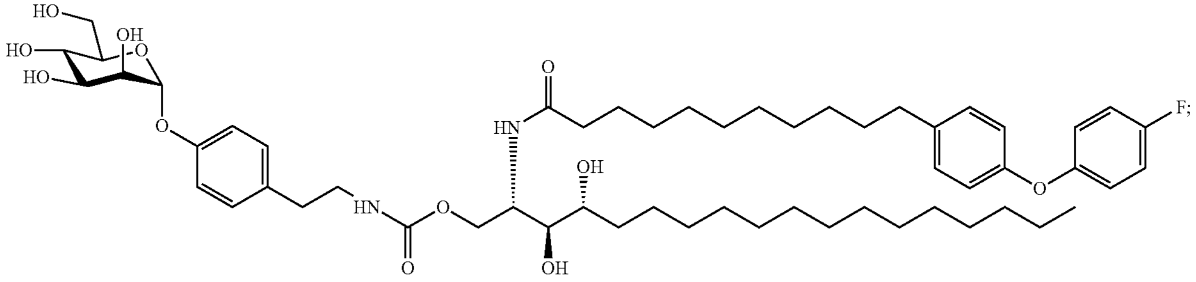
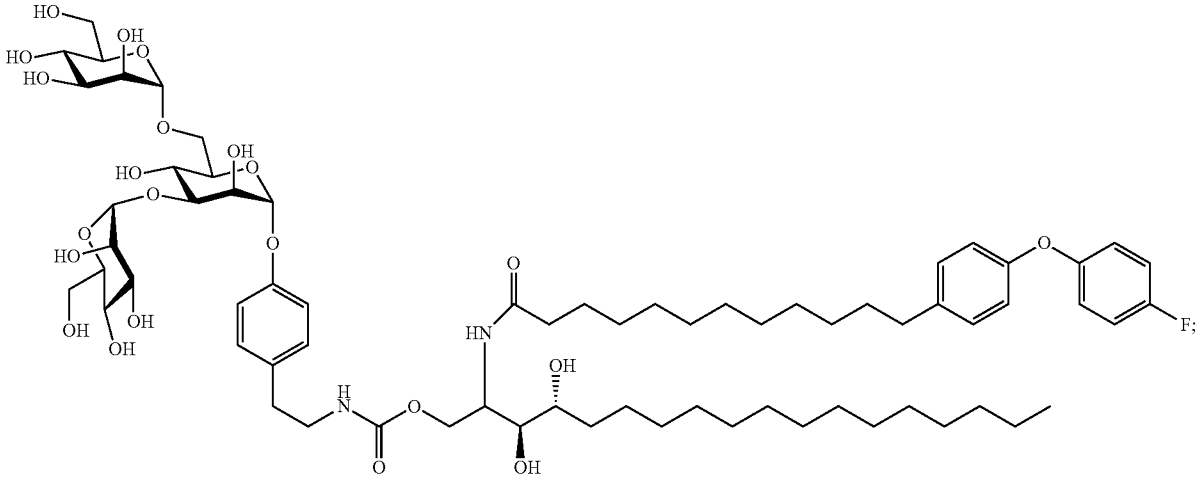
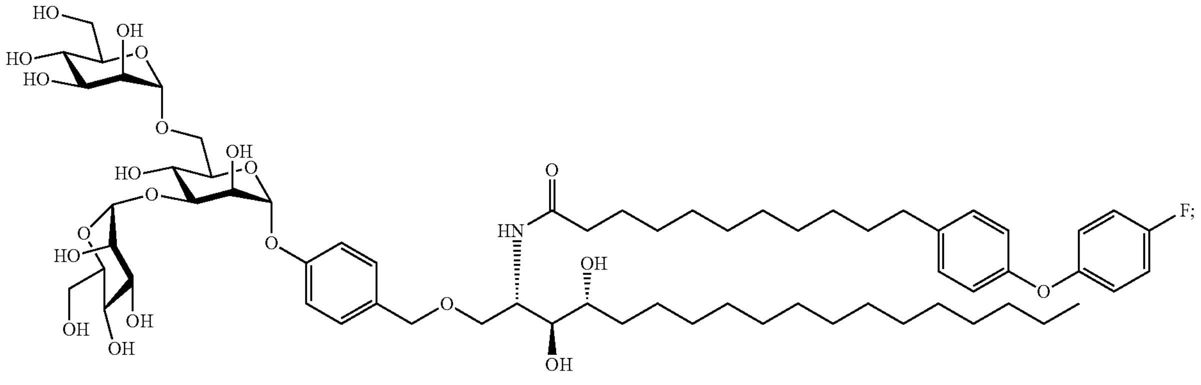

-continued

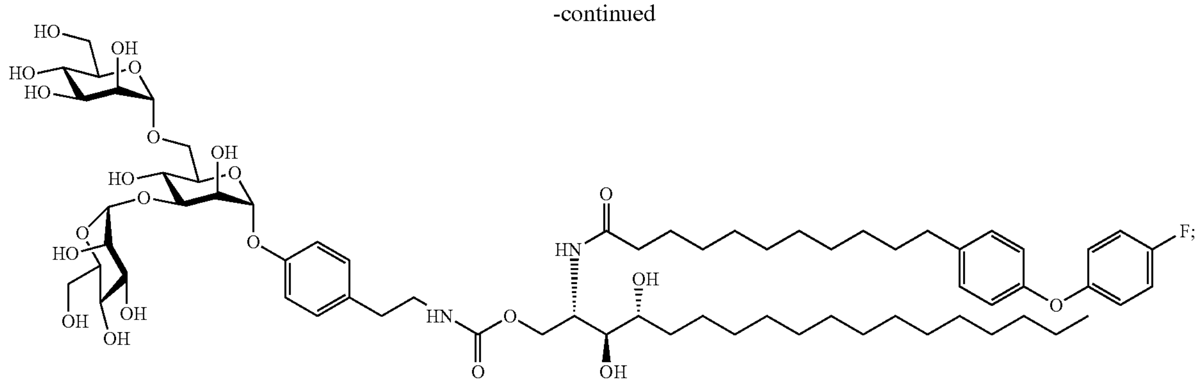

;

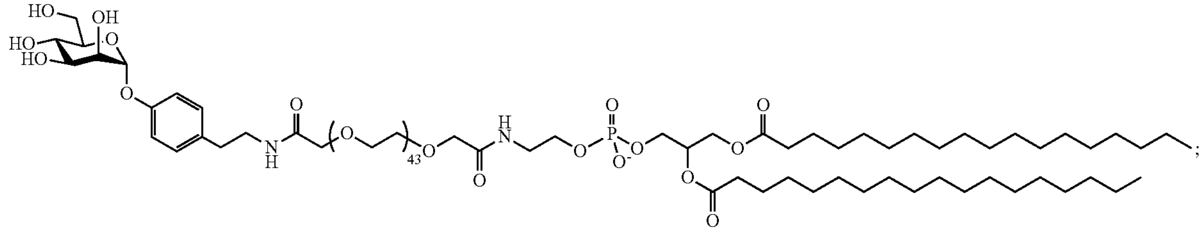

;

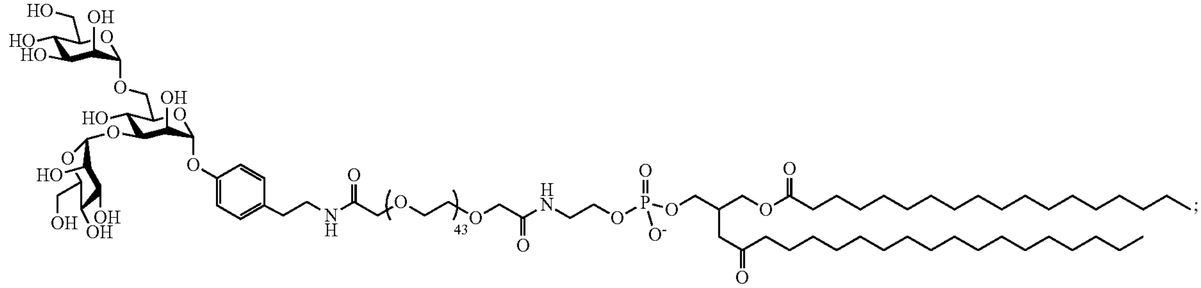

;

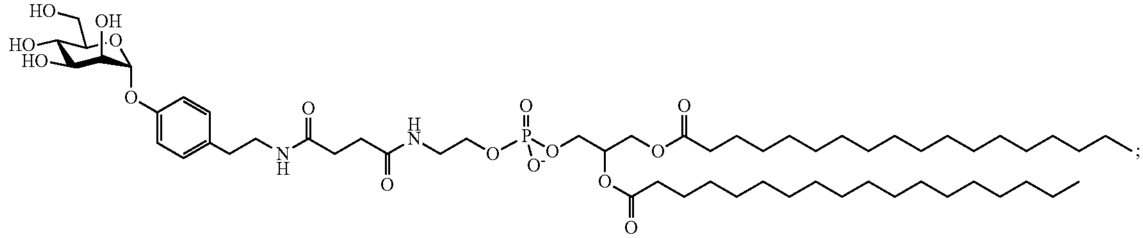

; and

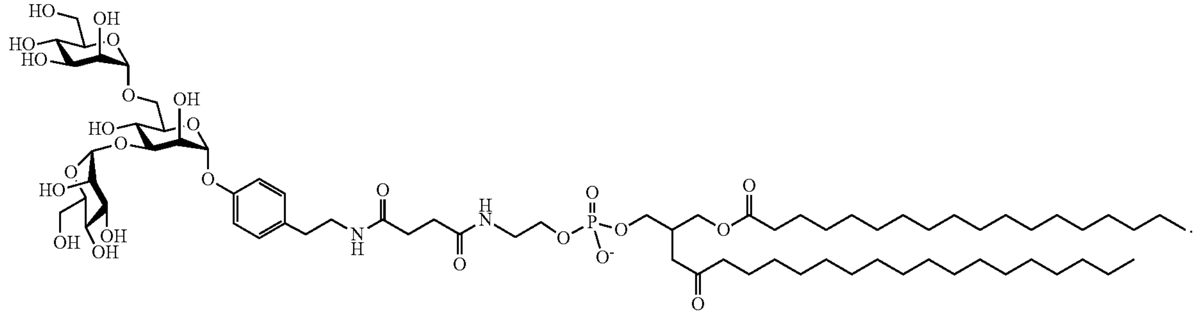

.

Embodiment 31. The component of any one of embodiments 1 to 30, wherein the component is not glycolipid C34 or α-galactosylceramide.

Embodiment 32. A formulation for forming a lipid nanoparticle, comprising the compound of any one of embodiments 1 to 31, wherein the compound comprises 1 to 10 mol % of the composition.

Embodiment 33. The formulation of embodiment 32, further comprises an ionizable lipid, a helper lipid, or a mixture thereof, wherein the ionizable lipid comprises 30 to 60 mol % of the composition, the helper lipid comprises 5 to 60 mol % of the composition, and the rest percent is a carrier or a solvent.

Embodiment 34. The formulation of embodiment 33, wherein the ionizable lipid comprises heptadecan-9-yl 8-[2-hydroxyethyl-(6-oxo-6-undecoxyhexyl)amino]octanoate (SM-102™) (4 hydroxybutyl)azanediyl)bis(hexane-6,1-diyl)bis(2-hexyldecanoate) (ALC-0315™, Pfizer), or a combination thereof.

Embodiment 35. The formulation of embodiment 33 or embodiment 34, wherein the helper lipid comprises a phosphatidylcholine, a cholesterol or a derivative thereof, a polyethylene glycol-lipid (PEG-lipid), or a mixture thereof, wherein the phosphatidylcholine comprises 5 to 10 mol % of the composition, the cholesterol or a derivative thereof comprises 30 to 40 mol % of the composition, and the polyethylene glycol-lipid (PEG-lipid) comprises 1 to 10 mol % of the composition.

Embodiment 36. The formulation of embodiment 35, wherein the phosphatidylcholine comprises distearoylphosphatidylcholine (DSPC), dioleoylphosphatidylethanolamine (DPOE), or a mixture thereof.

Embodiment 37. The formulation of embodiment 35 or embodiment 36, wherein the cholesterol or a derivative thereof is a cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (3β,5β)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

Embodiment 38. The formulation of any one of embodiments 35 to 37, wherein the PEG-lipid is DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof.

Embodiment 39. The formulation of any one of embodiments 33 to 38, further comprising a payload.

Embodiment 40. The formulation of embodiment 39, wherein the payload is a nucleic acid, a compound, a polypeptide, a protein, a glycan, or a combination thereof.

Embodiment 41. The formulation of embodiment 40, wherein the nucleic acid is RNA or DNA.

Embodiment 42. The formulation of embodiment 41, wherein the payload encodes a polypeptide.

Embodiment 43. The formulation of any one of embodiments 39 to 42, wherein the payload is immunogenic, or the payload is a nucleic acid configured to encode an immunogenic polypeptide or protein.

Embodiment 44. The formulation of any one of embodiments 39 to 43, wherein the payload is a first payload, and the composition further encapsulates a second payload, wherein the second payload is a nucleic acid, a compound, a polypeptide, a protein, a glycan, or a combination thereof.

Embodiment 45. The formulation of embodiment 44, wherein the first payload and the second payload are different.

Embodiment 46. The formulation of any one of embodiments 32 to 45, further comprising a pharmaceutically acceptable excipient, adjuvant, or a combination thereof.

Embodiment 47. A lipid nanoparticle, comprising a membrane defining an inner space, wherein the membrane is formed with a plurality of lipid components comprising the compound of any one of embodiments 1 to 31.

Embodiment 48. The lipid nanoparticle of embodiment 47, wherein the plurality of the lipid components further comprises an ionizable lipid, a helper lipid, or a combination thereof.

Embodiment 49. The lipid nanoparticle of embodiment 47 or embodiment 48, wherein the membrane is formed via hydrophobic interaction between the plurality of the lipid components.

Embodiment 50. The lipid nanoparticle of embodiment 49, wherein the ionizable lipid comprises heptadecan-9-yl 8-[2-hydroxyethyl-(6-oxo-6-undecoxyhexyl)amino]octanoate (SM-102™) (4 hydroxybutyl)azanediyl)bis(hexane-6,1-diyl)bis(2-hexyldecanoate) (ALC-0315™, Pfizer), or a combination thereof.

Embodiment 51. The lipid nanoparticle of embodiment 49 or embodiment 50, wherein the helper lipid comprises a phosphatidylcholine, a cholesterol or a derivative thereof, a polyethylene glycol-lipid (PEG-lipid), or a mixture thereof.

Embodiment 52. The lipid nanoparticle of embodiment 51, wherein the phosphatidylcholine comprises distearoylphosphatidylcholine (DSPC), dioleoylphosphatidylethanolamine (DPOE), or a mixture thereof.

Embodiment 53. The lipid nanoparticle of embodiment 51 or embodiment 52, wherein the cholesterol or a derivative thereof is a cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (3β,5β)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

Embodiment 54. The lipid nanoparticle of any one of embodiments 51 to 53, wherein the PEG-lipid is DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof.

Embodiment 55. The lipid nanoparticle of any one of embodiments 47 to 54, wherein the membrane encapsulates a payload.

Embodiment 56. The lipid nanoparticle of embodiment 55, wherein the payload is a nucleic acid, a compound, a polypeptide, a protein, a glycan, or a combination thereof.

Embodiment 57. The lipid nanoparticle of embodiment 56, wherein the nucleic acid is RNA or DNA.

Embodiment 58. The lipid nanoparticle of embodiment 57, wherein the payload encodes a polypeptide.

Embodiment 59. The lipid nanoparticle of any one of embodiments 55 to 58, wherein the payload is immunogenic, or the payload is a nucleic acid configured to encode an immunogenic polypeptide or protein.

Embodiment 60. The lipid nanoparticle of any one of embodiments 55 to 59, wherein the payload is a first payload, and the membrane further encapsulates a second payload.

Embodiment 61. The lipid nanoparticle of embodiment 60, wherein the second payload is a nucleic acid, a compound, a polypeptide, a protein, a glycan, or a combination thereof.

Embodiment 62. The lipid nanoparticle of embodiment 60 or embodiment 61, wherein the first payload and the second payload are different.

Embodiment 63. The lipid nanoparticle of any one of embodiments 47 to 62, being made from the composition of any one of embodiments 29 to 43.

Embodiment 64. The lipid nanoparticle of any one of embodiments 47 to 63, wherein the membrane is a bi-layer structure.

Embodiment 65. The lipid nanoparticle of any one of embodiments 47 to 64, having a diameter of 0.01 to 5 microns.

Embodiment 66. The lipid nanoparticle of any one of embodiments 47 to 65, wherein the plurality of the lipid components does not comprise glycolipid C34 or α-galactosylceramide (α-GalCer).

Embodiment 67. A formulation, comprising the lipid nanoparticle of any one of embodiments 47 to 66.

Embodiment 68. The formulation of embodiment 67, comprising 0.01 to 95% (w/w) of the lipid nanoparticle.

Embodiment 69. The formulation of embodiment 67 or embodiment 68, wherein the lipid nanoparticle is a first lipid nanoparticle, and the composition further comprises a second lipid nanoparticle.

Embodiment 70. The formulation of embodiment 69, wherein the first lipid nanoparticle and the second lipid nanoparticle are different in size, membrane components, payload encapsulated therewithin, or a combination thereof.

Embodiment 71. The formulation of any one of embodiments 67 to 70, further comprising an excipient, an adjuvant, or a combination thereof.

Embodiment 72. The formulation of embodiment 71, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

Embodiment 73. The formulation of embodiment 71 or embodiment 72, wherein the adjuvant comprises C34, Gluco-C34, 7DW8-5, α-galactosylceramide, Aluminum salt, Squalene, MF59®, or QS-21. Other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03®, CpG 1018®, or a combination thereof.

Embodiment 74. A kit for preparing a lipid nanoparticle, comprising: a first reagent, comprising the compound of any one of embodiments 1 to 31; and a second reagent, comprising an ionizable lipid, a helper lipid, or a mixture thereof.

Embodiment 75. The kit of embodiment 74, wherein the second reagent comprises the ionizable lipid.

Embodiment 76. The kit of embodiment 75, wherein the kit further comprises a third reagent comprising a helper lipid.

Embodiment 77. The kit of any one of embodiments 74 to 76, wherein ionizable lipid comprises heptadecan-9-yl 8-[2-hydroxyethyl-(6-oxo-6-undecoxyhexyl)amino]octanoate (SM-102™) (4 hydroxybutyl)azanediyl)bis(hexane-6,1-diyl)bis(2-hexyldecanoate) (ALC-0315™ Pfizer), or a combination thereof.

Embodiment 78. The kit of any one of embodiments 74 to 77, wherein the helper lipid comprises a phosphatidylcholine, a cholesterol or a derivative thereof, a polyethylene glycol-lipid (PEG-lipid), or a mixture thereof.

Embodiment 79. The kit of embodiment 78, wherein the phosphatidylcholine comprises distearoylphosphatidylcholine (DSPC), dioleoylphosphatidylethanolamine (DPOE), or a mixture thereof.

Embodiment 80. The kit of embodiment 78 or embodiment 79, wherein the cholesterol or a derivative thereof is a cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (3β,5β)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

Embodiment 81. The kit of any one of embodiments 78 to 80, wherein the PEG-lipid is DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof.

Embodiment 82. The kit of any one of embodiments 74 to 81, further comprising a fourth reagent, comprising a payload, wherein the payload is a nucleic acid, a compound, a polypeptide, a protein, a glycan, or a combination thereof.

Embodiment 83. The kit of embodiment 82, wherein the nucleic acid is RNA or DNA.

Embodiment 84. The kit of embodiment 83, wherein the payload encodes a polypeptide.

Embodiment 85. The kit of any one of embodiments 82 to 84, wherein the payload is immunogenic, or the payload is a nucleic acid configured to encode an immunogenic polypeptide or protein.

Embodiment 86. A method of targeted payload delivery in a subject, comprising administering to the subject an effective amount of the lipid nanoparticle of any one of embodiments 47 to 54, wherein the payload is a nucleic acid, a compound, a polypeptide, a protein, a glycan, or a combination thereof, and the payload is encapsulated by the lipid nanoparticle.

Embodiment 87. The method of embodiment 86, wherein the nucleic acid is RNA or DNA.

Embodiment 88. The method of embodiment 87, wherein the payload encodes a polypeptide.

Embodiment 89. The method of any one of embodiments 86 to 88, wherein the payload is immunogenic, or the payload is a nucleic acid configured to encode an immunogenic polypeptide or protein.

Embodiment 90. The method of any one of embodiments 86 to 89, wherein the payload is a first payload, and the membrane further encapsulates a second payload, wherein the second payload is a nucleic acid, a compound, a polypeptide, a protein, a glycan, or a combination thereof.

Embodiment 91. The method of embodiment 90, wherein the first payload and the second payload are different.

Embodiment 92. The method of any one of embodiments 86 to 91, wherein the lipid nanoparticle is administered together with an excipient, an adjuvant, or a combination thereof.

Embodiment 93. The method of embodiment 92, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

Embodiment 94. The method of embodiment 92 or embodiment 93, wherein the adjuvant comprises C34, Gluco-C34, 7DW8-5, C17, C23, C30, α-galactosylceramide, Aluminum salt, Squalene, MF59®, or QS-21. Other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03®, CpG 1018®, or a combination thereof.

Embodiment 95. A method of preventing or treating a disease in a subject, comprising administering to the subject an effective amount of the lipid nanoparticle of any one of embodiments 47 to 54, wherein the payload is a nucleic acid, a compound, a polypeptide, a protein, a glycan, or a combination thereof, and the payload is encapsulated within the lipid nanoparticle; and wherein the payload is a therapeutic agent or derives a therapeutic agent.

Embodiment 96. The method of embodiment 95, wherein the nucleic acid is RNA or DNA.

Embodiment 97. The method of embodiment 96, wherein the payload encodes a polypeptide.

Embodiment 98. The method of any one of embodiments 95 to 97, wherein the payload is immunogenic, or the payload is a nucleic acid configured to encode an immunogenic polypeptide or protein.

Embodiment 99. The method of any one of embodiments 95 to 98, wherein the payload is a first payload, and the membrane further encapsulates a second payload, wherein the second payload is a nucleic acid, a compound, a polypeptide, a protein, a glycan, or a combination thereof.

Embodiment 100. The method of embodiment 99, wherein the first payload and the second payload are different.

Embodiment 101. The method of any one of embodiments 95 to 100, wherein the lipid nanoparticle is administered together with an excipient, an adjuvant, or a combination thereof.

Embodiment 102. The method of embodiment 101, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

Embodiment 103. The method of embodiment 101 or embodiment 102, wherein the adjuvant comprises C34, Gluco-C34, 7DW8-5, C17, C23, C30, α-galactosylceramide, Aluminum salt, Squalene, MF59®, or QS-21. Other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03®, CpG 1018®, or a combination thereof.

Embodiment 104. The method of any one of embodiments 95 to 103, wherein the lipid nanoparticle is administered in an initial dose and followed by one, two, three, four, five, or more booster doses.

Embodiment 105. The method of embodiment 104, wherein the booster doses are administered about one month, about two months, about three months, about four months, about five months, or about six months or more following the initial dose.

Embodiment 106. The method of any one of embodiments 95 to 105, wherein the effective amount ranges from about 5 g to 1000 g.

Embodiment 107. A method of boosting an adaptive immune response, comprising administering to the subject an effective amount of the lipid nanoparticle of any one of embodiments 47 to 54, wherein the payload is a nucleic acid, a compound, a polypeptide, a protein, a glycan, or a combination thereof, and the payload is encapsulated within the lipid nanoparticle; and wherein the payload is immunogenic or derives an immunogenic biomolecule.

Embodiment 108. The method of embodiment 107, wherein the nucleic acid is RNA or DNA.

Embodiment 109. The method of embodiment 108, wherein the payload encodes a polypeptide.

Embodiment 110. The method of any one of embodiments 107 to 109, wherein the payload is a first payload, and the membrane further encapsulates a second payload, wherein the second payload is a nucleic acid, a compound, a polypeptide, a protein, a glycan, or a combination thereof.

Embodiment 111. The method of embodiment 110, wherein the first payload and the second payload are different.

Embodiment 112. The method of any one of embodiments 107 to 111, wherein the lipid nanoparticle is administered together with an excipient, an adjuvant, or a combination thereof.

Embodiment 113. The method of embodiment 112, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

Embodiment 114. The method of embodiment 112 or embodiment 113, wherein the adjuvant comprises C34, Gluco-C34, 7DW8-5, C17, C23, C30, α-galactosylceramide, Aluminum salt, Squalene, MF59®, or QS-21. Other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03, CpG 1018®, or a combination thereof.

Embodiment 115. The method of any one of embodiments 107 to 114, wherein the lipid nanoparticle is administered in an initial dose and followed by one, two, three, four, five, or more booster doses.

Embodiment 116. The method of embodiment 115, wherein the booster doses are administered about one month, about two months, about three months, about four months, about five months, or about six months or more following the initial dose.

Embodiment 117. The method of any one of embodiments 107 to 116, wherein the effective amount ranges from about 5 g to 1000 g.

What is claimed is:

1. A lipid nanoparticle, comprising a membrane defining an inner space, wherein the membrane is formed with a plurality of lipid components, wherein the plurality of lipid components comprises a compound comprising Formula 1 or Formula 2:

Formula 1

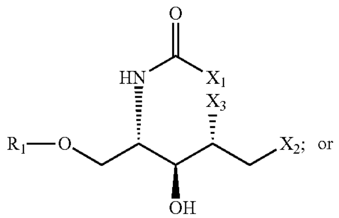

; or

Formula 2

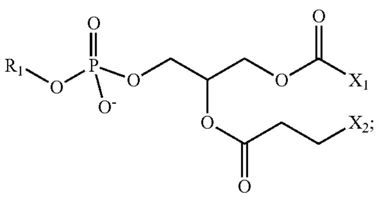

;

wherein $R_1$ comprises a formula of $R_2$-$R_A$—, wherein $R_A$ is an attachment group and $R_2$ is a substituted or non-substituted glycosyl group, and wherein the attachment group comprises an aryl and an alkylamide, having a structure of -aryl-alkyl-NH—C(O)—, and the aryl moiety attaches to $R_2$;

wherein $X_1$ and $X_2$ are each independently hydrogen, $C_{1-30}$ alkyl, $C_{1-30}$ alkenyl, $C_{1-30}$ alkynyl, aryl, aryloxy, or a substituted version thereof, or —$(CH_2)nX_4$, n is 0 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof; and wherein $X_3$ is hydrogen, $C_{1-6}$ alkyl, or hydroxyl.

2. The lipid nanoparticle of claim 1, wherein the plurality of the lipid components further comprises an ionizable lipid, a helper lipid, or a combination thereof.

3. The lipid nanoparticle of claim 2, wherein the ionizable lipid comprises heptadecan-9-yl 8-[2-hydroxyethyl-(6-oxo-6-undecoxyhexyl)amino]octanoate, (4-hydroxybutyl) azanediyl)bis(hexane-6,1-diyl)bis(2-hexyldecanoate), or a combination thereof.

4. The lipid nanoparticle of claim 2, wherein the helper lipid comprises a phosphatidylcholine, a cholesterol or a derivative thereof, a polyethylene glycol-lipid (PEG-lipid), or a mixture thereof.

5. The lipid nanoparticle of claim 4, wherein the phosphatidylcholine comprises distearoylphosphatidylcholine (DSPC), dioleoylphosphatidylethanolamine (DPOE), or a mixture thereof.

6. The lipid nanoparticle of claim 4, wherein the cholesterol or the derivative thereof is a cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (30,50)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

7. The lipid nanoparticle of claim 4, wherein the PEG-lipid is DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof.

8. The lipid nanoparticle of claim 1, wherein the membrane encapsulates a payload, wherein the payload is a nucleic acid, a compound, a polypeptide, a protein, a glycan, or a combination thereof.

9. The lipid nanoparticle of claim 8, wherein the payload is immunogenic, or the payload is a nucleic acid configured to encode an immunogenic polypeptide or protein.

10. The lipid nanoparticle of claim 8, wherein the payload is a first payload, and the membrane further encapsulates a second payload, wherein the second payload is a nucleic acid, a compound, a polypeptide, a protein, a glycan, or a combination thereof, and the first payload and the second payload are different.

11. The lipid nanoparticle of claim 1, having a diameter of 0.01 to 5 microns.

12. A formulation, comprising the lipid nanoparticle of claim 1.

13. The formulation of claim 12, comprising 0.01 to 95% (w/w) of the lipid nanoparticle.

14. The formulation of claim 12, wherein the lipid nanoparticle is a first lipid nanoparticle, and the formulation further comprises a second lipid nanoparticle, further wherein the first lipid nanoparticle and the second lipid nanoparticle are different in size, membrane components, payload encapsulated therewithin, or a combination thereof.

15. The formulation of claim 12, further comprising an excipient, an adjuvant, or a combination thereof, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof, and/or the adjuvant comprises C34, (2S, 3S, 4R)-1-O-(a-D-galactopyranosyl)-N-(11-(4-fluorophenyl)undecanoyl)-2-amino-1,3,4-octadecanetriol) (7DW8-5), α-galactosylceramide, Aluminum salt, Squalene, an oil-in-water emulsion comprising squalene, polysorbate 80 and sorbitan trioleate, or QS-21, aluminum hydroxide, aluminum phosphate, alum (potassium aluminum sulfate), mixed aluminum salts, Freund's complete adjuvant, Freund's incomplete adjuvant, an oil-in-water emulsion comprising α-tocopherol, squalene and polysorbate 80, a synthetic, Toll-like receptor 9 (TLR9) agonist adjuvant, or a combination thereof.

16. A kit for preparing a lipid nanoparticle, comprising:

a first reagent, comprising a compound having Formula 1 or Formula 2:

Formula 1

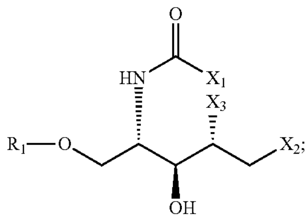

; or

Formula 2

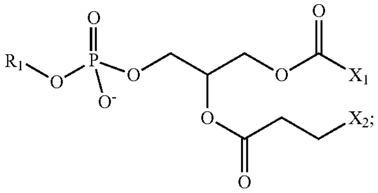

;

wherein $R_1$ comprises a formula of $R_2$-$R_A$—, wherein $R_A$ is an attachment group and $R_2$ is a substituted or non-substituted glycosyl group, and wherein the attachment group comprises an aryl and an alkylamide, having a structure of -aryl-alkyl-NH—C(O)—, and the aryl moiety attaches to $R_2$;

wherein $X_1$ and $X_2$ are each independently hydrogen, $C_{1-30}$ alkyl, $C_{1-30}$ alkenyl, $C_{1-30}$ alkynyl, aryl, aryloxy, or a substituted version thereof, or —$(CH_2)nX_4$, n is 0 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof, and wherein $X_3$ is hydrogen, $C_{1-6}$ alkyl, or hydroxyl; and a second reagent, comprising an ionizable lipid, a helper lipid, or a mixture thereof.

17. The kit of claim 16, wherein the second reagent comprises the ionizable lipid and a helper lipid.

18. The kit of claim 16, wherein the ionizable lipid comprises heptadecan-9-yl 8-[2-hydroxyethyl-(6-oxo-6-undecoxyhexyl)amino]octanoate, (4-hydroxybutyl)azanediyl) bis(hexane-6,1-diyl)bis(2-hexyldecanoate), or a combination thereof.

19. The kit of claim 16, wherein the helper lipid comprises a phosphatidylcholine, a cholesterol or a derivative thereof, a polyethylene glycol-lipid (PEG-lipid), or a mixture thereof.

20. The kit of claim 19, wherein the phosphatidylcholine comprises distearoylphosphatidylcholine (DSPC), dioleoylphosphatidylethanolamine (DPOE), or a mixture thereof.

21. The kit of claim 19, wherein the cholesterol or a derivative thereof is a cholesterol, campesterol, beta-sitosterol, brassicasterol, ergosterol, dehydroergosterol, stigmasterol, fucosterol, DC-cholesterol HCl, OH-Chol, HAPC-Chol, MHAPC-Chol, DMHAPC-Chol, DMPAC-Chol, cholesteryl chloroformate, GL67, cholesteryl myristate, cholesteryl oleate, cholesteryl nervonate, LC10, cholesteryl hemisuccinate, (30,50)-3-hydroxycholan-24-oic acid, alkyne cholesterol, 27-alkyne cholesterol, E-cholesterol alkyne, trifluoroacetate salt (Dios-Arg, 2H-Cho-Arg, or Cho-Arg), or a mixture thereof.

22. The kit of claim 19, wherein the PEG-lipid is DMG-PEG, DSG-PEG, mPEG-DPPE, DOPE-PEG, mPEG-DMPE, mPEG-DOPE, DSPE-PEG-amine, DSPE-PEG, mPEG-DSPE, PEG PE, m-PEG-Pentacosadiynoic acid, bromoacetamido-PEG, amine-PEG, azide-PEG, or a mixture thereof.

23. The kit of claim 16, further comprising a payload, wherein the payload is a nucleic acid, a compound, a polypeptide, a protein, a glycan, or a combination thereof.

24. The kit of claim 23, wherein the payload is immunogenic, or the payload is a nucleic acid configured to encode an immunogenic polypeptide or protein.

25. The lipid nanoparticle of claim 1, wherein $R_A$ further comprises a polyethylene glycol (PEG) moiety having 2 to 72 ($OCH_2CH_2$) subunits.

26. The lipid nanoparticle of claim 1, wherein the substituted or non-substituted glycosyl group comprises mannoside, fucoside, or a combination thereof.

27. The lipid nanoparticle of claim 1, wherein the substituted or non-substituted glycosyl group comprises a mono-mannoside, a di-mannoside, or a tri-mannoside.

28. The lipid nanoparticle of claim 1, wherein $R_1$ is a substituted glycosyl group, comprising 1 to 6 substituents, wherein each of the 1 to 6 substituents is $C_{1-6}$ alkyl, $C_{1-6}$ alkenyl, halogen, $C_{1-6}$ alkyl halide, $C_{1-6}$ alkoxy, amine, nitro, $C_{1-6}$ alkyl amine, amide, azido, aryl, cycloalkyl, heterocycloalkyl, sulfite, or a substituted version thereof, or a combination thereof.

29. The lipid nanoparticle of claim 1, wherein $R_1$ is selected from the group consisting of:

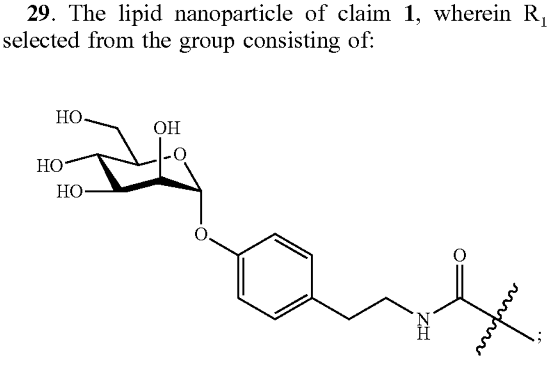
;

-continued

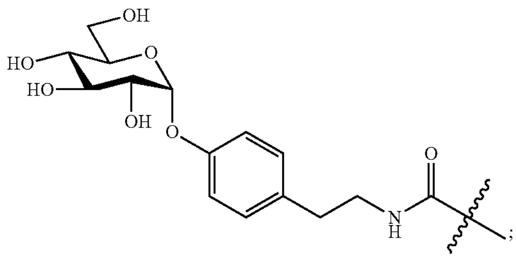
;

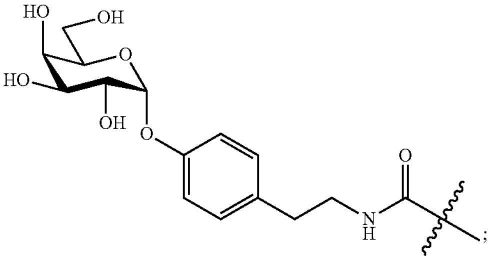
;

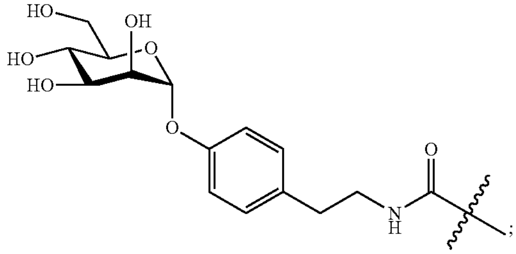
;

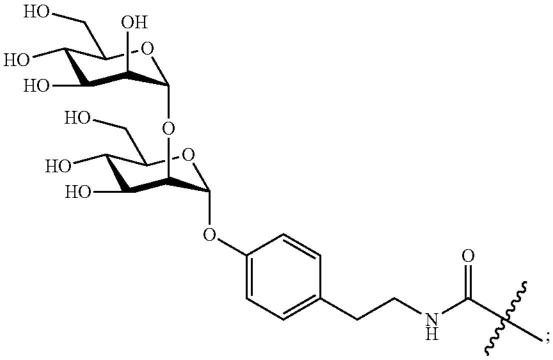
;

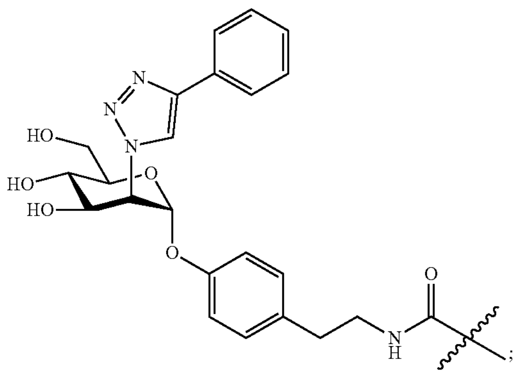
;

-continued

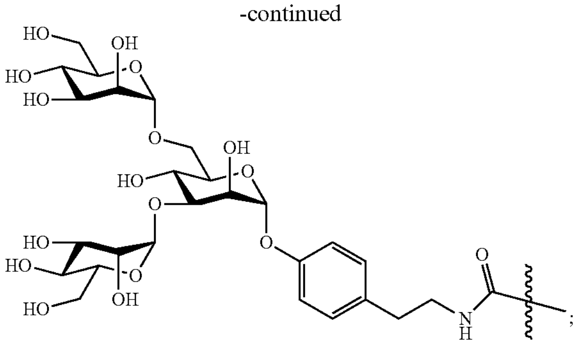

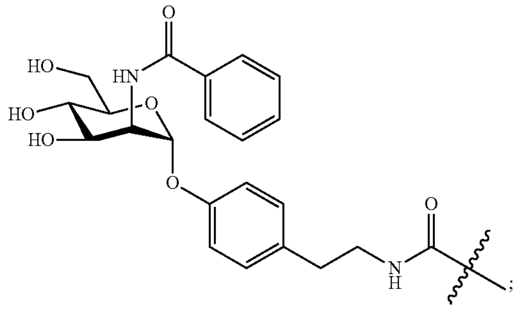

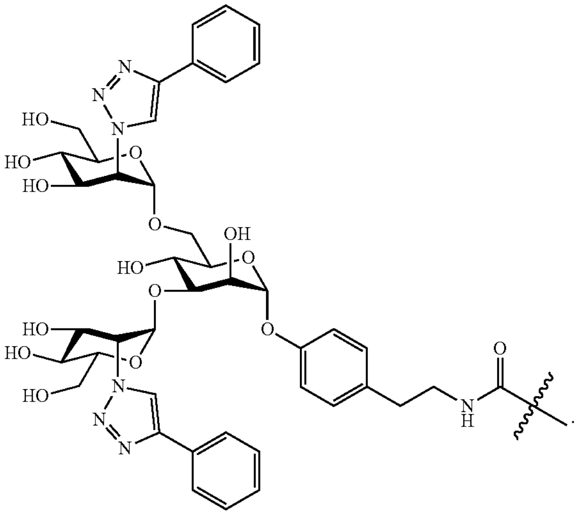

30. The lipid nanoparticle of claim 1, wherein the compound is of Formula 3:

Formula 3

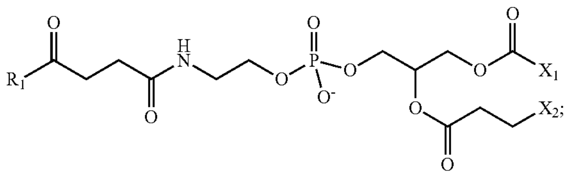

and wherein $R_1$ is selected from the group consisting of:

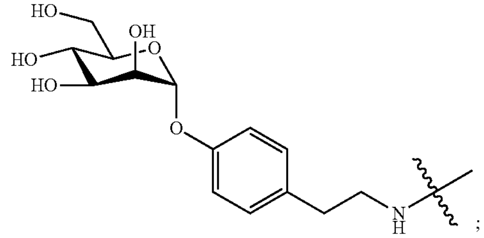

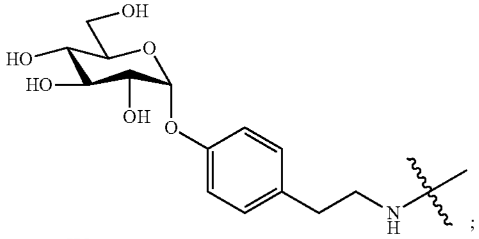

and

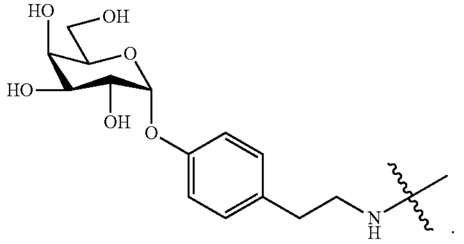

31. The lipid nanoparticle of claim 1, wherein at least one of $X_1$ and $X_2$ comprises a saturated hydrocarbon chain, comprising at least 2, 3, 4, 5, 6, 7, 8, 9, 10, 11, 12, 13, 14, 15, 16, 17, 18, 19, 20, 22, 24, 26, 28, or 30 carbons; and/or wherein $X_1$ and $X_2$ are each independently hydrogen, $C_{4-30}$ alkyl, $C_{4-30}$ alkenyl, $C_{4-30}$ alkynyl, aryl, aryloxy, or a substituted version thereof, or —$(CH_2)nX_4$, n is 4 to 30, and $X_4$ is hydrogen, aryl, aryloxy, heterocyclic group, or a substituted version thereof, provided that when $X_4$ is a heterocyclic group, the heterocyclic group comprises 1 to 3 heteroatoms, selected from the group consisting of O, S, and N, or a combination thereof.

32. The lipid nanoparticle of claim 1, provided that when one of $X_1$ and $X_2$ is hydrogen, the other one is not hydrogen, or when one of $X_1$ and $X_2$ is $C_{15-30}$ alkyl, the other one is —$(CH_2)nX_4$.

33. The lipid nanoparticle of claim 1, wherein $X_4$ is —$R_3$—O—$R_4$, wherein $R_3$ and $R_4$ are each independently aryl, heterocyclic group, cycloalkyl, heterocycloalkyl, each comprising 0 to 6 substituents selected from the group consisting of $C_{1-6}$ alkyl, halogen, $C_{1-6}$ alkyl halogen, and $C_{1-6}$ alkoxy.

34. The lipid nanoparticle of claim 1, wherein $X_4$ is selected from the group consisting of:

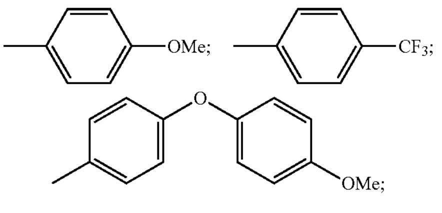

-continued
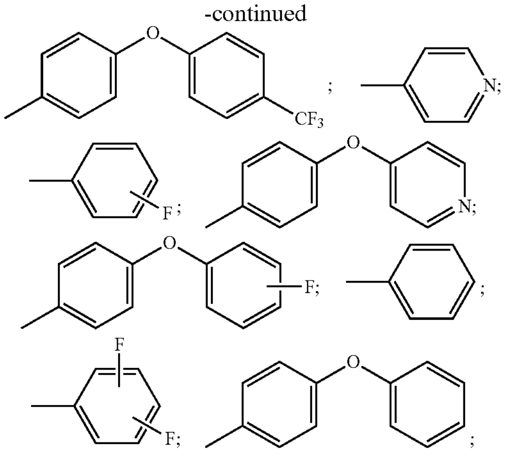
-continued
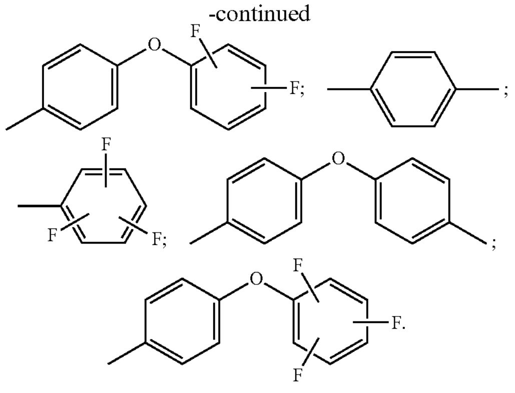
35. The lipid nanoparticle of claim 1, wherein the compound is selected from the group consisting of:
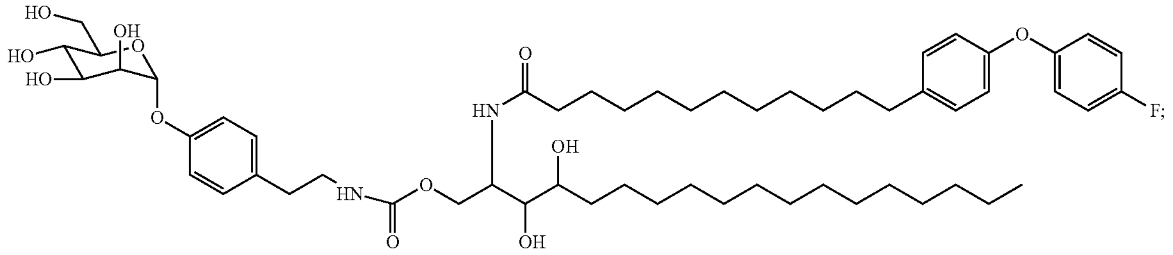
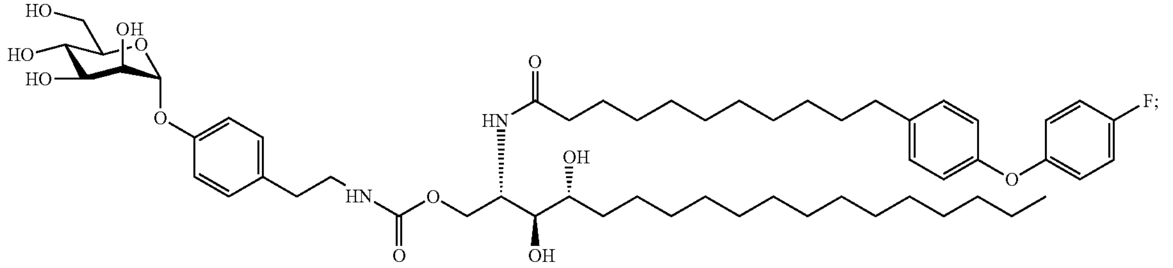
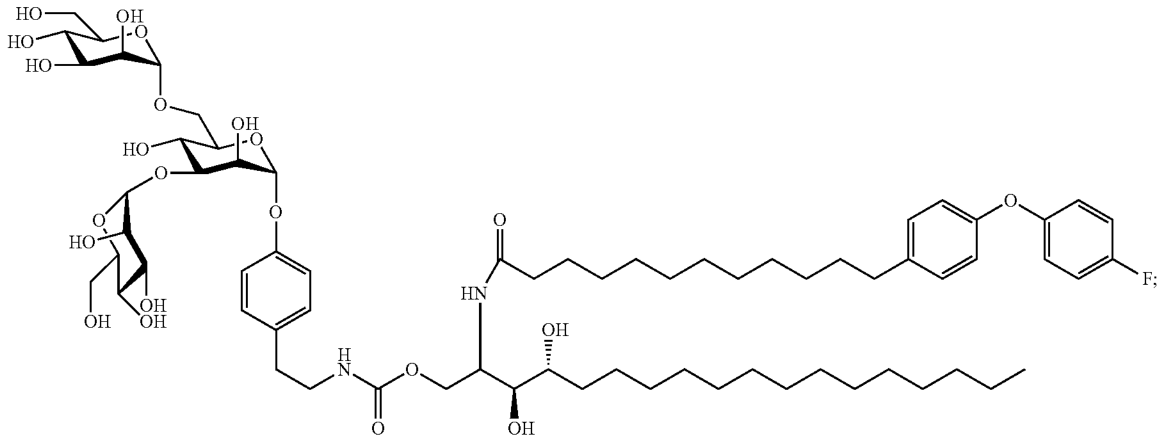

-continued
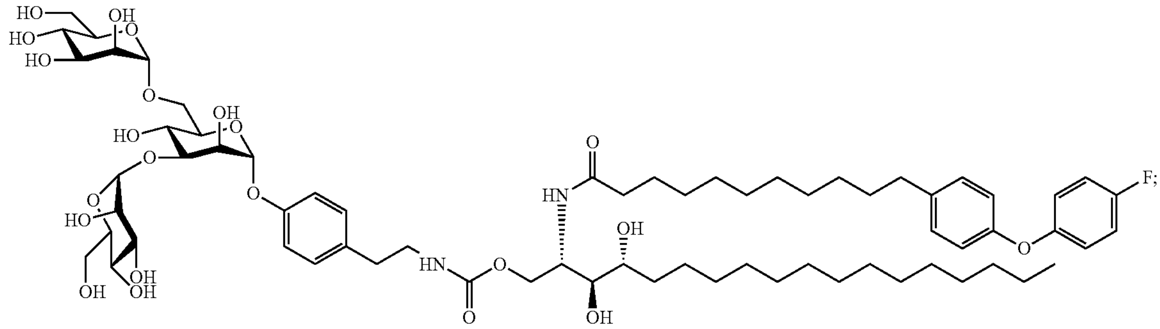
;
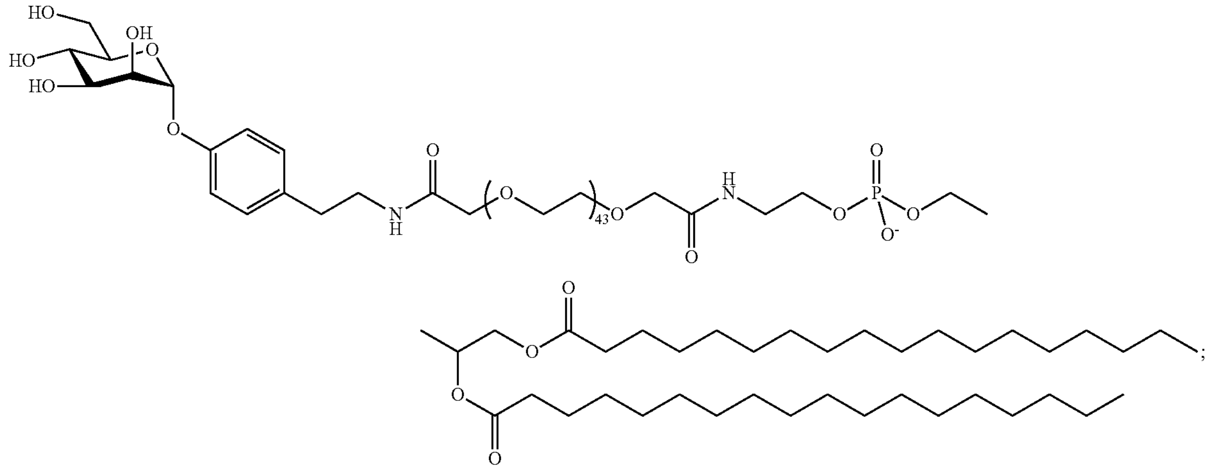
;
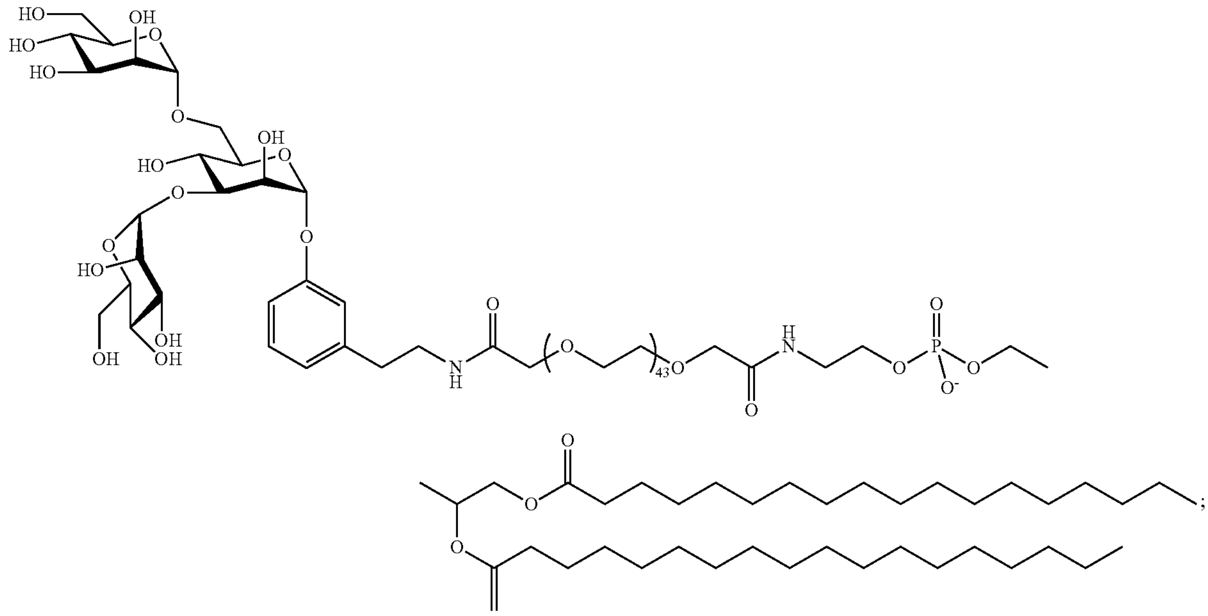
;
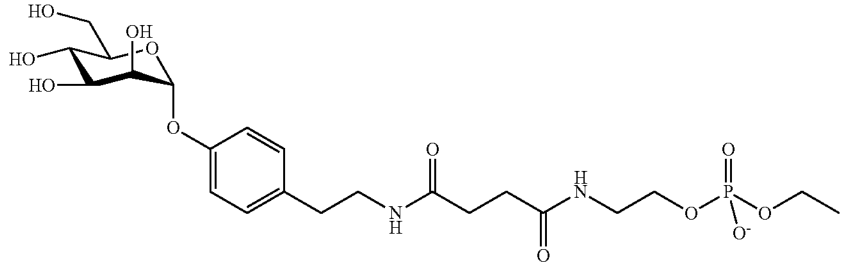

-continued
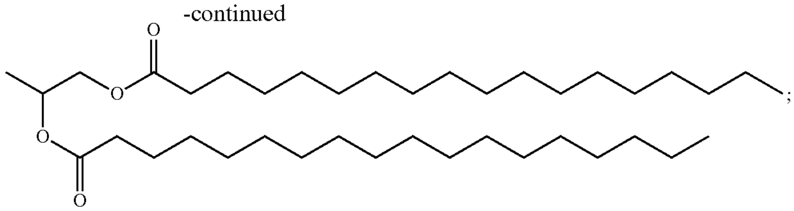
; and
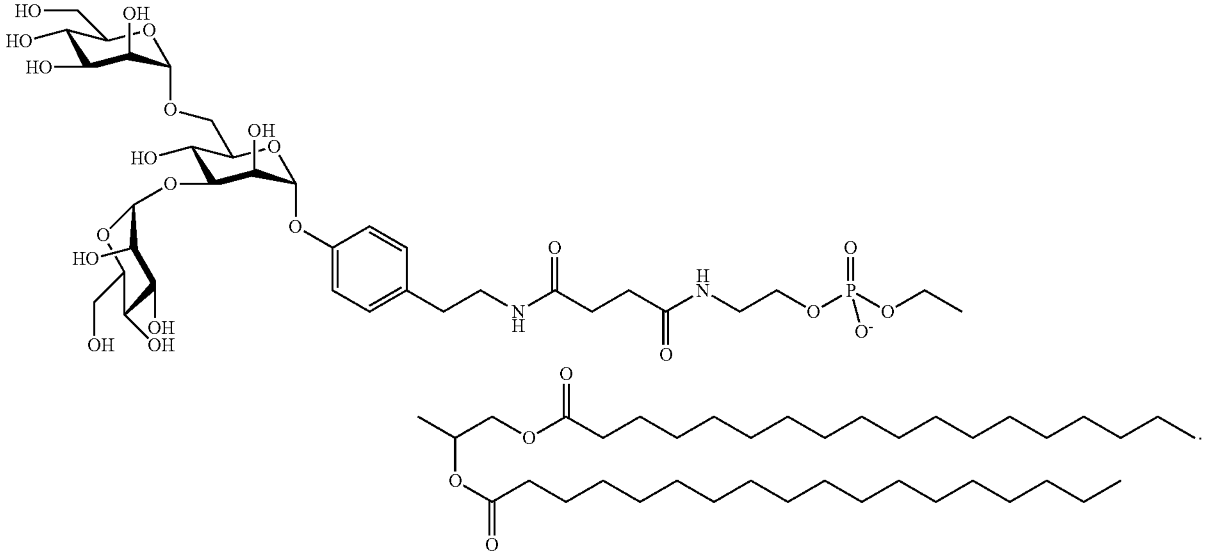
.
* * * * *